(12) United States Patent
Purcell et al.

(10) Patent No.: US 11,530,304 B2
(45) Date of Patent: *Dec. 20, 2022

(54) BIOFABRICATED MATERIAL CONTAINING COLLAGEN FIBRILS

(71) Applicant: MODERN MEADOW, INC., Nutley, NJ (US)

(72) Inventors: Brendan Patrick Purcell, Brooklyn, NY (US); David Thomas Williamson, Landenberg, PA (US); Lixin Dai, Staten Island, NY (US); Darryl Miles Cassingham, Dorset (GB); Stephen M. Spinella, Brooklyn, NY (US); Katherine Amy Congdon, Suffolk (GB)

(73) Assignee: MODERN MEADOW, INC., Nutley, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/433,566

(22) Filed: Feb. 15, 2017

(65) Prior Publication Data
US 2017/0233944 A1 Aug. 17, 2017

Related U.S. Application Data

(60) Provisional application No. 62/295,435, filed on Feb. 15, 2016.

(51) Int. Cl.
*B32B 5/26* (2006.01)
*D06N 3/00* (2006.01)
(Continued)

(52) U.S. Cl.
CPC .................... *C08J 3/24* (2013.01); *B32B 1/08* (2013.01); *B32B 3/266* (2013.01); *B32B 5/022* (2013.01);
(Continued)

(58) Field of Classification Search
CPC ....... D06N 3/0018; C08J 3/24; C08J 2389/06; C14C 13/00; D01F 4/00; D10B 2211/20; C12P 21/00
(Continued)

(56) References Cited

U.S. PATENT DOCUMENTS 2,059,856 A  11/1936  Eastman et al.
2,673,171 A   3/1954  Bellavoine
(Continued)

FOREIGN PATENT DOCUMENTS

CA   2306346 A1   1/1999
CN   1163642 A   10/1997
(Continued)

OTHER PUBLICATIONS

Jenkins, Cara et al. Effect of 3-Hydroxyproline Residues on Collagen Stability, Journal of American Chemical Society, vol. 125, No. 21, 2003, p. 6422-6427.*
(Continued)

*Primary Examiner* — Jennifer A Gillett
(74) *Attorney, Agent, or Firm* — Sterne, Kessler, Goldstein & Fox P.L.L.C

(57) ABSTRACT

A biofabricated material comprising a network of crosslinked collagen fibrils produced from recombinant collagen that contains substantially no 3-hydroxyproline residues is disclosed. This material is composed of collagen which is also a major component of natural leather and is produced by a process of fibrillation of collagen molecules into fibrils, crosslinking the fibrils and lubricating the crosslinked fibrils. Unlike natural leathers, this biofabricated material exhibits non-anisotropic (not directionally dependent) physical properties, for example, a sheet of biofabricated material can have substantially the same elasticity or tensile strength when stretched or stressed in different directions. Unlike
(Continued)

natural leather, it has a uniform texture that facilitates uniform uptake of dyes and coatings. Aesthetically, it produces a uniform and consistent grain for ease of manufacturability. It can have substantially identical grain, texture and other aesthetic properties on both sides distinct from natural leather where the grain increases from one side (e.g., distal surface) to the other (proximal inner layers).

26 Claims, 4 Drawing Sheets

Specification includes a Sequence Listing.

(51) Int. Cl.

| | |
|---|---|
| D06N 7/00 | (2006.01) |
| C08J 3/24 | (2006.01) |
| D01F 4/00 | (2006.01) |
| D06M 15/15 | (2006.01) |
| B32B 5/02 | (2006.01) |
| B32B 7/12 | (2006.01) |
| B32B 9/02 | (2006.01) |
| B32B 15/02 | (2006.01) |
| B32B 15/14 | (2006.01) |
| B32B 23/10 | (2006.01) |
| B32B 27/12 | (2006.01) |
| B32B 29/02 | (2006.01) |
| B32B 1/08 | (2006.01) |
| B32B 3/26 | (2006.01) |
| D04H 1/4382 | (2012.01) |
| C14C 13/00 | (2006.01) |
| D04H 13/00 | (2006.01) |
| D06P 3/32 | (2006.01) |
| C07K 14/78 | (2006.01) |
| C14C 9/00 | (2006.01) |
| C14C 9/02 | (2006.01) |
| D01C 3/00 | (2006.01) |
| D04H 1/00 | (2006.01) |
| D06M 15/05 | (2006.01) |
| D06M 23/16 | (2006.01) |
| D06M 101/06 | (2006.01) |

(52) U.S. Cl.
CPC .............. *B32B 5/024* (2013.01); *B32B 5/026* (2013.01); *B32B 5/26* (2013.01); *B32B 7/12* (2013.01); *B32B 9/025* (2013.01); *B32B 15/02* (2013.01); *B32B 15/14* (2013.01); *B32B 23/10* (2013.01); *B32B 27/12* (2013.01); *B32B 29/02* (2013.01); *C07K 14/78* (2013.01); *C14C 9/00* (2013.01); *C14C 9/02* (2013.01); *C14C 13/00* (2013.01); *D01C 3/00* (2013.01); *D01F 4/00* (2013.01); *D04H 1/00* (2013.01); *D04H 1/4382* (2013.01); *D04H 1/43838* (2020.05); *D04H 13/00* (2013.01); *D06M 15/05* (2013.01); *D06M 15/15* (2013.01); *D06N 3/00* (2013.01); *D06N 3/0018* (2013.01); *D06N 7/0097* (2013.01); *D06P 3/32* (2013.01); *B32B 2250/02* (2013.01); *B32B 2250/03* (2013.01); *B32B 2250/20* (2013.01); *B32B 2250/40* (2013.01); *B32B 2250/42* (2013.01); *B32B 2255/02* (2013.01); *B32B 2255/26* (2013.01); *B32B 2262/0207* (2013.01); *B32B 2262/0261* (2013.01); *B32B 2262/0269* (2013.01); *B32B 2262/0276* (2013.01); *B32B 2262/0292* (2013.01); *B32B 2262/04* (2013.01); *B32B 2262/062* (2013.01); *B32B 2262/065* (2013.01); *B32B 2262/067* (2013.01); *B32B 2262/08* (2013.01); *B32B 2262/10* (2013.01); *B32B 2262/101* (2013.01); *B32B 2262/103* (2013.01); *B32B 2262/106* (2013.01); *B32B 2262/14* (2013.01); *B32B 2264/105* (2013.01); *B32B 2307/202* (2013.01); *B32B 2307/208* (2013.01); *B32B 2307/308* (2013.01); *B32B 2307/4026* (2013.01); *B32B 2307/422* (2013.01); *B32B 2307/50* (2013.01); *B32B 2307/51* (2013.01); *B32B 2307/54* (2013.01); *B32B 2307/5825* (2013.01); *B32B 2307/708* (2013.01); *B32B 2307/7265* (2013.01); *B32B 2437/00* (2013.01); *B32B 2437/02* (2013.01); *B32B 2437/04* (2013.01); *B32B 2439/46* (2013.01); *B32B 2451/00* (2013.01); *B32B 2457/00* (2013.01); *B32B 2471/00* (2013.01); *B32B 2479/00* (2013.01); *B32B 2519/00* (2013.01); *B32B 2571/00* (2013.01); *B32B 2601/00* (2013.01); *B32B 2605/003* (2013.01); *B32B 2605/08* (2013.01); *B32B 2605/12* (2013.01); *B32B 2605/18* (2013.01); *C08J 2389/06* (2013.01); *D06M 23/16* (2013.01); *D06M 2101/06* (2013.01); *D06N 2201/06* (2013.01); *D06N 2203/02* (2013.01)

(58) Field of Classification Search
USPC .............. 442/100; 428/222, 473, 478.2, 904
See application file for complete search history.

(56) References Cited

U.S. PATENT DOCUMENTS

| | | |
|---|---|---|
| 2,934,446 A | 4/1960 | Highberger et al. |
| 3,073,714 A | 1/1963 | Tu et al. |
| 3,122,599 A | 2/1964 | Tu et al. |
| 3,136,682 A | 6/1964 | Tu et al. |
| 3,497,363 A | 2/1970 | Fox, Jr. et al. |
| 3,512,993 A | 5/1970 | Conley et al. |
| 3,537,871 A | 11/1970 | Kaneko et al. |
| 3,562,820 A | 2/1971 | Braun et al. |
| 3,656,881 A | 4/1972 | Hemwall |
| 3,728,207 A | 4/1973 | Heling et al. |
| 3,811,832 A | 5/1974 | Briggs |
| 3,873,478 A | 3/1975 | Comte et al. |
| 3,921,313 A | 11/1975 | Mahide et al. |
| 3,956,560 A | 5/1976 | Smith et al. |
| 3,979,532 A | 9/1976 | Muck et al. |
| 4,089,333 A | 5/1978 | Utsuo et al. |
| 4,215,051 A | 7/1980 | Schroeder et al. |
| 4,247,279 A | 1/1981 | Masters |
| 4,291,992 A | 9/1981 | Barr et al. |
| 4,294,241 A | 10/1981 | Miyata |
| 4,404,033 A | 9/1983 | Steffan |
| 4,407,956 A | 10/1983 | Howell |
| 4,455,206 A | 6/1984 | Funabashi et al. |
| 4,464,428 A | 8/1984 | Ebert et al. |
| 4,465,472 A | 8/1984 | Urbaniak |
| 4,532,929 A | 8/1985 | Mattei et al. |
| 4,536,475 A | 8/1985 | Anderson |
| 4,564,597 A | 1/1986 | Lerner et al. |
| 4,585,139 A | 4/1986 | Bronson et al. |
| 4,640,529 A | 2/1987 | Katz |
| 4,646,106 A | 2/1987 | Howkins |
| 4,665,492 A | 5/1987 | Masters |
| 4,673,304 A | 6/1987 | Liu et al. |
| 4,684,611 A | 8/1987 | Schilperoort et al. |
| 4,736,866 A | 4/1988 | Leder et al. |
| 4,772,141 A | 9/1988 | Sanders et al. |
| 4,842,575 A | 6/1989 | Hoffman et al. |
| 4,889,438 A | 12/1989 | Forsyth et al. |
| 4,896,980 A | 1/1990 | Sanders et al. |
| 4,921,365 A | 5/1990 | Sanders et al. |
| 4,931,546 A | 6/1990 | Tardy et al. |
| 4,945,050 A | 7/1990 | Sanford et al. |

(56) References Cited

U.S. PATENT DOCUMENTS

| | | |
|---|---|---|
| 4,948,280 A | 8/1990 | Sanders et al. |
| 4,969,758 A | 11/1990 | Sanders et al. |
| 4,970,168 A | 11/1990 | Tumer |
| 4,980,112 A | 12/1990 | Masters |
| 4,980,403 A | 12/1990 | Bateman et al. |
| 5,016,121 A | 5/1991 | Peddle et al. |
| 5,039,297 A | 8/1991 | Masters |
| 5,040,911 A | 8/1991 | Sanders et al. |
| 5,108,424 A | 4/1992 | Hoffman et al. |
| 5,134,178 A | 7/1992 | Nishibori |
| 5,134,569 A | 7/1992 | Masters |
| 5,153,067 A | 10/1992 | Yoshida et al. |
| 5,157,111 A | 10/1992 | Pachence |
| 5,171,273 A | 12/1992 | Silver et al. |
| 5,185,253 A | 2/1993 | Tumer |
| 5,201,745 A | 4/1993 | Tayot et al. |
| 5,204,055 A | 4/1993 | Sachs et al. |
| 5,216,606 A | 6/1993 | Lentz et al. |
| 5,229,112 A | 7/1993 | Obukowicz et al. |
| 5,304,730 A | 4/1994 | Lawson et al. |
| 5,349,124 A | 9/1994 | Fischhoff et al. |
| 5,362,865 A | 11/1994 | Austin |
| 5,378,619 A | 1/1995 | Rogers |
| 5,424,412 A | 6/1995 | Brown et al. |
| 5,487,992 A | 1/1996 | Capecchi et al. |
| 5,490,962 A | 2/1996 | Cima et al. |
| 5,492,937 A | 2/1996 | Bogentoft et al. |
| 5,495,071 A | 2/1996 | Fischhoff et al. |
| 5,503,999 A | 4/1996 | Jilka et al. |
| 5,510,253 A | 4/1996 | Mitsky et al. |
| 5,546,313 A | 8/1996 | Masters |
| 5,589,612 A | 12/1996 | Jilka et al. |
| 5,593,859 A | 1/1997 | Prockop et al. |
| 5,593,874 A | 1/1997 | Brown et al. |
| 5,599,695 A | 2/1997 | Pease et al. |
| 5,602,321 A | 2/1997 | John |
| 5,605,662 A | 2/1997 | Heller et al. |
| 5,614,396 A | 3/1997 | Bradley et al. |
| 5,627,061 A | 5/1997 | Barry et al. |
| 5,631,152 A | 5/1997 | Fry et al. |
| 5,633,435 A | 5/1997 | Barry et al. |
| 5,658,802 A | 8/1997 | Hayes et al. |
| 5,659,122 A | 8/1997 | Austin |
| 5,689,052 A | 11/1997 | Brown et al. |
| 5,697,324 A | 12/1997 | Van Der Lely |
| 5,702,717 A | 12/1997 | Cha et al. |
| 5,716,837 A | 2/1998 | Barry et al. |
| 5,739,832 A | 4/1998 | Heinzl et al. |
| 5,763,241 A | 6/1998 | Fischhoff et al. |
| 5,763,245 A | 6/1998 | Greenplate et al. |
| 5,792,933 A | 8/1998 | Ma |
| 5,797,898 A | 8/1998 | Santini, Jr. et al. |
| 5,798,779 A | 8/1998 | Nakayasu et al. |
| 5,804,425 A | 9/1998 | Barry et al. |
| 5,824,838 A | 10/1998 | Melmed et al. |
| 5,831,070 A | 11/1998 | Pease et al. |
| 5,859,347 A | 1/1999 | Brown et al. |
| 5,866,121 A | 2/1999 | Coffino et al. |
| 5,869,720 A | 2/1999 | Brown et al. |
| 5,929,208 A | 7/1999 | Heller et al. |
| 5,932,056 A | 8/1999 | Mark et al. |
| 5,932,439 A | 8/1999 | Bogosian |
| 5,945,319 A | 8/1999 | Keogh |
| 5,959,091 A | 9/1999 | Watrud et al. |
| 5,959,179 A | 9/1999 | Hinchee et al. |
| 5,981,841 A | 11/1999 | Santino et al. |
| 6,087,102 A | 7/2000 | Chenchik et al. |
| 6,103,528 A | 8/2000 | An et al. |
| 6,109,717 A | 8/2000 | Kane et al. |
| 6,123,861 A | 9/2000 | Santini, Jr. et al. |
| 6,132,468 A | 10/2000 | Mansmann |
| 6,139,831 A | 10/2000 | Shivashankar et al. |
| 6,171,797 B1 | 1/2001 | Perbost |
| 6,197,575 B1 | 3/2001 | Griffith et al. |
| 6,239,273 B1 | 5/2001 | Pease et al. |
| 6,261,493 B1 | 7/2001 | Gaylo et al. |
| 6,277,600 B1 | 8/2001 | Tomita et al. |
| 6,336,480 B2 | 1/2002 | Gaylo et al. |
| 6,365,650 B1 | 4/2002 | Chen et al. |
| 6,368,361 B1 | 4/2002 | Yayabe et al. |
| 6,383,549 B1 | 5/2002 | Agostinelli |
| 6,387,707 B1 | 5/2002 | Seul et al. |
| 6,394,585 B1 | 5/2002 | Ross |
| 6,402,403 B1 | 6/2002 | Speakman |
| 6,419,883 B1 | 7/2002 | Blanchard |
| 6,428,978 B1 | 8/2002 | Olsen et al. |
| 6,451,346 B1 | 9/2002 | Shah et al. |
| 6,454,811 B1 | 9/2002 | Sherwood et al. |
| 6,455,311 B1 | 9/2002 | Vacanti |
| 6,495,102 B1 | 12/2002 | Suslick et al. |
| 6,497,510 B1 | 12/2002 | Delametter et al. |
| 6,511,958 B1 | 1/2003 | Atkinson et al. |
| 6,514,518 B2 | 2/2003 | Monkhouse et al. |
| 6,517,648 B1 | 2/2003 | Bouchette et al. |
| 6,527,378 B2 | 3/2003 | Rausch et al. |
| 6,536,873 B1 | 3/2003 | Lee et al. |
| 6,536,895 B2 | 3/2003 | Kashiwagi et al. |
| 6,538,089 B1 | 3/2003 | Samra et al. |
| 6,543,872 B2 | 4/2003 | Ohtsuka et al. |
| 6,547,994 B1 | 4/2003 | Monkhouse et al. |
| 6,548,263 B1 | 4/2003 | Kapur et al. |
| 6,550,904 B2 | 4/2003 | Koitabashi et al. |
| 6,561,626 B1 | 5/2003 | Min et al. |
| 6,561,642 B2 | 5/2003 | Gonzalez |
| 6,565,176 B2 | 5/2003 | Anderson et al. |
| 6,596,304 B1 | 7/2003 | Bayon et al. |
| 6,708,531 B1 | 3/2004 | Thanikaivelan et al. |
| 6,733,859 B2 | 5/2004 | Yoneda et al. |
| 6,762,336 B1 | 7/2004 | MacPhee et al. |
| 6,800,384 B2 | 10/2004 | Suzuki et al. |
| 6,835,390 B1 | 12/2004 | Vein |
| 6,942,830 B2 | 9/2005 | Muelhaupt et al. |
| 6,979,670 B1 | 12/2005 | Lyngstadaas et al. |
| 7,004,978 B2 | 2/2006 | Kando et al. |
| 7,051,654 B2 | 5/2006 | Boland et al. |
| 7,056,845 B2 | 6/2006 | Waeber et al. |
| 7,166,464 B2 | 1/2007 | McAllister et al. |
| 7,270,829 B2 | 9/2007 | Van Eelen |
| 7,625,198 B2 | 12/2009 | Lipson et al. |
| 7,812,075 B2 | 10/2010 | Hong |
| 7,882,717 B2 | 2/2011 | Widdemer |
| 8,076,137 B2 | 12/2011 | McAllister et al. |
| 8,076,385 B2 | 12/2011 | Ohama |
| 8,153,176 B2 | 4/2012 | Etayo Garralda et al. |
| 8,188,230 B2 | 5/2012 | Van Heerde et al. |
| 8,328,878 B2 | 12/2012 | Zhang |
| 8,343,522 B2 | 1/2013 | Pohl et al. |
| 8,491,668 B2 | 7/2013 | Hinestroza et al. |
| 8,628,837 B2 | 1/2014 | Kusuura |
| 8,679,197 B2 | 3/2014 | Hinestroza et al. |
| 8,703,216 B2 | 4/2014 | Forgacs et al. |
| 8,741,415 B2 | 6/2014 | Kusuura |
| 8,785,195 B2 | 7/2014 | Takeuchi et al. |
| 8,916,263 B2 | 12/2014 | Kusuura |
| 9,023,619 B2 | 5/2015 | De Boer |
| 9,103,066 B2 | 8/2015 | Kusuura |
| 9,156,950 B2 | 10/2015 | Garralda et al. |
| 9,163,205 B2 | 10/2015 | Sivik et al. |
| 9,163,338 B2 | 10/2015 | Schauer et al. |
| 9,181,404 B2 | 11/2015 | Neresini et al. |
| 9,259,455 B2 | 2/2016 | Song et al. |
| 9,332,779 B2 | 5/2016 | Marga |
| 9,428,817 B2 | 8/2016 | Greene |
| 9,439,813 B2 | 9/2016 | Terada |
| 9,518,106 B2 | 12/2016 | Saeidi et al. |
| 9,539,363 B2 | 1/2017 | Shimp |
| 9,708,757 B2 | 7/2017 | Viladot Petit et al. |
| 9,733,393 B2 | 8/2017 | Liu et al. |
| 9,752,122 B2 | 9/2017 | Marga et al. |
| 9,821,089 B2 | 11/2017 | Haj-Ali et al. |
| 10,124,543 B1 | 11/2018 | Tymon et al. |
| 10,131,096 B1 | 11/2018 | Tymon et al. |
| 10,138,595 B1 | 11/2018 | Tymon |
| 10,259,191 B2 | 4/2019 | Wijesena et al. |

(56) References Cited

U.S. PATENT DOCUMENTS

| | | |
|---|---|---|
| 10,273,549 B2 | 4/2019 | Helgason et al. |
| 10,301,440 B2 | 5/2019 | Purcell et al. |
| 10,370,504 B2 | 8/2019 | Purcell et al. |
| 10,370,505 B2 | 8/2019 | Purcell et al. |
| 10,519,285 B2 | 12/2019 | Purcell et al. |
| 11,001,679 B2 | 5/2021 | Purcell et al. |
| 11,286,354 B2 | 3/2022 | Purcell et al. |
| 2002/0031500 A1 | 3/2002 | MacLaughlin et al. |
| 2002/0059049 A1 | 5/2002 | Bradbury et al. |
| 2002/0064808 A1 | 5/2002 | Mutz et al. |
| 2002/0064809 A1 | 5/2002 | Mutz et al. |
| 2002/0084290 A1 | 7/2002 | Materna |
| 2002/0089561 A1 | 7/2002 | Weitzel et al. |
| 2002/0090720 A1 | 7/2002 | Mutz et al. |
| 2002/0106412 A1 | 8/2002 | Rowe et al. |
| 2002/0142391 A1 | 10/2002 | Kivirikko et al. |
| 2002/0160109 A1 | 10/2002 | Yeo et al. |
| 2002/0164319 A1 | 11/2002 | Khaw et al. |
| 2002/0173586 A1 | 11/2002 | Jeong et al. |
| 2002/0182633 A1 | 12/2002 | Chen et al. |
| 2002/0188349 A1 | 12/2002 | McAllister et al. |
| 2003/0012805 A1 | 1/2003 | Chen et al. |
| 2003/0027332 A1 | 2/2003 | Lafrance et al. |
| 2003/0031500 A1 | 2/2003 | Bouveresse |
| 2003/0032203 A1 | 2/2003 | Sabatini et al. |
| 2003/0059537 A1 | 3/2003 | Chilkoti et al. |
| 2003/0100824 A1 | 5/2003 | Warren et al. |
| 2003/0113433 A1 | 6/2003 | Tempesta |
| 2003/0118560 A1 | 6/2003 | Kelly et al. |
| 2003/0129699 A1* | 7/2003 | Perret ................. A61L 26/0033 435/69.1 |
| 2003/0134120 A1 | 7/2003 | Kim et al. |
| 2003/0153078 A1 | 8/2003 | Libera et al. |
| 2003/0175410 A1 | 9/2003 | Campbell et al. |
| 2003/0190438 A1 | 10/2003 | Suzuki et al. |
| 2003/0207638 A1 | 11/2003 | Bowlin et al. |
| 2004/0005663 A1* | 1/2004 | Bell ....................... C07K 14/78 435/69.1 |
| 2004/0018226 A1* | 1/2004 | Wnek ...................... A61F 2/08 424/443 |
| 2004/0018592 A1 | 1/2004 | Bell et al. |
| 2004/0037813 A1* | 2/2004 | Simpson ................ A61L 27/34 424/93.7 |
| 2004/0039727 A1 | 2/2004 | Dessloch et al. |
| 2004/0046277 A1 | 3/2004 | Buerger et al. |
| 2004/0116032 A1 | 6/2004 | Bowlin et al. |
| 2004/0219133 A1 | 11/2004 | Lyles |
| 2004/0237208 A1* | 12/2004 | Day ......................... C14C 9/00 8/115.51 |
| 2005/0084719 A1* | 4/2005 | Yoshimoto ........... D06N 3/0004 422/105 |
| 2005/0118326 A1 | 6/2005 | Anfinsen et al. |
| 2005/0129730 A1 | 6/2005 | Pang et al. |
| 2005/0163912 A1 | 7/2005 | White |
| 2005/0202268 A1 | 9/2005 | Kotter et al. |
| 2005/0261427 A1 | 11/2005 | Saito |
| 2005/0276791 A1 | 12/2005 | Hansford et al. |
| 2006/0121006 A1 | 6/2006 | Chancellor et al. |
| 2006/0141479 A1 | 6/2006 | Song et al. |
| 2006/0270037 A1 | 11/2006 | Kato et al. |
| 2007/0088341 A1* | 4/2007 | Skiba ..................... A43B 1/0045 606/2 |
| 2007/0142916 A1 | 6/2007 | Olson et al. |
| 2007/0184742 A1 | 8/2007 | Coulson et al. |
| 2007/0231787 A1 | 10/2007 | Voelker |
| 2007/0238167 A1 | 10/2007 | Perez et al. |
| 2007/0292702 A1 | 12/2007 | Saumweber |
| 2008/0070304 A1 | 3/2008 | Forgacs et al. |
| 2008/0103287 A1 | 5/2008 | Chino et al. |
| 2008/0171994 A1 | 7/2008 | Williams et al. |
| 2008/0242822 A1 | 10/2008 | West |
| 2009/0005867 A1 | 1/2009 | Lefranc et al. |
| 2009/0041907 A1* | 2/2009 | Etayo Garralda ...... C08L 89/00 426/104 |
| 2009/0069893 A1 | 3/2009 | Paukshto et al. |
| 2009/0075382 A1 | 3/2009 | Sachlos |
| 2009/0142307 A1 | 6/2009 | Athanasiou et al. |
| 2009/0162896 A1* | 6/2009 | Scheibel ............ C07K 14/43504 435/69.1 |
| 2009/0208466 A1 | 8/2009 | Yoo et al. |
| 2009/0209823 A1 | 8/2009 | Yamane |
| 2009/0248145 A1 | 10/2009 | Chan et al. |
| 2010/0016872 A1 | 1/2010 | Bayon et al. |
| 2010/0041134 A1 | 2/2010 | Forgacs et al. |
| 2010/0087854 A1* | 4/2010 | Stopek ............... A61B 17/0057 606/215 |
| 2010/0189712 A1 | 7/2010 | L'Heureux et al. |
| 2010/0256314 A1 | 10/2010 | Marsden et al. |
| 2010/0325811 A1* | 12/2010 | Kashiwagura ............ C14C 3/04 8/94.24 |
| 2011/0151231 A1 | 6/2011 | Chomarat |
| 2011/0151563 A1 | 6/2011 | Paukshto et al. |
| 2011/0165301 A1 | 7/2011 | Blumenthal |
| 2011/0212179 A1 | 9/2011 | Liu |
| 2011/0212501 A1 | 9/2011 | Yoo |
| 2011/0250308 A1 | 10/2011 | Jun et al. |
| 2011/0288274 A1 | 11/2011 | Russell et al. |
| 2012/0010119 A1 | 1/2012 | Cunningham |
| 2012/0023777 A1 | 2/2012 | Greene |
| 2012/0040119 A1* | 2/2012 | Gagnieu ................ A61L 27/24 428/35.6 |
| 2012/0053689 A1* | 3/2012 | Martin .................. A61L 17/105 623/8 |
| 2012/0116053 A1* | 5/2012 | Mirochnitchenko .. C07K 14/78 530/350 |
| 2012/0116568 A1 | 5/2012 | Murphy et al. |
| 2012/0164200 A1 | 6/2012 | Qin et al. |
| 2012/0190473 A1 | 7/2012 | Swist |
| 2012/0230950 A1 | 9/2012 | Niklason et al. |
| 2012/0273993 A1* | 11/2012 | Shoseyov ............... A61L 27/24 264/202 |
| 2012/0276203 A1 | 11/2012 | Selim et al. |
| 2012/0316646 A1* | 12/2012 | Gretzer .................. A61L 27/24 623/16.11 |
| 2013/0029008 A1 | 1/2013 | Forgacs et al. |
| 2013/0131781 A1 | 5/2013 | Greenhalgh et al. |
| 2013/0142763 A1 | 6/2013 | Carlson et al. |
| 2013/0215598 A1 | 8/2013 | Guzan et al. |
| 2013/0255003 A1* | 10/2013 | Forgacs .................. C12P 21/00 8/94.2 |
| 2013/0256064 A1* | 10/2013 | Bongaerts ............... B01J 20/24 184/102 |
| 2013/0287896 A1 | 10/2013 | Harel et al. |
| 2013/0337711 A1 | 12/2013 | Wool |
| 2014/0005663 A1 | 1/2014 | Heard et al. |
| 2014/0017284 A1 | 1/2014 | Yang et al. |
| 2014/0021703 A1* | 1/2014 | Scharf ...................... B32B 7/00 280/728.3 |
| 2014/0093618 A1 | 4/2014 | Forgacs et al. |
| 2014/0193477 A1 | 7/2014 | Chaikof et al. |
| 2014/0205729 A1 | 7/2014 | Didzbalis et al. |
| 2014/0215850 A1 | 8/2014 | Redl et al. |
| 2014/0264079 A1 | 9/2014 | Tarahomi et al. |
| 2015/0013299 A1 | 1/2015 | Ramot |
| 2015/0079238 A1 | 3/2015 | Marga et al. |
| 2015/0216216 A1 | 8/2015 | Marga |
| 2015/0306276 A1* | 10/2015 | Shimp ................... A61L 27/24 424/422 |
| 2016/0097109 A1 | 4/2016 | Forgacs et al. |
| 2016/0097154 A1 | 4/2016 | Dumbrique et al. |
| 2016/0106674 A1* | 4/2016 | Scalesciani ......... A61L 26/0033 424/489 |
| 2016/0227831 A1 | 8/2016 | Marga |
| 2016/0250831 A1 | 9/2016 | Gladish et al. |
| 2016/0280960 A1 | 9/2016 | Leimer et al. |
| 2016/0287747 A1 | 10/2016 | Schallenberger |
| 2016/0348078 A1 | 12/2016 | Forgacs et al. |
| 2016/0376737 A1 | 12/2016 | Marga et al. |
| 2017/0152301 A1 | 6/2017 | Koob et al. |
| 2017/0233537 A1 | 8/2017 | Purcell et al. |
| 2017/0233836 A1 | 8/2017 | Jakab et al. |
| 2017/0233943 A1 | 8/2017 | Purcell et al. |

(56) References Cited

U.S. PATENT DOCUMENTS

| | | |
|---|---|---|
| 2017/0233945 A1 | 8/2017 | Purcell et al. |
| 2017/0298565 A1 | 10/2017 | Eryilmaz et al. |
| 2018/0084792 A1 | 3/2018 | Garcia et al. |
| 2018/0105659 A1 | 4/2018 | Hu et al. |
| 2018/0119318 A1 | 5/2018 | Morales |
| 2018/0230644 A1 | 8/2018 | Purcell et al. |
| 2018/0237592 A1 | 8/2018 | Celia |
| 2018/0371665 A1 | 12/2018 | Lin et al. |
| 2019/0024303 A1 | 1/2019 | Lee et al. |
| 2019/0032275 A1 | 1/2019 | Zhou et al. |
| 2019/0136060 A1 | 5/2019 | Helgason et al. |
| 2019/0144957 A1 | 5/2019 | Purcell et al. |
| 2019/0203000 A1 | 7/2019 | Purcell et al. |
| 2020/0199695 A1 | 6/2020 | Forgacs et al. |
| 2020/0207932 A1 | 7/2020 | Purcell et al. |
| 2020/0231805 A1 | 7/2020 | Teglia et al. |
| 2020/0370215 A1 | 11/2020 | Marga et al. |
| 2021/0023764 A1 | 1/2021 | Babin et al. |
| 2021/0300994 A1 | 9/2021 | Schachtschneider et al. |
| 2021/0355326 A1 | 11/2021 | Broadbent et al. |
| 2022/0106733 A1 | 4/2022 | Cai et al. |
| 2022/0127784 A1 | 4/2022 | Handlin, Jr. et al. |
| 2022/0153993 A1 | 5/2022 | Teglia et al. |

FOREIGN PATENT DOCUMENTS

| | | | |
|---|---|---|---|
| CN | 1305546 A | 7/2001 | |
| CN | 1488016 A | 4/2004 | |
| CN | 101946852 A | 1/2011 | |
| CN | 102016077 A | 4/2011 | |
| CN | 102105075 A | 6/2011 | |
| CN | 102906318 A | 1/2013 | |
| CN | 203021702 U | 6/2013 | |
| CN | 203021703 U | 6/2013 | |
| CN | 203021840 U | 6/2013 | |
| CN | 203021842 U | 6/2013 | |
| CN | 203021843 U | 6/2013 | |
| CN | 103231577 A | 8/2013 | |
| CN | 103233321 A | 8/2013 | |
| CN | 103233322 A | 8/2013 | |
| CN | 103233324 A | 8/2013 | |
| CN | 103233325 A | 8/2013 | |
| CN | 103233326 A | 8/2013 | |
| CN | 103255504 A | 8/2013 | |
| CN | 103255506 A | 8/2013 | |
| CN | 103255508 A | 8/2013 | |
| CN | 103255509 A | 8/2013 | |
| CN | 103255579 A | 8/2013 | |
| CN | 103255581 A | 8/2013 | |
| CN | 103255586 A | 8/2013 | |
| CN | 103256796 A | 8/2013 | |
| CN | 103264552 A | 8/2013 | |
| CN | 103266425 A | 8/2013 | |
| CN | 103276531 A | 9/2013 | |
| CN | 203174344 U | 9/2013 | |
| CN | 203174410 U | 9/2013 | |
| CN | 203174411 U | 9/2013 | |
| CN | 203174412 U | 9/2013 | |
| CN | 203174413 U | 9/2013 | |
| CN | 203174414 U | 9/2013 | |
| CN | 203174415 U | 9/2013 | |
| CN | 203174416 U | 9/2013 | |
| CN | 203174417 U | 9/2013 | |
| CN | 203174418 U | 9/2013 | |
| CN | 203174419 U | 9/2013 | |
| CN | 203291935 U | 11/2013 | |
| CN | 203295678 U | 11/2013 | |
| CN | 203295679 U | 11/2013 | |
| CN | 203295689 U | 11/2013 | |
| CN | 203295690 U | 11/2013 | |
| CN | 203295794 U | 11/2013 | |
| CN | 203295796 U | 11/2013 | |
| CN | 203298579 U | 11/2013 | |
| CN | 203307577 U | 11/2013 | |
| CN | 104233778 A | 12/2014 | |
| CN | 102995165 B | 1/2015 | |
| CN | 103252276 B | 1/2015 | |
| CN | 204112009 U | 1/2015 | |
| CN | 204112011 U | 1/2015 | |
| CN | 103014924 B | 2/2015 | |
| CN | 103231576 B | 4/2015 | |
| CN | 103255653 B | 4/2015 | |
| CN | 104603293 A | 5/2015 | |
| CN | 104695205 A | 6/2015 | |
| CN | 105102711 A | 11/2015 | |
| CN | 205347859 U | 6/2016 | |
| CN | 205361168 U | 7/2016 | |
| CN | 106987931 A | 7/2017 | |
| CN | 108660607 A | 10/2018 | |
| EP | 0 067 553 A2 | 12/1982 | |
| EP | 0078040 A2 | 5/1983 | |
| EP | 0 089 029 A2 | 9/1983 | |
| EP | 0388854 A2 | 9/1990 | |
| EP | 0421450 A2 * | 4/1991 | ............ C08L 89/06 |
| EP | 0 426 641 A2 | 5/1991 | |
| EP | 0470399 A2 | 2/1992 | |
| EP | 0 531 273 A2 | 3/1993 | |
| EP | 0 578 627 A1 | 1/1994 | |
| EP | 0 388 854 B1 | 11/1994 | |
| EP | 0 709 462 A2 | 5/1996 | |
| EP | 1319415 A1 | 6/2003 | |
| EP | 1 589 091 A1 | 10/2005 | |
| EP | 1589098 A1 | 10/2005 | |
| EP | 1 232 182 B1 | 10/2007 | |
| EP | 2 003 239 A1 | 12/2008 | |
| EP | 2090584 A1 | 8/2009 | |
| EP | 2 319 337 A1 | 5/2011 | |
| EP | 2 148 887 B1 | 4/2014 | |
| EP | 2148887 B1 | 4/2014 | |
| EP | 2721941 A1 | 4/2014 | |
| EP | 3205668 A1 | 8/2017 | |
| FR | 2188610 A5 | 1/1974 | |
| GB | 723214 A | 2/1955 | |
| GB | 723215 A | 2/1955 | |
| GB | 992585 A | 5/1965 | |
| GB | 1 024 769 A | 4/1966 | |
| GB | 1367490 A | 9/1974 | |
| JP | S5819331 A | 2/1983 | |
| JP | S58146345 A | 8/1983 | |
| JP | S60203264 A | 10/1985 | |
| JP | H04146273 A | 5/1992 | |
| JP | H05184661 A | 7/1993 | |
| JP | H05279966 A | 10/1993 | |
| JP | 6017378 A | 1/1994 | |
| JP | H06158546 A | 6/1994 | |
| JP | H06198800 A | 7/1994 | |
| JP | H0770600 A | 3/1995 | |
| JP | 9047502 A | 2/1997 | |
| JP | 3184405 U | 6/2013 | |
| JP | 2014504264 A | 2/2014 | |
| KR | 100716015 B1 | 5/2007 | |
| WO | WO-8303224 A1 | 9/1983 | |
| WO | 91/19806 A1 | 12/1991 | |
| WO | WO-9412563 A1 | 6/1994 | |
| WO | WO 96/01912 | 1/1996 | |
| WO | 97/17459 A1 | 5/1997 | |
| WO | 97/30582 A1 | 8/1997 | |
| WO | 97/48814 A2 | 12/1997 | |
| WO | 98/08962 A1 | 3/1998 | |
| WO | 98/31812 A1 | 7/1998 | |
| WO | 98/45457 A1 | 10/1998 | |
| WO | 98/58069 A1 | 12/1998 | |
| WO | 99/07206 A1 | 2/1999 | |
| WO | 99/16890 A2 | 4/1999 | |
| WO | 99/31248 A1 | 6/1999 | |
| WO | WO-9931222 A1 | 6/1999 | |
| WO | WO-9931223 A1 | 6/1999 | |
| WO | 99/40210 A1 | 8/1999 | |
| WO | WO-0160922 A1 * | 8/2001 | ............ A61K 8/65 |
| WO | WO-0168811 A2 | 9/2001 | |
| WO | WO-2005081970 A2 | 9/2005 | |
| WO | WO-2007124023 A2 | 11/2007 | |
| WO | WO-2009066635 A1 | 5/2009 | |
| WO | WO-2009070720 A1 | 6/2009 | |

(56) References Cited

FOREIGN PATENT DOCUMENTS

| WO | 2009/149181 A2 | 12/2009 |
|---|---|---|
| WO | WO-2010008905 A2 | 1/2010 |
| WO | 2010/021738 A2 | 2/2010 |
| WO | 2010/048281 A1 | 4/2010 |
| WO | WO-2010091251 A2 | 8/2010 |
| WO | WO-2011051983 A1 | 5/2011 |
| WO | WO-2012054195 A2 | 4/2012 |
| WO | WO-2012108907 A1 | 8/2012 |
| WO | WO-2013039118 A1 | 3/2013 |
| WO | 2013/149083 A1 | 10/2013 |
| WO | WO-2014039938 A1 | 3/2014 |
| WO | WO-2014195426 A1 | 12/2014 |
| WO | WO-2014201406 A1 | 12/2014 |
| WO | WO-2016073453 A1 | 5/2016 |
| WO | 2017/053433 A1 | 3/2017 |
| WO | WO-2017131196 A1 | 8/2017 |
| WO | WO-2017142890 A1 | 8/2017 |
| WO | WO-2017142892 A1 | 8/2017 |
| WO | WO-2018058874 A1 | 4/2018 |
| WO | WO-2018110819 A1 | 6/2018 |
| WO | WO-2018137041 A1 | 8/2018 |
| WO | WO-2019017987 A1 | 1/2019 |

OTHER PUBLICATIONS

Li, Mengyan et al. Electrospun Protein Fibers as Matrices for Tissue Engineering, Biomaterials 26, 2005, p. 5999-6008.*
Isolate, Definition of. Merriam-Webster, http://merriam-webster.com/dictionary/isolate, retrieved Dec. 22, 2017.*
Purify, Definition of. Merriam-Webster, http://merriam-webster.com/dictionary/purify, retrieved Dec. 22, 2017.*
Harris, JR, A Soliakov, and RJ Lewis, In vitro Fibrillogenesis of Collagen Type I in Varying Ionic and pH Conditions, Micron, Jun. 2013 49:60-68.*
Li, Zheng, Denis Paudecerf, and Jiashi Yang, Mechnical Behaviour of Natural Cow Leather in Tension, Acta Mechanica Solida Sinica, vol. 22, No. 1, Feb. 2009.*
Wells, Hannah, etl. al., Collagen Fibril Diamter and Leather Strength, Journal of Agricultural and Food Chemistry, 2013, 61, 11524-11531.*
Abedin et al., "Isolation and native characterization of cysteine-rich collagens from bovine placental tissues and uterus and their relationship to types IV and V collagens", Bioscience Reports, vol. 2, Issue 7, Jul. 1982, pp. 493-502.
Apte et al., "Cloning of the human and mouse type X collagen genes and mapping of the mouse type X collagen gene to chromosome 10", Eur. J. Biochem., vol. 206, 1992, pp. 217-224.
Aubert-Foucher et al., "Purification and Characterization of Native Type XIV Collagen", The Journal of Biological Chemistry, vol. 267, No. 22, Aug. 1992, pp. 15759-15764.
Ayad et al., "Bovine cartilage types VI and IX collagens", Biochem. J., 262, 1989, pp. 753-761.
Bailey et al., "Irradiation-Induced Crosslinking of Collagen", Radiation Research, vol. 22, No. 4, Aug. 1964, pp. 606-621.
Basil-Jones et al., "Collagen Fibril Orientation in Ovine and Bovine Leather Affects Strength: A Small Angle X-ray Scattering (SAXS) Study", Journal of Agricultural and Food Chemistry, vol. 59, 2011, pp. 9972-9979.
Bentz et al., "Isolation and partial characterization of a new human collagen with an extended triple-helical structural domain", Proc. Natl. Acad. Sci. USA, vol. 80, Jun. 1983, pp. 3168-3172.
Benya et al., "Isolation and Characterization of Type VIII Collagen Synthesized by Cultured Rabbit Corneal Endothelial Cells", The Journal of Biological Chemistry, vol. 261, No. 9, Mar. 1986, pp. 4160-4169.
Berger et al., "Expression in transgenic plants of a viral gene product that mediates insect transmission of potyviruses", Proc. Natl. Acad. Sci USA, vol. 86, Nov. 1989, pp. 8402-8406.

Bevan et al., "The structure and transcription start site of a major potato tuber protein gene", Nucleic Acids Research, vol. 14, No. 11, 1986, pp. 4625-4638.
Bitter, G., "[70] Heterologous Gene Expression in Yeast", Methods in Enzymology, vol. 152, 1987, pp. 673-684.
Bray et al., "Expression of the β-subunit of β-conglycinin in seeds of transgenic plants", Planta, vol. 172, 1987, pp. 364-370.
Broglie et al., "Light-Regulated Expression of a Pea Ribulose-1,5-Bisphosphate Carboxylase Small Subunit Gene in Transformed Plant Cells", Science, vol. 224, May 1984, pp. 838-843.
Burgeson, "Collagen types: Molecular Structure and Tissue Distribution", Clinical Orthopaedics and Related Research, No. 282, Sep. 1992, pp. 250-272.
Byers et al., "Preparation of Type III Procollagen and Collagen from Rat Skin", Biochemistry, vol. 13, No. 25, 1974, pp. 5243-5248.
Casas et al., "Transgenic sorghum plants via microprojectile bombardment", Proc. Natl. Acad. Sci. USA, vol. 90, Dec. 1993, pp. 11212-11216.
Christensen, et al., "Maize polyubiquitin genes: structure, thermal perturbation of expression and transcript splicing, and promoter activity following transfer to protoplasts by electroporation", Plant Molecular Biology, 18(4), Feb. 1992, pp. 675-689.
Christou et al., "The development of a variety-independent gene-transfer method for rice", Tibtech, vol. 10, Jul. 1992, pp. 239-246.
Coruzzi et al., "Tissue specific and light regulated expression of a pea nuclear gene encoding small subunit of ribulose 1-5 biphosphate carboxylase", The EMBO Journal, vol. 3, No. 8, Sep. 1984, pp. 1671-1679.
Duance et al., "Isolation and characterization of the precursor of type M collagen", Biochem. J., vol. 221, 1984, pp. 885-889.
Dublet et al., "The Structure of Avian Type XII Collagen", The Journal of Biological Chemistry, vol. 264, No. 22, Aug. 1989, pp. 13150-13156.
Elstow et al., "Extraction, Isolation and Characterization of Neutral Salt Soluble Type V Collagen from Fetal Calf Skin", Collagen Rel. Res., vol. 3, 1983, pp. 181-193.
Fromm et al., "Inheritance and Expression of Chimeric Genes in the Progeny of Transgenic Maize Plants", Bio/Technology, vol. 8, Sep. 1990, pp. 833-839.
"Future Trends in the World Leather Products Industry and Trade", United Nation Industrial Development Organization, Vienna, 2010.
Gordon et al., "Discovery of a New Collagen, Type XX, Present in Chick Cornea", IOVS, vol. 39, No. 4, Mar. 1998, S1128 (Abstract only).
Gordon et al., "Type XX Collagen, A New Member of the Fibril-Associated (FACIT) Family of Collagens", The FASEB Journal, vol. 13, No. 5, Mar. 1999, A1119 (829.6).
Gurley et al., "Upstream Sequences Required for Efficient Expression of a Soybean Heat Shock Gene", Molecular and Cellular Biology, vol. 6, No. 2, Feb. 1986, pp. 559-565.
Hinchee et al., "Production of Transgenic Soybean Plants Using Agrobacterium-Mediated DNA Transfer", Bio/Technology, vol. 6, Aug. 1988, pp. 915-922.
Housley et al., "Collagen Crosslinking: Isolation of Hydroxyaldol-Histidine, a Naturally-Occurring Crosslink", Biochemical and Biophysical Research Communications, vol. 67, No. 2, 1975, pp. 824-830.
Hueber et al., "Chromosomal Assignment of a Gene Encoding a New Collagen Type (COL15A1) to 9q21 → q22", Genomics 14, 1992, pp. 220-224.
Inoguchi et al., "The mRNA for α1 (XIX) Collagen Chain, a New Member of FACITs, Contains a Long Unusual 3' Untranslated Region and Displays Many Unique Splicing Variants", J. Biochem., vol. 117, No. 1, 1995, pp. 137-146.
Inouye et al., "Up-promoter mutations in the lpp gene of *Escherichia coli*", Nucleic Acids Research, vol. 13, No. 9, 1985, pp. 3101-3110.
Juvonen et al., "Patterns of Expression of the Six Alternatively Spliced Exons Affecting the Structures of the COL1 and NC2 Domains of the α1(XIII) Collagen Chain in Human Tissues and Cell Lines", The Journal of Biological Chemistry, vol. 267, No. 34, Dec. 1992, pp. 24700-24707.

(56) References Cited

OTHER PUBLICATIONS

Kapoor et al., "Type VIII Collagen from Bovine Descemet's Membrane: Structural Characterization of a Triple-Helical Domain", Biochemistry, vol. 25, No. 13, 1986, pp. 3930-3937.
Kay et al., "Duplication of CaMV 35S Promoter Sequences Creates a Strong Enhancer for Plant Genes", Science, vol. 236, Jun. 1987, pp. 1299-1302.
Kielty et al., "Isolation and ultrastructural analysis of microfibrillar structures from foetal bovine elastic tissues", Journal of Cell Science, vol. 99, 1991, pp. 797-807.
Kielty et al., "The Collagen Family: Structure, Assembly and Organization in the Extracellular Matrix", Connective Tissue and Its Heritable Disorders: Molecular, Genetic, and Medical Aspects, 2002, pp. 159-221.
Kivirikko et al., "Primary Structure of the α1 Chain of Human Type XV Collagen and Exon-Intron Organization of the 3' Region of the Corresponding Gene", The Journal of Biological Chemistry, vol. 269, No. 7, Feb. 1994, pp. 4773-4779.
Lee et al., "Efficient transformation and regeneration of rice small cell groups", Proc. Natl. Acad. Sci. USA, vol. 88, Aug. 1991, pp. 6389-6393.
Li et al., "Cloning of Type XVII Collagen", The Journal of Biological Chemistry, vol. 268, No. 12, Apr. 1993, pp. 8825-8834.
Logan et al., "Adenovirus tripartite leader sequence enhances translation of mRNAs late after infection", Proc. Natl. Acad. Sci. USA, vol. 81, Jun. 1984, pp. 3655-3659.
Luckow et al., "High Level Expression of Nonfused Foreign Genes with *Autographa californica* Nuclear Polyhedrosis Virus Expression Vectors", Virology, vol. 170, Issue 1, May 1989, pp. 31-39.
Lunstrum et al., "Identification and Partial Purification of a Large, Variant Form of Type XII Collagen", The Journal of Biological Chemistry, vol. 267, No. 28, Oct. 1992, pp. 20087-20092.
Lunstrum et al., "Large Complex Globular Domains of Type VII Procollagen Contribute to the Structure of Anchoring Fibrils", The Journal of Biological Chemistry, vol. 261, No. 19, Jul. 1986, pp. 9042-9048.
Mackett et al., "General Method for Production and Selection of Infectious Vaccinia Virus Recombinants Expressing Foreign Genes", Journal of Virology, vol. 49, No. 3, Mar. 1984, pp. 857-864.
Mackett et al., "Vaccinia virus: A selectable eukaryotic cloning and expression vector", Proc. Nat. Acad. Sci. USA, vol. 79, Dec. 1982, pp. 7415-7419.
McElroy et al., "Isolation of an Efficient Actin Promoter for Use in Rice Transformation", The Plant Cell, vol. 2, Feb. 1990, pp. 163-171.
McGrath et al., "Mutations in the 180-kD bullous pemphigoid antigen (BPAG2), a hemidesmosomal transmembrane collagen (COL17A1), in generalized atrophic benign epidermolysis bullosa", Nature Genetics, vol. 11, Sep. 1995, pp. 83-86.
Mechanic et al., "Biochemistry of Collagen Crosslinking Isolation of a new Crosslink, Hydroxylysinohydroxynorleucine, and Its Reduced Precursor, Dihydroxynorleucine, from Bovine Tendon", Biochemical and Biophysical Research Communications, vol. 41, No. 6, 1970, pp. 1597-1604.
Mechanic et al., "The Nature of Crosslinking in Collagens from Mineralized Tissues", Biochemical and Biophysical Research Communications, vol. 45, No. 3, 1971, pp. 644-653.
Medberry et al., "The Commelina Yellow Mottle Virus Promoter Is a Strong Promoter in Vascular and Reproductive Tissues", The Plant Cell, vol. 4, Feb. 1992, pp. 185-192.
Miller et al., "[2] Preparation and Characterization of the Different Types of Collagen", Methods in Enzymology, vol. 82, 1982, pp. 33-64.
Muller-Rober et al., "One of two different ADP-glucose pyrophosphorylase genes from potato responds strongly to elevated levels of sucrose", Mol. Gen. Genet, vol. 224, 1990, pp. 136-146.
Muragaki et al., "The Human α1(XV) Collagen Chain Contains a Large Amino-terminal Non-triple Helical Domain with a Tandem Repeat Structure and Homology to α1(XVIII) Collagen", The Journal of Biological Chemistry, vol. 269, No. 6, Feb. 1994, pp. 4042-4046.
Myers et al., "Identification of a previously unknown human collagen chain, α1(XV), characterized by extensive interruptions in the triple-helical region", Proc. Natl. Acad. Sci. USA, vol. 89, Nov. 1992, pp. 10144-10148.
Myers et al., "The Triple-helical Region of Human Type XIX Collagen Consists of Multiple Collagenous Subdomains and Exhibits Limited Sequence Homology to α1(XVI)", The Journal of Biological Chemistry, vol. 269, No. 28, Jul. 1994, pp. 18549-18557.
Oh et al., "Cloning of cDNA and Genomic DNA Encoding Human Type XVIII Collagen and Localization of the α1(XVIII) Collagen Gene to Mouse Chromosome 10 and Human Chromosome 21", Genomics, vol. 19, 1994, pp. 494-499.
Oh et al., "Isolation and sequencing of cDNAs for proteins with multiple domains of Gly-Xaa-Yaa repeats identify a distinct family of collagenous proteins", Proc. Natl. Acad. Sci. USA, vol. 91, May 1994, pp. 4229-4233.
Olkkonen et al., "Expression of Exogenous Proteins in Mammalian Cells with the Semliki Forest Virus Vector", Methods in Cell Biology, vol. 43, 1994, pp. 43-53.
Pan et al., "Cloning and chromosomal location of human α1(XVI) collagen", Proc. Natl. Acad. Sci. USA, vol. 89, Jul. 1992, pp. 6565-6569.
Panicali et al., "Construction of poxviruses as cloning vectors: Insertion of the thymidine kinase gene from herpes simplex virus into the DNA of infectious vaccinia virus", Proc. Natl. Acad. Sci. USA, vol. 79, Aug. 1982, pp. 4927-4931.
Paszkowski et al., "Direct gene transfer to Plant", The EMBO Journal, vol. 3, No. 12, 1984, pp. 2717-2722.
Pedersen et al., "Cloning and Sequence Analysis Reveal Structural Variation among Related Zein Genes in Maize", Cell, vol. 29, Jul. 1982, pp. 1015-1026.
Prockop et al., "Collagens: Molecular Biology, Diseases, and Potentials for Therapy", Annu. Rev. Biochem., vol. 64, 1995, pp. 403-434.
Rehn et al., "Primary Structure of the α1 Chain of Mouse Type XVIII Collagen, Partial Structure of the Corresponding Gene, and Comparison of the α1(XVIII) Chain with Its Homologue, the α1(XV) Collagen Chain", The Journal of Biological Chemistry, vol. 269, No. 19, May 1994, pp. 13929-13935.
Rehn et al., "α1 (XVIII), a collagen chain with frequent interruptions in the collagenous sequence, a distinct tissue distribution, and homology with type XV collagen", Proc Natl. Acad. Sci. USA, vol. 91, May 1994, pp. 4234-4238.
Riggs et al., "Stable transformation of tobacco by electroporation: Evidence for plasmid concatenation", Proc. Natl. Acad. Sci. USA, vol. 83, Aug. 1986, pp. 5602-5606.
Rogers, "Two Barley α-Amylase Gene Families are Regulated Differently in Aleurone Cells", The Journal of Biological Chemistry, vol. 260, No. 6, Mar. 1985, pp. 3731-3738.
Rogers et al., "Improved Vectors for Plant Transformation: Expression Cassette Vectors and New Selectable Markers", Methods in Enzymology, vol. 153, 1987, pp. 253-277.
Ruther et al., "Easy identification of cDNA clones", The EMBO Journal, vol. 2, No. 10, 1983, pp. 1791-1794.
Sanger et al., "Characteristics of a strong promoter from figwort mosaic virus: comparison with the analogous 35S promoter from cauliflower mosaic virus and the regulated mannopine synthase promoter", Plant Molecular Biology, vol. 14, 1990, pp. 433-443.
Schardl et al., "Design and construction of a versatile system for the expression of foreign genes in plants", Gene, vol. 61, 1987, pp. 1-11.
Schmitt et al., "Electron Microscope Investigations of the Structure of Collagen", Journal of Cellular Physiology, vol. 20, Issue 1, Aug. 1942, pp. 11-33.
Shosan et al., "Studies on Collagen Crosslinking in vivo", Biochim. Biophys. Acta, vol. 154, 1968, pp. 261-263.
Siegel, "Biosynthesis of Collagen Crosslinks: Increased Activity of Purified Lysyl Oxidase with Reconstituted Collagen Fibrils", Proc. Nat. Acad. Sci. USA, vol. 71, No. 12, Dec. 1974, pp. 4826-4830.

(56) References Cited

OTHER PUBLICATIONS

Silva et al., "Marine Origin Collagens and Its Potential Applications", Marine Drugs, vol. 12, 2014, pp. 5881-5901.
Sizeland et al., "Collagen Orientation and Leather Strength for Selected Mammals", Journal of Agricultural and Food Chemistry, 61, 2013, pp. 887-892.
Smith et al., "Molecular Engineering of the *Autographa californica* Nuclear Polyhedrosis Virus Genome: Deletion Mutations Within the Polyhedrin Gene", Journal of Virology, vol. 46, No. 2, May 1983, pp. 584-593.
Takamatsu et al., "Expression of bacterial chloramphenicol acetyltransferase gene in tobacco plants mediated by TMV-RNA", The EMBO Journal, vol. 6, No. 2, 1987, pp. 307-311.
Van Heeke et al., "Expression of Human Asparagine Synthetase in *Escherichia coli*", The Journal of Biological Chemistry, vol. 264, No. 10, Apr. 1989, pp. 5503-5509.
Wan et al., "Generation of Large Numbers of Independently Transformed Fertile Barley Plants", Plant Physiol., vol. 104, 1994, pp. 37-48.
Watt et al., "Characterization of Collagen Types XII and XIV from Fetal Bovine Cartilage", The Journal of Biological Chemistry, vol. 267, No. 28, Oct. 1992, pp. 20093-20099.
Wu et al., "Type VI collagen of the intervertebral disc", Biochem. J., vol. 248, 1987, pp. 373-381.
Yamaguchi et al., "Molecular Cloning and Partial Characterization of a Novel Collagen Chain, α1(XVI), Consisting of Repetitive Collagenous Domains and Cysteine-Containing Non-Collagenous Segments", J. Biochem., vol. 112, 1992, pp. 856-863.
Yin et al., "The regulatory regions of the rice tungro bacilliform virus promoter and interacting nuclear factors in rice (*Oryza sativa* L.)", The Plant Journal, vol. 7, No. 6, 1995, pp. 969-980.
Yoshioka et al., "Synteny between the Loci for a Novel FACIT-like Collagen Locus (D6S228E) and α1(IX) Collagen (COL9A1) on 6q12-q14 in Humans", Genomics 13, 1992, pp. 884-886.
International Search Report & Written Opinion dated May 5, 2017 in corr. International Application No. PCT/US2017/17889, filed Feb. 15, 2017.
Extended European Search Report dated Jul. 17, 2017 in corr. European Application No. 17156361.2, filed Feb. 15, 2017.
Shayegan et al., "Microrheological Characterization of Collagen Systems: From Molecular Solutions to Fibrillar Gels", Plos One, vol. 8,Issue 8, Aug. 2013, pp. 1-12.
Wells et al., "Collagen Fibril Diameter and Leather Strength", Journal of Agricultural and Food Chemistry, vol. 61, 2013, pp. 11524-11531.
Extended European Search Report dated Jul. 17, 2017 in corr. European Application No. 17156362.0, filed Feb. 15, 2017.
Extended European Search Report dated Jul. 18, 2017 in corr. European Application No. 17156363.8, filed Feb. 15, 2017.
Database WPI, Week 199427, Thomson Scientific, London, GB, 1994—AN 1994-222702.
International Search Report & Written Opinion dated Apr. 25, 2017 in corr. International Application No. PCT/US2017/17878, filed Feb. 15, 2017.
Extended European Search Report dated Jul. 18, 2017 in corresponding EP Patent Application No. 17156365.3, Feb. 15, 2017.
International Search Report & Written Opinion dated Apr. 25, 2017 in corr. International Application No. PCT/US2017/17872, filed Feb. 15, 2017.
Chua, J., "Grow Your Own Microbial 'Leather' in Your Kitchen (DIY Tutorial)", Ecouterre, Feb. 23, 2015 [online] [Retrieved on Sep. 1, 2017] Retrieved from the Internet <URL: www.ecouterre.com/grow-your-own-microbial-leather-in your-kitchen-diy-tutorial>.
Wu et al., "Quantitative analysis on collagen morphology in aging skin based on multiphoton microscopy", Journal of Biomedical Optics, vol. 16(4), Apr. 2011, pp. 040502-1-040502-3.
International Search Report & Written Opinion dated May 19, 2017 in corr. International Application No. PCT/US2017/17867, filed Feb. 15, 2017.

Brisson et al., "Plant Virus Vectors: Cauliflower Mosaic Virus", Methods for Plant Molecular Biology, New York: Academic Press, 1988, pp. 437-446.
Cornejo et al., "Activity of a maize ubiquitin promoter in transgenic rice", Plant Molecular Biology, vol. 23, Issue 3, Nov. 1993, pp. 567-581.
Aldhous, Print me a heart and a set of arteries, New Scientist, Apr. 15, 2006, retrieved from the internet on Jun. 3, 2015. Retrieved from the Internet: (http://organprint.missouri.edu/www/news/NewScientistApril2006.pdf).
Arding, Vegetarian cheese, Culture the word on cheese, 2 pgs, Dec. 3, 2013, retrieved from the internet on Oct. 31, 2014. Retrieved from the Internet: (URL: https://culturecheesemag.com/ask-the-monger/vegetarian-cheese).
Barnard, N.D., et al., "The Medical Costs Attributable to Meat Consumption," Preventive Medicine, 24(6):646-655, Academic Press, Inc (Nov. 1995).
Benjaminson, M.A., et al., "In Vitro Edible Muscle Protein Production System (MPPS): Stage 1, Fish," Acta Astronautica, 51(12):879-889, Pergamon Press, England(Dec. 2002).
Bhat, Z.F and Bhat, H., "Animal-free Meat Biofabrication," American Journal of Food Technology, 6(6):441-459, (Jun. 2011).
Bhat, Z.F and Bhat, H., "Tissue Engineered Meat—Future Meat," Journal of Stored Products and Postharvest Research, 2(1):1-10, (Jan. 2011).
Bian, W. and Bursac, N.,, "Engineered Skeletal Muscle Tissue Networks With Controllable Architecture," Biomaterials, 30(7):1401-1412, IPC Science and Technology Press, Netherlands, (Mar. 2009).
Boonen, K.J and Post, M.J., "The Muscle Stem Cell Niche: Regulation of Satellite Cells During Regeneration," Tissue Engineering Part B, 14(4):419-431, Mary Ann Liebert, Inc, United States (Dec. 2008).
Boonen K.J.M., et al., "Essential Environmental Cues From the Satellite Cell Niche: Optimizing Proliferation and Differentiation," American Journal of Physiology—Cell Physiology, 296(6):C1338-C1345, (Jun. 2009).
Chang, L.C., et al., "Comparalive Study of Physical Properties of Water-Blown Rigid Polyurethane Foams Extended With Commercial Soy Flour", Journal of Applied Polymer Science 80:10-19, John Wiley & Sons, Inc (2001).
Chen, Y., et al., "Structure and Properties of Composites Compression-Molded from Polyurethane Prepolymer and Various Soy Products", Industrial & Engineering Chemistry Research, 42(26):6786-6794, American Chemical Society (Dec. 2003).
Co-Pending U.S. Appl. No. 16/724,689, filed Dec. 12, 2019, inventors Lee; S., et al., (Unpublished).
Datar, I and Betti, M., "Possibilities for an in Vitro Meat Production System," Innovative Food Science and Emerging Technologies, 11(1):13-22, Elsevier Ltd(Jan. 2010).
De-Deyne, P.G., "Formation of Sarcomeres in Developing Myotubes: Role of Mechanical Stretch and Contractile Activation," American Journal of Physiology—Cell Physiology, 279(6):C1801-C1811, (Dec. 2000).
Dennis, R.G and Kosnik, P.E 2nd., "Excitability and Isometric Contractile Properties of Mammalian Skeletal Muscle Constructs Engineered in Vitro," In Vitro Cellular & Developmental Biology, 36(5):327-335, Springer, Germany (May 2000).
Dennis, R.G., et al., "Excitability and Contractility of Skeletal Muscle Engineered From Primary Cultures and Cell Lines," American Journal of Physiology—Cell Physiology, 280(2):C288-C295, American Physiological Society, United States (Feb. 2001).
Edelman, E.R., "Vascular Tissue Engineering: Designer Arteries," Circulation Research 85(12):1115-1117, Lippincott Williams & Wilkins, United States (Dec. 1999).
Edelman, P.D., et al., "Commentary: in Vitro-cultured Meat Production," Tissue Engineering, 11(5-6):659-662, Mary Ann Liebert, Inc, United States (May-Jun. 2005).
Engler, A. J., et al., "Myotubes Differentiate Optimally on Substrates With Tissue-like Stiffness: Pathological Implications for Soft or Stiff Microenvironments," Journal of Cell Biology, 166(6):877-887, Rockefeller University Press, United States (Sep. 2004).
European Food Safety Authority, The Community Summary Report on Trends and Sources of Zoonoses, Zoonotic Agents, Antimicro-

(56) References Cited

OTHER PUBLICATIONS bial Resistance and Food borne Outbreaks in the European Union in 2005, EFSA J, May 2007, 94, 2-288.
Filler, Definition of Filler by Merriam-Webster, Retrieved from the Internet [Aug. 19, 2018], Retrieved from the Internet (URL: http://www.merriam-webster.com/dictionary/filler).
Fonseca, S., et al., "Slow Fiber Cluster Pattern in Pig Longissimus Thoracic Muscle: Implications for Myogenesis," Journal of Animal Science, 81(4):973-983, American Society of Animal Science, United States (Apr. 2003).
Gawlitta, D., et al., "The Influence of Serum-free Culture Conditions on Skeletal Muscle Differentiation in a Tissue-engineered Model," Tissue Engineering Part A, 14(1):161-171, (Jan. 2008).
Halim, A,S., et al., "Biologic and Synthetic Skin Substitutes: An Overview," Indian Journal of Plastic Surgery 43(Suppl): S23-S28, Thieme, Germany (Sep. 2010).
Hopkins, P.D and Dacey, A., A vegetarian meat: could technology save animals and satisfy meat eaters?, Journal of Agricultural and Environmental Ethics, 21(6):579-596, Springer, 2008, retrieved from the internet on Jun. 2, 2015 (http://foodethics.univie.ac.at/fileadmin/user.sub.--upload/inst.sub.--et-hik.sub.--wiss.sub.--dialog/Hopkins.sub.--P..sub.--2008.sub.--Veg.sub.--Me-at.sub.-and.sub.-In.sub.--Meat.pdf).
Jakab, K., et al., "Engineering Biological Structures of Prescribed Shape Using Self-assembling Multicellular Systems," Proceedings of the National Academy of Sciences of the United States of America 101(9):2864-2869, National Academy of Sciences, United States (Mar. 2004).
Jakab, K., et al., "Tissue Engineering by Self-assembly and Bioprinting of Living Cells," Biofabrication 2(2):022001, IOP Publishing, England (Jun. 2010).
Katsumata, M., "Promotion of Intramuscular Fat Accumulation in Porcine Muscle by Nutritional Regulation," Animal Science Journal, 82(1):17-25, Wiley, Australia(Feb. 2011).
Klemm, D., et al., "Cellulose: Fascinating Biopolymer and Sustainable Raw Material," Angewandte Chemie International Edition, 44(22):3358-3393, (May 2005).
Kosnik, P.E., et al.,"Tissue Engineering Skeletal Muscle," Functional Tissue Engineering, 377-392, Springer-Verlag, United States, (2003).
Langelaan M.L.P., et al.,, "Meet the New Meat: Tissue Engineered Skeletal Muscle," Trends in Food Science & Technology, 21(2):59-66, Elsevier, (Feb. 2010).
Langer, R. and Vacanti, J.P.,, "Tissue Engineering; Science," Science, 260(5110):920-926, American Association for the Advancement of Science, (May 1993).
Lanza., et al., "Principles of Tissue Engineering; 3rd. Ed.; Chapter 12 Principles of Tissue Culture and Bioreactor Design (III. Principles of Bioreactor Design)," Academic Press, 165-166, (Aug. 2007).
Lee, W., et al., "Multi-layered Culture of Human Skin Fibroblasts and Keratinocytes Through Three-dimensional Freeform Fabrication," Biomaterials 30(8):1587-1595, Elsevier Science, Netherlands (Mar. 2009).
Levenberg, S., et al., "Engineering Vascularized Skeletal Muscle Tissue," Nature Biotechnology, 23(7):879-884, Nature America Publishing, United States (Jul. 2005).
Li, M., et al., "Soy Protein-Modified Waterborne Polyurethane Biocomposites With Improved Functionality", RSC advances, 6(16):12837-12849, Royal Society of Chemistry (2016).
Lin, Y., et al., "Physical, Mechanical, and Thermal Properties of Water-Blown Rigid Polyurethane Foam Containing Soy Protein Isolate", Cereal Chemistry 73(2):189-196, American Association of Cereal Chemists, Inc (1996).
Lin, Y., et al., "Water-Blown Flexible Polyurethane Foam Extended with Biomass Materials", Journal of Applied Polymer Science 65(4):695-703, John Wiley & Sons, Inc (Jul. 1997).

Liu, D., et al., "Structure and Properties of Blend Films Prepared from Castor Oil-Based Polyurethane/Soy Protein Derivative", Industrial & Engineering Chemistry Research 47(23):9330-9336, American Chemical Society (2008).
Madbouly, S.A and Lendlein, A., "Degradable Polyurethane/Soy Protein Shape-Memory Polymer Blends Prepared Via Environmentally-Friendly Aqueous Dispersions," Macromolecular Materials and Engineering 297(12):1213-1224, Wiley-VCH Verlag GmbH & Co. KGaA, Weinheim (Nov. 2012).
Mandal, B, and Majumdar, S.G.,"Nutritional Evaluation of Proteins from three Non-Traditional Seeds with or without Amino Acids Supplementation in Albino Rats," Proceedings of the Indian National Science Academy B50 No. 1:48-56, Nutritional Evaluation of Non-traditional Seed Proteins, Biochemistry Department, Burdwan Medical College, Burdwan (1984).
Marga. F., et al., "Developmental Biology and Tissue Engineering," Birth Defects Research Part C: Embryo Today 81(4):320-328, Wiley Periodicals, Inc, United States (Dec. 2007).
Marga. F., et al., "Toward Engineering Functional Organ Modules by Additive Manufacturing," Biofabrication 4(2):022001, IOP Publishing, England (Jun. 2012).
Matsuda, N., et al.,, "Tissue Engineering Based on Cell Sheet Technology," Advanced Materials, 19(20):3089-3099, John Wiley & Sons, (Oct. 2007).
Mead, P.S., et al.,, "Food-related Illness and Death in the United States," Emerging infectious diseases, 5(5):607-625, National Center for Infectious Diseases, Centers for Disease Control and Prevention (CDC), United States, (Sep. 1999).
Meyer, M., et al., "Collagen Fibres by Theromoplastic and Wet Spinning," Materials Science and Engineering C, 30(8):1266-1271, ResearchGate , (Oct. 2010).
Mironov., et al., "Biofabrication: a 21st century manufacturing paradigm" Biofabrication 1 (2009) pp. 1-16.
Mironov, V., et al., "Bioprinting Living Structures," Journal of Materials Chemistry 17(20):2054-2060 (May 2007).
Munarin, F., et al.,, "Pectin-based Injectable Biomaterials for Bone Tissue Engineering," Biomacromolecules, 12(3):568-577, American Chemical Society, United States, (Mar. 2011), (Abstract Only).
Native collagen, bovine dermis, Retrieved on Oct. 13, 2018], Retrieved from the Internet (https://www.cosmobio.com/products/kou_iac50_50.html).
Niklason, L.E., et al., "Advances in Tissue Engineering of Blood Vessels and Other Tissues," Transplant Immunology 5(4):303-306, Elsevier, Netherlands (Dec. 1997).
Norotte, C., et al., "Scaffold-free Vascular Tissue Engineering Using Bioprinting," Biomaterials 30(30):5910-5917, Elsevier Science, Netherlands (Oct. 2009).
Park, H., et al.,, "Effects of Electrical Stimulation in C2C12 Muscle Constructs," Journal of tissue engineering and regenerative medicine, 2(5):279-287, John Wiley & Sons, England, (Jul. 2008).
Park, S.K and Hettiarachchy, N.S., "Physical and Mechanical Properties of Soy Protein-Based Plastic Foams", Journal of the American Oil Chemists, Society 76(10):1201-1205, AOCS Press (1999).
Perera, G., et al.,, "Hydrophobic Thiolation of Pectin With 4-aminothiophenol: Synthesis and in Vitro Characterization," American Association of Pharmaceutical Scientists, 11(1):174-180, American Association of Pharmaceutical Scientists, United States, (Mar. 2010).
Perez-Pomares, J.M., et al., "Tissue Fusion and Cell Sorting in Embryonic Development and Disease: Biomedical Implications," Bioessays 28(8):809-821, Wiley, United States (Aug. 2006).
Pette D., et al., "What Does Chronic Electrical Stimulation Teach Us About Muscle Plasticity?," Muscle & Nerve, 22(6):666-677, John Wiley & Sons, United States (Jun. 1999).
Rahman, M.M and Netravali, A.N., "Green Resin from Forestry Waste Residue "Karanja (*Pongamia pinnata*) Seed Cake" for BiobasedComposite Structures," ACS Sustainable Chemistry & Engineering 2(10):2318-2328, American Chemical Society (Oct. 2014).
Ren, X., et al., "Engineering ZonalCartilage Through Bioprinting Collagen Type II Hydrogel Constructs WithBiomimetic Chondrocyte Density Gradient, "Bmc Musculoskeletal Disorders17: 301, BioMed Central, England (2016).

(56) References Cited

OTHER PUBLICATIONS

Savadogo, P., et al.,, "Effects of Grazing Intensity and Prescribed Fire on Soil Physical and Hydrological Properties and Pasture Yield in the Savanna Woodlands of Burkina Faso," Agriculture, Ecosystems & Environment, 118(1-4):80-92, Elsevier B.V., (Jan. 2007).
Sekine, H., et al., "Myocardial Tissue Reconstruction: the Cell Sheet Engineering Approach," Inflammation and Regeneration, 27 (3):171-176, (May 2007).
Shepherd, J.H., et al., "Effect of Fiber Crosslinking on Collagen-fiber Reinforced Collagen-chondroitin-6-sulfate Materials for Regenerating Load-bearing Soft Tissues," Journal of biomedical materials research. Part A, 101(1):176-184, John Wiley & Sons, United States, (Jan. 2013).
Smith, C.M., et al., "Three-dimensional Bioassembly Tool for Generating Viable Tissue-engineered Constructs," Tissue Engineering 10(9-10):1566-1576, Mary Ann Liebert, Inc, United States (Sep.-Oct. 2004).
Smith, G.E., et al., "Molecular Engineering of the Autographa Californica Nuclear Polyhedrosis Virus Genome: Deletion Mutations Within the Polyhedrin Gene," Journal of virology, 46(2):584-593, American Society For Microbiology, United States, (May 1983).
Sommer, F., et al., "Ascorbic Acid Modulates Proliferation and Extracellular Matrix Accumulation of Hyalocytes," Tissue engineering, 13(6):1281-1289, Mary Ann Liebert, Inc., United States, (Jun. 2007) abstract only.
Suganya, S., et al., "Naturally Derived Biofunctional Nanofibrous Scaffold For Skin Tissue Regeneration," International Journal of Biological Macromolecules 68:135-143, Elsevier, Netherlands (Jul. 2014).
Thelen, M.H., et al., "Electrical Stimulation of C2C12 Myotubes Induces Contractions and Represses Thyroid Hormone-Dependent Transcription of the Fast-type Sarcoplasmic-reticulum Ca2+-ATPase Gene," The Biochemical journal, 321(Pt 3):845-848, Published by Portland Press on behalf of the Biochemical Society, England, (Feb. 1997).
Thibault, J.F., and Rinaudo, M., , "Chain Association of Pectic Molecules During Calcium-induced Gelation," Biopolymers, 25(3):455-468, John Wiley & Sons, (Mar. 1986).
Tian, H., et al., "Improved Flexibility and Water Resistance of Soy Protein Thermoplastics Containing Waterborne Polyurethane," Industrial Crops and Products 32(1):13-20, Elsevier B.V, (Jul. 2010).
Tian, H., et al., "Polyether Polyol-Based Rigid Polyurethane Foams Reinforced With Soy Protein Fillers", Journal of Vinyl & Additive Technology 24(S1): E105-E111, Society of Plastics Engineers (2017).
Tong, X., et al., "Development of Blend Films From Soy Meal Protein and Crudeglycerol-Based Waterborne Polyurethane", Industrial Crops and Products 67:11-17, Elsevier B.V (May 2015).
Tuomisto H.L. et al., "Environmental Impacts of Cultured Meat Production," Environmental Science & Technology, 45(14):6117-6123, American Chemical Society, (Jun. 2011).
Wang, G and Zhou, A., "Soy Protein Based Biodegradable Flexible Polyurethane Foam", Advanced Materials Research, 152-153:1862-1865, Trans Tech Publications, Switzerland (2011).
Wang, N and Zhang, L., "Preparation and Characterization of Soy Protein Plastics Plasticized With Waterborne Polyurethane, "Polymer International 54(1):233-239, Society of Chemical Industry, (Jan. 2005).
Wang, N., et al., "Mechanical Properties and Biodegradability of Crosslinked Soy Protein Isolate/Waterborne Polyurethane Composites", Journal of Applied Polymer Science 95:465-473, Wiley Periodicals, Inc (2005).
Wang, Y., et al., "Properties of Soy-Based Wood Adhesives Enhanced by Waterborne Polyurethane Modification", Journal of Biobased Materials and Bioenergy 11:330-335, American Scientific Publishers (2017).
Wu, B., et al., "The New Development of Modified Collagen Protein Spinning," Leather Science and Engineering 17(4):27-31, China Academic Journal Electronic Publishing House (Aug. 2007).

Wu, Y., et al.,, "Fiber Formation by Dehydration-induced Aggregation of Albumin," Journal of Applied Polymer Science, 129(6):3591-3600, Wiley Periodicals, (Sep. 2013).
Xie, D.Y., et al., "Roles of Soft Segment Length in Structure and Property of Soy Protein Isolate/Waterborne Polyurethane Blend Films", Journal of Industrial and Engineering Chemistry Research 55(5):1229-1235, American Chemical Society (Jan. 2016).
Yang, J. et al., "Cell Sheet Engineering: Recreating Tissues Without Biodegradable Scaffolds," Biomaterials, 26(33):6415-6422, Elsevier Science, Netherlands, (Nov. 2005).
Zhang, M., et al., "Development of Soy Protein Isolate/waterborne Polyurethane Blend Films With Improved Properties", Colloids and Surfaces B: Biointerfaces 100:16-21, Elsevier B.V, Netherlands (Dec. 2012).
Koide, T., "Application of Collagen-like Triple-helical Peptides to Biochemical Studies Elucidating the Collagen Structure and Functions," Seikagaku. The Journal of Japanese Biochemical Society 82(6):474-483, Nippon Seikagakkai, Japan (Jun. 2010).
Langrock, T., et al., "Analysis of Hydroxyproline Isomers and Hydroxylysine by Reversed-Phase HPLC and Mass Spectrometry," Journal of Chromatography B 847(2):282-288, Elsevier, Netherlands (Mar. 2007).
Teja, A.S and Koh, P.Y, "Synthesis, Properties, and Applications of Magnetic Iron Oxide Nanoparticles," Progress in Crystal Growth and Characterization of Materials, 55(1-2):22-45, (Mar.-Jun. 2009).
Chen, X., et al., "Effect of the Application of a Dehydrothermal Treatment on the Structure and the Mechanical Properties of Collagen Film," Materials 13(2):377, Basel, Switzerland (Jan. 2020).
Covington, A.D ., "Modern Tanning Chemistry," Chemical Society Reviews, 26: 111-126. (1997).
Guide to Tensile Strength : Monroe, Accessed at URL : https://monroeengineering.com/info-general-guide-tensile-strength.php, Accessed on Jul. 21, 2021.
ISO 3376:2020 [IULTCS/IUP 6], "Leather—Physical and Mechanical Tests—Determination of Tensile Strength and Percentage Elongation," Technical Committee : IULTCS International Union of Leather Technologists and Chemists Societies, 4th Edition, 6 pages (May 2020).
Jus, S., et al., "Tyrosinase-Catalysed Coating of Wool Fibres With Different Protein-Based Biomaterials," Journal of Biomaterials Science 20(2):253-269, Taylor and Francis, England (2009).
Li, Z., et al., "Mechanical Behaviour of Natural Cow Leather in Tension," Acta Mechanica Solida Sinica 22(1):37-44, AMSS Press, China (2009).
Rajan, R., et al., "Design and in Vitro Evaluation of Chlorpheniramine Maleate From Different Eudragit Based Matrix Patches: Effect of Platicizer and Chemical Enhancers," ARS Pharmaceutica 50(4):177-194 (2010).
Schoff, C.K., "Crosslinking and Crosslink Density," Coatings Clinic (Sep. 1, 2010).
Wang, N., et al., "Properties of Crosslinked Casein/Waterborne Polyurethane Composites," Journal of Applied Polymer Science 91:332-338, John Wiley & Sons, United States (2004).
Yeelack, W and Meesane, J., "Preparation and Characterization of Coated Silk Fibroin Films with Mimicked Re-self Assembly Type I Collagen," The 2013 Biomedical Engineering International Conference, National Research University, Russia (2013).
Yunhui, X.U., et al., "Study of Cotton Fiber Coated by Collagen," Journal of Textile Research 28(5) (May 2007).
Co-Pending U.S. Appl. No. 17/438,582, filed Sep. 13, 2021, Handlin; D.L., et al., (Unpublished).
Co-pending Application, U.S. Appl. No. 17/783,570. Inventor: Cai; Shaobo. (Not Published).
Co-pending Application, U.S. Appl. No. 17/819,544. Inventor: Broadbent; Samuel. (Not Published).
Bareil et al., Collagen Based Biomaterials for Tissue Engineering Applications, Materials, 2010, 3, 1863-1887.
The Editorial Board of Patent Literature Bulletin—Textile, Patent Literature Bulletin—Textile, Shanghai: Shanghai Science and Technology Literature Publishing House, Jun. 30, 1981.
Zang et al., Effects of Collagen Treatment on the Structure and Properties of Salt-Shrinked Filaments, Jiangsu Textile, No. 12, Dec. 31, 2008.

(56) References Cited

OTHER PUBLICATIONS

Hu et al., Study on the $Ca(NO_3)_2$ Modified Silk Fiber Treated with Chitosan, Silk Research and Technology, China Academic Journal Electronic Publishing House, Dec. 25, 2005.

Chen et al., Study on the Process of Calcium Nitrate Modifying of Mulberry Silk Knitted Fabrics, Journal of Textile Research, vol. 29, No. 1, China Academic Journal Electronic Publishing House, Jan. 15, 2008.

\* cited by examiner

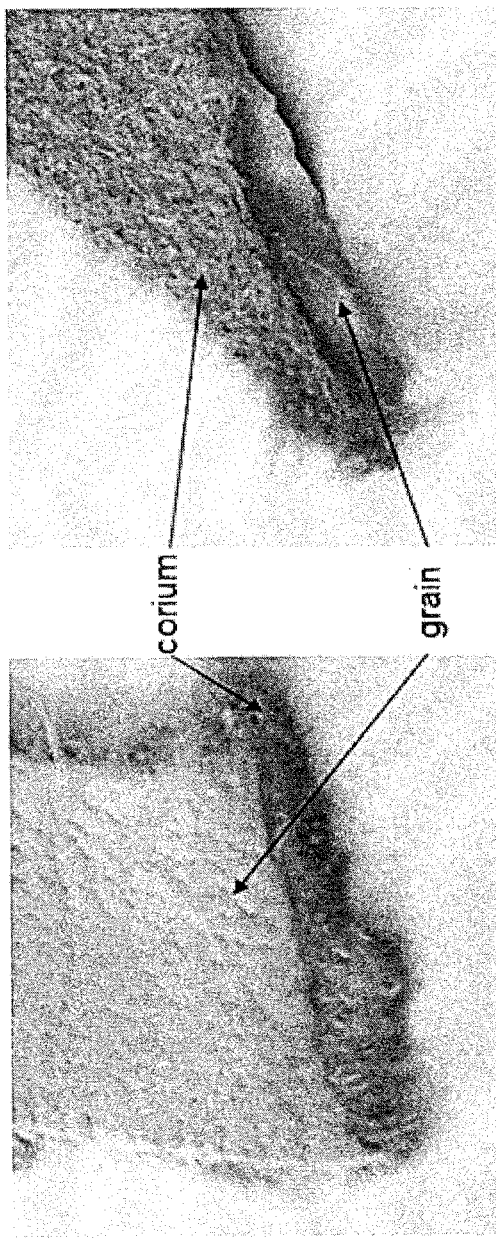

FIG. 3A
FIG. 3B
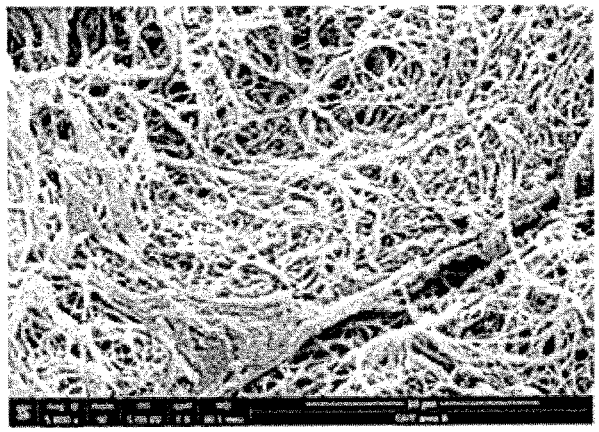
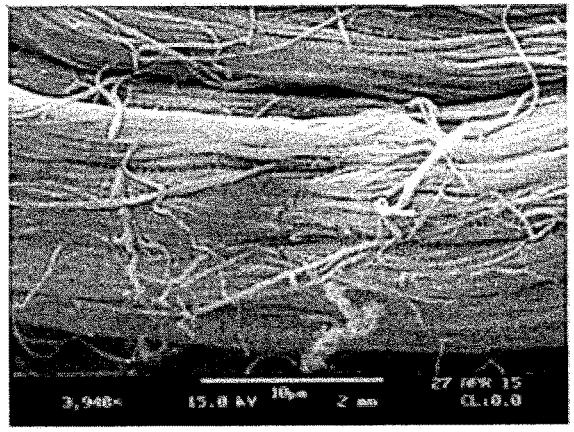
PRIOR ART
FIG. 4

SEQUENCE LISTING

```
<160> NUMBER OF SEQ ID NOS: 3

<210> SEQ ID NO 1
<211> LENGTH: 1463
<212> TYPE: PRT
<213> ORGANISM: Bos taurus
<220> FEATURE:
<221> NAME/KEY: MISC_FEATURE
<222> LOCATION: (1)..(1463)
<223> OTHER INFORMATION: collagen alpha-1(I) chain precursor

<400> SEQUENCE: 1

Met Phe Ser Phe Val Asp Leu Arg Leu Leu Leu Leu Leu Ala Ala Thr
1               5                   10                  15

Ala Leu Leu Thr His Gly Gln Glu Glu Gly Gln Glu Glu Gly Gln Glu
            20                  25                  30

Glu Asp Ile Pro Pro Val Thr Cys Val Gln Asn Gly Leu Arg Tyr His
        35                  40                  45

Asp Arg Asp Val Trp Lys Pro Val Pro Cys Gln Ile Cys Val Cys Asp
    50                  55                  60

Asn Gly Asn Val Leu Cys Asp Asp Val Ile Cys Asp Glu Leu Lys Asp
65                  70                  75                  80

Cys Pro Asn Ala Lys Val Pro Thr Asp Glu Cys Cys Pro Val Cys Pro
                85                  90                  95
```

-continued

```
Glu Gly Gln Glu Ser Pro Thr Asp Gln Glu Thr Thr Gly Val Glu Gly
                100                 105                 110

Pro Lys Gly Asp Thr Gly Pro Arg Gly Pro Arg Gly Pro Ala Gly Pro
            115                 120                 125

Pro Gly Arg Asp Gly Ile Pro Gly Gln Pro Gly Leu Pro Gly Pro Pro
        130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Ile Ser Val
                165                 170                 175

Pro Gly Pro Met Gly Pro Ser Gly Pro Arg Gly Leu Pro Gly Pro Pro
            180                 185                 190

Gly Ala Pro Gly Pro Gln Gly Phe Gln Gly Pro Pro Gly Glu Pro Gly
        195                 200                 205

Glu Pro Gly Ala Ser Gly Pro Met Gly Pro Arg Gly Pro Pro Gly Pro
210                 215                 220

Pro Gly Lys Asn Gly Asp Asp Gly Glu Ala Gly Lys Pro Gly Arg Pro
225                 230                 235                 240

Gly Glu Arg Gly Pro Pro Gly Pro Gln Gly Ala Arg Gly Leu Pro Gly
                245                 250                 255

Thr Ala Gly Leu Pro Gly Met Lys Gly His Arg Gly Phe Ser Gly Leu
            260                 265                 270

Asp Gly Ala Lys Gly Asp Ala Gly Pro Ala Gly Pro Lys Gly Glu Pro
        275                 280                 285

Gly Ser Pro Gly Glu Asn Gly Ala Pro Gly Gln Met Gly Pro Arg Gly
290                 295                 300

Leu Pro Gly Glu Arg Gly Arg Pro Gly Ala Pro Gly Pro Ala Gly Ala
305                 310                 315                 320

Arg Gly Asn Asp Gly Ala Thr Gly Ala Ala Gly Pro Pro Gly Pro Thr
                325                 330                 335

Gly Pro Ala Gly Pro Pro Gly Phe Pro Gly Ala Val Gly Ala Lys Gly
            340                 345                 350

Glu Gly Gly Pro Gln Gly Pro Arg Gly Ser Glu Gly Pro Gln Gly Val
        355                 360                 365

Arg Gly Glu Pro Gly Pro Pro Gly Pro Ala Gly Ala Ala Gly Pro Ala
370                 375                 380

Gly Asn Pro Gly Ala Asp Gly Gln Pro Gly Ala Lys Gly Ala Asn Gly
385                 390                 395                 400

Ala Pro Gly Ile Ala Gly Ala Pro Gly Phe Pro Gly Ala Arg Gly Pro
                405                 410                 415

Ser Gly Pro Gln Gly Pro Ser Gly Pro Pro Gly Pro Lys Gly Asn Ser
            420                 425                 430

Gly Glu Pro Gly Ala Pro Gly Ser Lys Gly Asp Thr Gly Ala Lys Gly
        435                 440                 445

Glu Pro Gly Pro Thr Gly Ile Gln Gly Pro Pro Gly Pro Ala Gly Glu
450                 455                 460

Glu Gly Lys Arg Gly Ala Arg Gly Glu Pro Gly Pro Ala Gly Leu Pro
465                 470                 475                 480

Gly Pro Pro Gly Glu Arg Gly Pro Gly Ser Arg Gly Phe Pro Gly
                485                 490                 495

Ala Asp Gly Val Ala Gly Pro Lys Gly Pro Ala Gly Glu Arg Gly Ala
            500                 505                 510

Pro Gly Pro Ala Gly Pro Lys Gly Ser Pro Gly Glu Ala Gly Arg Pro
```

```
            515                 520                 525
Gly Glu Ala Gly Leu Pro Gly Ala Lys Gly Leu Thr Gly Ser Pro Gly
            530                 535                 540

Ser Pro Gly Pro Asp Gly Lys Thr Gly Pro Pro Gly Pro Ala Gly Gln
545                 550                 555                 560

Asp Gly Arg Pro Gly Pro Pro Gly Pro Pro Gly Ala Arg Gly Gln Ala
                565                 570                 575

Gly Val Met Gly Phe Pro Gly Pro Lys Gly Ala Ala Gly Glu Pro Gly
                580                 585                 590

Lys Ala Gly Glu Arg Gly Val Pro Gly Pro Pro Gly Ala Val Gly Pro
            595                 600                 605

Ala Gly Lys Asp Gly Glu Ala Gly Ala Gln Gly Pro Pro Gly Pro Ala
            610                 615                 620

Gly Pro Ala Gly Glu Arg Gly Glu Gln Gly Pro Ala Gly Ser Pro Gly
625                 630                 635                 640

Phe Gln Gly Leu Pro Gly Pro Ala Gly Pro Pro Gly Glu Ala Gly Lys
                645                 650                 655

Pro Gly Glu Gln Gly Val Pro Gly Asp Leu Gly Ala Pro Gly Pro Ser
                660                 665                 670

Gly Ala Arg Gly Glu Arg Gly Phe Pro Gly Glu Arg Gly Val Gln Gly
            675                 680                 685

Pro Pro Gly Pro Ala Gly Pro Arg Gly Ala Asn Gly Ala Pro Gly Asn
690                 695                 700

Asp Gly Ala Lys Gly Asp Ala Gly Ala Pro Gly Ala Pro Gly Ser Gln
705                 710                 715                 720

Gly Ala Pro Gly Leu Gln Gly Met Pro Gly Glu Arg Gly Ala Ala Gly
                725                 730                 735

Leu Pro Gly Pro Lys Gly Asp Arg Gly Asp Ala Gly Pro Lys Gly Ala
                740                 745                 750

Asp Gly Ala Pro Gly Lys Asp Gly Val Arg Gly Leu Thr Gly Pro Ile
            755                 760                 765

Gly Pro Pro Gly Pro Ala Gly Ala Pro Gly Asp Lys Gly Glu Ala Gly
            770                 775                 780

Pro Ser Gly Pro Ala Gly Pro Thr Gly Ala Arg Gly Ala Pro Gly Asp
785                 790                 795                 800

Arg Gly Glu Pro Gly Pro Pro Gly Pro Ala Gly Phe Ala Gly Pro Pro
                805                 810                 815

Gly Ala Asp Gly Gln Pro Gly Ala Lys Gly Glu Pro Gly Asp Ala Gly
                820                 825                 830

Ala Lys Gly Asp Ala Gly Pro Pro Gly Pro Ala Gly Pro Ala Gly Pro
            835                 840                 845

Pro Gly Pro Ile Gly Asn Val Gly Ala Pro Gly Pro Lys Gly Ala Arg
            850                 855                 860

Gly Ser Ala Gly Pro Pro Gly Ala Thr Gly Phe Pro Gly Ala Ala Gly
865                 870                 875                 880

Arg Val Gly Pro Pro Gly Pro Ser Gly Asn Ala Gly Pro Pro Gly Pro
                885                 890                 895

Pro Gly Pro Ala Gly Lys Glu Gly Ser Lys Gly Pro Arg Gly Glu Thr
                900                 905                 910

Gly Pro Ala Gly Arg Pro Gly Glu Val Gly Pro Pro Gly Pro Pro Gly
            915                 920                 925

Pro Ala Gly Glu Lys Gly Ala Pro Gly Ala Asp Gly Pro Ala Gly Ala
            930                 935                 940
```

```
Pro Gly Thr Pro Gly Pro Gln Gly Ile Ala Gly Gln Arg Gly Val Val
945                 950                 955                 960

Gly Leu Pro Gly Gln Arg Gly Glu Arg Gly Phe Pro Gly Leu Pro Gly
            965                 970                 975

Pro Ser Gly Glu Pro Gly Lys Gln Gly Pro Ser Gly Ala Ser Gly Glu
            980                 985                 990

Arg Gly Pro Pro Gly Pro Met Gly Pro Pro Gly Leu Ala Gly Pro Pro
            995                 1000                1005

Gly Glu Ser Gly Arg Glu Gly Ala Pro Gly Ala Glu Gly Ser Pro
        1010                1015                1020

Gly Arg Asp Gly Ser Pro Gly Ala Lys Gly Asp Arg Gly Glu Thr
        1025                1030                1035

Gly Pro Ala Gly Pro Pro Gly Ala Pro Gly Ala Pro Gly Ala Pro
        1040                1045                1050

Gly Pro Val Gly Pro Ala Gly Lys Ser Gly Asp Arg Gly Glu Thr
        1055                1060                1065

Gly Pro Ala Gly Pro Ala Gly Pro Ile Gly Pro Val Gly Ala Arg
        1070                1075                1080

Gly Pro Ala Gly Pro Gln Gly Pro Arg Gly Asp Lys Gly Glu Thr
        1085                1090                1095

Gly Glu Gln Gly Asp Arg Gly Ile Lys Gly His Arg Gly Phe Ser
        1100                1105                1110

Gly Leu Gln Gly Pro Pro Gly Pro Pro Gly Ser Pro Gly Glu Gln
        1115                1120                1125

Gly Pro Ser Gly Ala Ser Gly Pro Ala Gly Pro Arg Gly Pro Pro
        1130                1135                1140

Gly Ser Ala Gly Ser Pro Gly Lys Asp Gly Leu Asn Gly Leu Pro
        1145                1150                1155

Gly Pro Ile Gly Pro Pro Gly Pro Arg Gly Arg Thr Gly Asp Ala
        1160                1165                1170

Gly Pro Ala Gly Pro Pro Gly Pro Pro Gly Pro Pro Gly Pro Pro
        1175                1180                1185

Gly Pro Pro Ser Gly Gly Tyr Asp Leu Ser Phe Leu Pro Gln Pro
        1190                1195                1200

Pro Gln Glu Lys Ala His Asp Gly Gly Arg Tyr Tyr Arg Ala Asp
        1205                1210                1215

Asp Ala Asn Val Val Arg Asp Arg Asp Leu Glu Val Asp Thr Thr
        1220                1225                1230

Leu Lys Ser Leu Ser Gln Gln Ile Glu Asn Ile Arg Ser Pro Glu
        1235                1240                1245

Gly Ser Arg Lys Asn Pro Ala Arg Thr Cys Arg Asp Leu Lys Met
        1250                1255                1260

Cys His Ser Asp Trp Lys Ser Gly Glu Tyr Trp Ile Asp Pro Asn
        1265                1270                1275

Gln Gly Cys Asn Leu Asp Ala Ile Lys Val Phe Cys Asn Met Glu
        1280                1285                1290

Thr Gly Glu Thr Cys Val Tyr Pro Thr Gln Pro Ser Val Ala Gln
        1295                1300                1305

Lys Asn Trp Tyr Ile Ser Lys Asn Pro Lys Glu Lys Arg His Val
        1310                1315                1320

Trp Tyr Gly Glu Ser Met Thr Gly Gly Phe Gln Phe Glu Tyr Gly
        1325                1330                1335
```

Gly Gln Gly Ser Asp Pro Ala Asp Val Ala Ile Gln Leu Thr Phe
    1340                1345                1350

Leu Arg Leu Met Ser Thr Glu Ala Ser Gln Asn Ile Thr Tyr His
    1355                1360                1365

Cys Lys Asn Ser Val Ala Tyr Met Asp Gln Gln Thr Gly Asn Leu
    1370                1375                1380

Lys Lys Ala Leu Leu Leu Gln Gly Ser Asn Glu Ile Glu Ile Arg
1385                1390                1395

Ala Glu Gly Asn Ser Arg Phe Thr Tyr Ser Val Thr Tyr Asp Gly
    1400                1405                1410

Cys Thr Ser His Thr Gly Ala Trp Gly Lys Thr Val Ile Glu Tyr
    1415                1420                1425

Lys Thr Thr Lys Thr Ser Arg Leu Pro Ile Ile Asp Val Ala Pro
    1430                1435                1440

Leu Asp Val Gly Ala Pro Asp Gln Glu Phe Gly Phe Asp Val Gly
    1445                1450                1455

Pro Ala Cys Phe Leu
    1460

<210> SEQ ID NO 2
<211> LENGTH: 1364
<212> TYPE: PRT
<213> ORGANISM: Bos taurus
<220> FEATURE:
<221> NAME/KEY: MISC_FEATURE
<222> LOCATION: (1)..(1364)
<223> OTHER INFORMATION: collagen alpha-2(I) chain precursor

<400> SEQUENCE: 2

Met Leu Ser Phe Val Asp Thr Arg Thr Leu Leu Leu Leu Ala Val Thr
1               5                   10                  15

Ser Cys Leu Ala Thr Cys Gln Ser Leu Gln Glu Ala Thr Ala Arg Lys
            20                  25                  30

Gly Pro Ser Gly Asp Arg Gly Pro Arg Gly Glu Arg Gly Pro Pro Gly
            35                  40                  45

Pro Pro Gly Arg Asp Gly Asp Asp Gly Ile Pro Gly Pro Pro Gly Pro
50                  55                  60

Pro Gly Pro Pro Gly Pro Pro Gly Leu Gly Gly Asn Phe Ala Ala Gln
65                  70                  75                  80

Phe Asp Ala Lys Gly Gly Gly Pro Gly Pro Met Gly Leu Met Gly Pro
                85                  90                  95

Arg Gly Pro Pro Gly Ala Ser Gly Ala Pro Gly Pro Gln Gly Phe Gln
            100                 105                 110

Gly Pro Pro Gly Glu Pro Gly Glu Pro Gly Gln Thr Gly Pro Ala Gly
            115                 120                 125

Ala Arg Gly Pro Pro Gly Pro Pro Gly Lys Ala Gly Glu Asp Gly His
            130                 135                 140

Pro Gly Lys Pro Gly Arg Pro Gly Glu Arg Gly Val Val Gly Pro Gln
145                 150                 155                 160

Gly Ala Arg Gly Phe Pro Gly Thr Pro Gly Leu Pro Gly Phe Lys Gly
                165                 170                 175

Ile Arg Gly His Asn Gly Leu Asp Gly Leu Lys Gly Gln Pro Gly Ala
            180                 185                 190

Pro Gly Val Lys Gly Glu Pro Gly Ala Pro Gly Glu Asn Gly Thr Pro
            195                 200                 205

Gly Gln Thr Gly Ala Arg Gly Leu Pro Gly Glu Arg Gly Arg Val Gly

```
            210                 215                 220
Ala Pro Gly Pro Ala Gly Ala Arg Gly Ser Asp Gly Ser Val Gly Pro
225                 230                 235                 240

Val Gly Pro Ala Gly Pro Ile Gly Ser Ala Gly Pro Pro Gly Phe Pro
                245                 250                 255

Gly Ala Pro Gly Pro Lys Gly Glu Leu Gly Pro Val Gly Asn Pro Gly
            260                 265                 270

Pro Ala Gly Pro Ala Gly Pro Arg Gly Glu Val Gly Leu Pro Gly Leu
                275                 280                 285

Ser Gly Pro Val Gly Pro Pro Gly Asn Pro Gly Ala Asn Gly Leu Pro
            290                 295                 300

Gly Ala Lys Gly Ala Ala Gly Leu Pro Gly Val Ala Gly Ala Pro Gly
305                 310                 315                 320

Leu Pro Gly Pro Arg Gly Ile Pro Gly Pro Val Gly Ala Ala Gly Ala
                325                 330                 335

Thr Gly Ala Arg Gly Leu Val Gly Glu Pro Gly Pro Ala Gly Ser Lys
                340                 345                 350

Gly Glu Ser Gly Asn Lys Gly Glu Pro Gly Ala Val Gly Gln Pro Gly
            355                 360                 365

Pro Pro Gly Pro Ser Gly Glu Glu Gly Lys Arg Gly Ser Thr Gly Glu
370                 375                 380

Ile Gly Pro Ala Gly Pro Pro Gly Pro Pro Gly Leu Arg Gly Asn Pro
385                 390                 395                 400

Gly Ser Arg Gly Leu Pro Gly Ala Asp Gly Arg Ala Gly Val Met Gly
                405                 410                 415

Pro Ala Gly Ser Arg Gly Ala Thr Gly Pro Ala Gly Val Arg Gly Pro
                420                 425                 430

Asn Gly Asp Ser Gly Arg Pro Gly Glu Pro Gly Leu Met Gly Pro Arg
            435                 440                 445

Gly Phe Pro Gly Ser Pro Gly Asn Ile Gly Pro Ala Gly Lys Glu Gly
            450                 455                 460

Pro Val Gly Leu Pro Gly Ile Asp Gly Arg Pro Gly Pro Ile Gly Pro
465                 470                 475                 480

Ala Gly Ala Arg Gly Glu Pro Gly Asn Ile Gly Phe Pro Gly Pro Lys
                485                 490                 495

Gly Pro Ser Gly Asp Pro Gly Lys Ala Gly Glu Lys Gly His Ala Gly
            500                 505                 510

Leu Ala Gly Ala Arg Gly Ala Pro Gly Pro Asp Gly Asn Asn Gly Ala
            515                 520                 525

Gln Gly Pro Pro Gly Leu Gln Gly Val Gln Gly Gly Lys Gly Glu Gln
            530                 535                 540

Gly Pro Ala Gly Pro Pro Gly Phe Gln Gly Leu Pro Gly Pro Ala Gly
545                 550                 555                 560

Thr Ala Gly Glu Ala Gly Lys Pro Gly Glu Arg Gly Ile Pro Gly Glu
                565                 570                 575

Phe Gly Leu Pro Gly Pro Ala Gly Ala Arg Gly Glu Arg Gly Pro Pro
                580                 585                 590

Gly Glu Ser Gly Ala Ala Gly Pro Thr Gly Pro Ile Gly Ser Arg Gly
            595                 600                 605

Pro Ser Gly Pro Pro Gly Pro Asp Gly Asn Lys Gly Glu Pro Gly Val
            610                 615                 620

Val Gly Ala Pro Gly Thr Ala Gly Pro Ser Gly Pro Ser Gly Leu Pro
625                 630                 635                 640
```

-continued

Gly Glu Arg Gly Ala Ala Gly Ile Pro Gly Lys Gly Glu Lys Gly
              645                 650                 655

Glu Thr Gly Leu Arg Gly Asp Ile Gly Ser Pro Gly Arg Asp Gly Ala
              660                 665                 670

Arg Gly Ala Pro Gly Ala Ile Gly Ala Pro Gly Pro Ala Gly Ala Asn
              675                 680                 685

Gly Asp Arg Gly Glu Ala Gly Pro Ala Gly Pro Ala Gly Pro Ala Gly
              690                 695                 700

Pro Arg Gly Ser Pro Gly Glu Arg Gly Glu Val Gly Pro Ala Gly Pro
705                 710                 715                 720

Asn Gly Phe Ala Gly Pro Ala Gly Ala Ala Gly Gln Pro Gly Ala Lys
              725                 730                 735

Gly Glu Arg Gly Thr Lys Gly Pro Lys Gly Glu Asn Gly Pro Val Gly
              740                 745                 750

Pro Thr Gly Pro Val Gly Ala Ala Gly Pro Ser Gly Pro Asn Gly Pro
              755                 760                 765

Pro Gly Pro Ala Gly Ser Arg Gly Asp Gly Gly Pro Pro Gly Ala Thr
              770                 775                 780

Gly Phe Pro Gly Ala Ala Gly Arg Thr Gly Pro Pro Gly Pro Ser Gly
785                 790                 795                 800

Ile Ser Gly Pro Pro Gly Pro Pro Gly Pro Ala Gly Lys Glu Gly Leu
              805                 810                 815

Arg Gly Pro Arg Gly Asp Gln Gly Pro Val Gly Arg Ser Gly Glu Thr
              820                 825                 830

Gly Ala Ser Gly Pro Pro Gly Phe Val Gly Glu Lys Gly Pro Ser Gly
              835                 840                 845

Glu Pro Gly Thr Ala Gly Pro Pro Gly Thr Pro Gly Pro Gln Gly Leu
              850                 855                 860

Leu Gly Ala Pro Gly Phe Leu Gly Leu Pro Gly Ser Arg Gly Glu Arg
865                 870                 875                 880

Gly Leu Pro Gly Val Ala Gly Ser Val Gly Glu Pro Gly Pro Leu Gly
              885                 890                 895

Ile Ala Gly Pro Pro Gly Ala Arg Gly Pro Pro Gly Asn Val Gly Asn
              900                 905                 910

Pro Gly Val Asn Gly Ala Pro Gly Glu Ala Gly Arg Asp Gly Asn Pro
              915                 920                 925

Gly Asn Asp Gly Pro Pro Gly Arg Asp Gly Gln Pro Gly His Lys Gly
              930                 935                 940

Glu Arg Gly Tyr Pro Gly Asn Ala Gly Pro Val Gly Ala Ala Gly Ala
945                 950                 955                 960

Pro Gly Pro Gln Gly Pro Val Gly Pro Val Gly Lys His Gly Asn Arg
              965                 970                 975

Gly Glu Pro Gly Pro Ala Gly Ala Val Gly Pro Ala Gly Ala Val Gly
              980                 985                 990

Pro Arg Gly Pro Ser Gly Pro Gln Gly Ile Arg Gly Asp Lys Gly Glu
              995                1000                1005

Pro Gly Asp Lys Gly Pro Arg Gly Leu Pro Gly Leu Lys Gly His
              1010                1015                1020

Asn Gly Leu Gln Gly Leu Pro Gly Leu Ala Gly His His Gly Asp
              1025                1030                1035

Gln Gly Ala Pro Gly Ala Val Gly Pro Ala Gly Pro Arg Gly Pro
              1040                1045                1050

Ala Gly Pro Ser Gly Pro Ala Gly Lys Asp Gly Arg Ile Gly Gln
    1055                1060                1065

Pro Gly Ala Val Gly Pro Ala Gly Ile Arg Gly Ser Gln Gly Ser
    1070                1075                1080

Gln Gly Pro Ala Gly Pro Pro Gly Pro Pro Gly Pro Pro Gly Pro
    1085                1090                1095

Pro Gly Pro Ser Gly Gly Gly Tyr Glu Phe Gly Phe Asp Gly Asp
    1100                1105                1110

Phe Tyr Arg Ala Asp Gln Pro Arg Ser Pro Thr Ser Leu Arg Pro
    1115                1120                1125

Lys Asp Tyr Glu Val Asp Ala Thr Leu Lys Ser Leu Asn Asn Gln
    1130                1135                1140

Ile Glu Thr Leu Leu Thr Pro Glu Gly Ser Arg Lys Asn Pro Ala
    1145                1150                1155

Arg Thr Cys Arg Asp Leu Arg Leu Ser His Pro Glu Trp Ser Ser
    1160                1165                1170

Gly Tyr Tyr Trp Ile Asp Pro Asn Gln Gly Cys Thr Met Asp Ala
    1175                1180                1185

Ile Lys Val Tyr Cys Asp Phe Ser Thr Gly Glu Thr Cys Ile Arg
    1190                1195                1200

Ala Gln Pro Glu Asp Ile Pro Val Lys Asn Trp Tyr Arg Asn Ser
    1205                1210                1215

Lys Ala Lys Lys His Val Trp Val Gly Glu Thr Ile Asn Gly Gly
    1220                1225                1230

Thr Gln Phe Glu Tyr Asn Val Glu Gly Val Thr Thr Lys Glu Met
    1235                1240                1245

Ala Thr Gln Leu Ala Phe Met Arg Leu Leu Ala Asn His Ala Ser
    1250                1255                1260

Gln Asn Ile Thr Tyr His Cys Lys Asn Ser Ile Ala Tyr Met Asp
    1265                1270                1275

Glu Glu Thr Gly Asn Leu Lys Lys Ala Val Ile Leu Gln Gly Ser
    1280                1285                1290

Asn Asp Val Glu Leu Val Ala Glu Gly Asn Ser Arg Phe Thr Tyr
    1295                1300                1305

Thr Val Leu Val Asp Gly Cys Ser Lys Lys Thr Asn Glu Trp Gln
    1310                1315                1320

Lys Thr Ile Ile Glu Tyr Lys Thr Asn Lys Pro Ser Arg Leu Pro
    1325                1330                1335

Ile Leu Asp Ile Ala Pro Leu Asp Ile Gly Gly Ala Asp Gln Glu
    1340                1345                1350

Ile Arg Leu Asn Ile Gly Pro Val Cys Phe Lys
    1355                1360

<210> SEQ ID NO 3
<211> LENGTH: 1466
<212> TYPE: PRT
<213> ORGANISM: Bos taurus
<220> FEATURE:
<221> NAME/KEY: MISC_FEATURE
<222> LOCATION: (1)..(1466)
<223> OTHER INFORMATION: collagen alpha-1(III) chain precursor

<400> SEQUENCE: 3

Met Met Ser Phe Val Gln Lys Gly Thr Trp Leu Leu Phe Ala Leu Leu
1               5                   10                  15

His Pro Thr Val Ile Leu Ala Gln Gln Glu Ala Val Asp Gly Gly Cys

```
                    20                  25                  30
Ser His Leu Gly Gln Ser Tyr Ala Asp Arg Asp Val Trp Lys Pro Glu
                35                  40                  45

Pro Cys Gln Ile Cys Val Cys Asp Ser Gly Ser Val Leu Cys Asp Asp
             50                  55                  60

Ile Ile Cys Asp Asp Gln Glu Leu Asp Cys Pro Asn Pro Glu Ile Pro
 65                  70                  75                  80

Phe Gly Glu Cys Cys Ala Val Cys Pro Gln Pro Thr Ala Pro Thr
                     85                  90                  95

Arg Pro Pro Asn Gly Gln Gly Pro Gln Gly Pro Lys Gly Asp Pro Gly
                100                 105                 110

Pro Pro Gly Ile Pro Gly Arg Asn Gly Asp Pro Gly Pro Pro Gly Ser
             115                 120                 125

Pro Gly Ser Pro Gly Ser Pro Gly Pro Pro Gly Ile Cys Glu Ser Cys
             130                 135                 140

Pro Thr Gly Gly Gln Asn Tyr Ser Pro Gln Tyr Glu Ala Tyr Asp Val
145                 150                 155                 160

Lys Ser Gly Val Ala Gly Gly Ile Ala Gly Tyr Pro Gly Pro Pro Ala
                 165                 170                 175

Gly Pro Pro Gly Pro Pro Gly Pro Pro Gly Thr Ser Gly His Pro Gly
                 180                 185                 190

Ala Pro Gly Ala Pro Gly Tyr Gln Gly Pro Pro Gly Glu Pro Gly Gln
             195                 200                 205

Ala Gly Pro Ala Gly Pro Pro Gly Pro Pro Gly Ala Ile Gly Pro Ser
             210                 215                 220

Gly Pro Ala Gly Lys Asp Gly Glu Ser Gly Arg Pro Gly Arg Pro Gly
225                 230                 235                 240

Glu Arg Gly Phe Pro Gly Pro Pro Gly Met Lys Gly Pro Ala Gly Met
                 245                 250                 255

Pro Gly Phe Pro Gly Met Lys Gly His Arg Gly Phe Asp Gly Arg Asn
                 260                 265                 270

Gly Glu Lys Gly Glu Thr Gly Ala Pro Gly Leu Lys Gly Glu Asn Gly
                 275                 280                 285

Val Pro Gly Glu Asn Gly Ala Pro Gly Pro Met Gly Pro Arg Gly Ala
290                 295                 300

Pro Gly Glu Arg Gly Arg Pro Gly Leu Pro Gly Ala Ala Gly Ala Arg
305                 310                 315                 320

Gly Asn Asp Gly Ala Arg Gly Ser Asp Gly Gln Pro Gly Pro Pro Gly
                 325                 330                 335

Pro Pro Gly Thr Ala Gly Phe Pro Gly Ser Pro Gly Ala Lys Gly Glu
                 340                 345                 350

Val Gly Pro Ala Gly Ser Pro Gly Ser Ser Gly Ala Pro Gly Gln Arg
                 355                 360                 365

Gly Glu Pro Gly Pro Gln Gly His Ala Gly Ala Pro Gly Pro Pro Gly
                 370                 375                 380

Pro Pro Gly Ser Asn Gly Ser Pro Gly Gly Lys Gly Glu Met Gly Pro
385                 390                 395                 400

Ala Gly Ile Pro Gly Ala Pro Gly Leu Ile Gly Ala Arg Gly Pro Pro
                 405                 410                 415

Gly Pro Pro Gly Thr Asn Gly Val Pro Gly Gln Arg Gly Ala Ala Gly
                 420                 425                 430

Glu Pro Gly Lys Asn Gly Ala Lys Gly Asp Pro Gly Pro Arg Gly Glu
                 435                 440                 445
```

```
Arg Gly Glu Ala Gly Ser Pro Gly Ile Ala Gly Pro Lys Gly Glu Asp
    450                 455                 460

Gly Lys Asp Gly Ser Pro Gly Glu Pro Gly Ala Asn Gly Leu Pro Gly
465                 470                 475                 480

Ala Ala Gly Glu Arg Gly Val Pro Gly Phe Arg Gly Pro Ala Gly Ala
            485                 490                 495

Asn Gly Leu Pro Gly Glu Lys Gly Pro Pro Gly Asp Arg Gly Gly Pro
                500                 505                 510

Gly Pro Ala Gly Pro Arg Gly Val Ala Gly Glu Pro Gly Arg Asp Gly
        515                 520                 525

Leu Pro Gly Gly Pro Gly Leu Arg Gly Ile Pro Gly Ser Pro Gly Gly
    530                 535                 540

Pro Gly Ser Asp Gly Lys Pro Gly Pro Gly Ser Gln Gly Glu Thr
545                 550                 555                 560

Gly Arg Pro Gly Pro Pro Gly Ser Pro Gly Pro Arg Gly Gln Pro Gly
            565                 570                 575

Val Met Gly Phe Pro Gly Pro Lys Gly Asn Asp Gly Ala Pro Gly Lys
                580                 585                 590

Asn Gly Glu Arg Gly Gly Pro Gly Gly Pro Gly Gln Gly Pro Ala
        595                 600                 605

Gly Lys Asn Gly Glu Thr Gly Pro Gln Gly Pro Pro Gly Pro Thr Gly
    610                 615                 620

Pro Ser Gly Asp Lys Gly Asp Thr Gly Pro Pro Gly Pro Gln Gly Leu
625                 630                 635                 640

Gln Gly Leu Pro Gly Thr Ser Gly Pro Pro Gly Glu Asn Gly Lys Pro
            645                 650                 655

Gly Glu Pro Gly Pro Lys Gly Glu Ala Gly Ala Pro Gly Ile Pro Gly
                660                 665                 670

Gly Lys Gly Asp Ser Gly Ala Pro Gly Glu Arg Gly Pro Pro Gly Ala
        675                 680                 685

Gly Gly Pro Pro Gly Pro Arg Gly Gly Ala Gly Pro Pro Gly Pro Glu
    690                 695                 700

Gly Gly Lys Gly Ala Ala Gly Pro Pro Gly Pro Pro Gly Ser Ala Gly
705                 710                 715                 720

Thr Pro Gly Leu Gln Gly Met Pro Gly Glu Arg Gly Pro Gly Gly
            725                 730                 735

Pro Gly Pro Lys Gly Asp Lys Gly Glu Pro Gly Ser Ser Gly Val Asp
                740                 745                 750

Gly Ala Pro Gly Lys Asp Gly Pro Arg Gly Pro Thr Gly Pro Ile Gly
        755                 760                 765

Pro Pro Gly Pro Ala Gly Gln Pro Gly Asp Lys Gly Glu Ser Gly Ala
    770                 775                 780

Pro Gly Val Pro Gly Ile Ala Gly Pro Arg Gly Gly Pro Gly Glu Arg
785                 790                 795                 800

Gly Glu Gln Gly Pro Pro Gly Pro Ala Gly Phe Pro Gly Ala Pro Gly
            805                 810                 815

Gln Asn Gly Glu Pro Gly Ala Lys Gly Glu Arg Gly Ala Pro Gly Glu
                820                 825                 830

Lys Gly Glu Gly Gly Pro Pro Gly Ala Ala Gly Pro Ala Gly Gly Ser
        835                 840                 845

Gly Pro Ala Gly Pro Pro Gly Pro Gln Gly Val Lys Gly Glu Arg Gly
    850                 855                 860
```

```
Ser Pro Gly Gly Pro Gly Ala Ala Gly Phe Pro Gly Gly Arg Gly Pro
865                 870                 875                 880

Pro Gly Pro Pro Gly Ser Asn Gly Asn Pro Gly Pro Pro Gly Ser Ser
            885                 890                 895

Gly Ala Pro Gly Lys Asp Gly Pro Pro Gly Pro Pro Gly Ser Asn Gly
        900                 905                 910

Ala Pro Gly Ser Pro Gly Ile Ser Gly Pro Lys Gly Asp Ser Gly Pro
    915                 920                 925

Pro Gly Glu Arg Gly Ala Pro Gly Pro Gln Gly Pro Pro Gly Ala Pro
930                 935                 940

Gly Pro Leu Gly Ile Ala Gly Leu Thr Gly Ala Arg Gly Leu Ala Gly
945                 950                 955                 960

Pro Pro Gly Met Pro Gly Ala Arg Gly Ser Pro Gly Pro Gln Gly Ile
            965                 970                 975

Lys Gly Glu Asn Gly Lys Pro Gly Pro Ser Gly Gln Asn Gly Glu Arg
        980                 985                 990

Gly Pro Pro Gly Pro Gln Gly Leu Pro Gly Leu Ala Gly Thr Ala Gly
        995                 1000                1005

Glu Pro Gly Arg Asp Gly Asn Pro Gly Ser Asp Gly Leu Pro Gly
    1010                1015                1020

Arg Asp Gly Ala Pro Gly Ala Lys Gly Asp Arg Gly Glu Asn Gly
    1025                1030                1035

Ser Pro Gly Ala Pro Gly Ala Pro Gly His Pro Gly Pro Pro Gly
    1040                1045                1050

Pro Val Gly Pro Ala Gly Lys Ser Gly Asp Arg Gly Glu Thr Gly
    1055                1060                1065

Pro Ala Gly Pro Ser Gly Ala Pro Gly Pro Ala Gly Ser Arg Gly
    1070                1075                1080

Pro Pro Gly Pro Gln Gly Pro Arg Gly Asp Lys Gly Glu Thr Gly
    1085                1090                1095

Glu Arg Gly Ala Met Gly Ile Lys Gly His Arg Gly Phe Pro Gly
    1100                1105                1110

Asn Pro Gly Ala Pro Gly Ser Pro Gly Pro Ala Gly His Gln Gly
    1115                1120                1125

Ala Val Gly Ser Pro Gly Pro Ala Gly Pro Arg Gly Pro Val Gly
    1130                1135                1140

Pro Ser Gly Pro Pro Gly Lys Asp Gly Ala Ser Gly His Pro Gly
    1145                1150                1155

Pro Ile Gly Pro Pro Gly Pro Arg Gly Asn Arg Gly Glu Arg Gly
    1160                1165                1170

Ser Glu Gly Ser Pro Gly His Pro Gly Gln Pro Gly Pro Pro Gly
    1175                1180                1185

Pro Pro Gly Ala Pro Gly Pro Cys Cys Gly Ala Gly Gly Val Ala
    1190                1195                1200

Ala Ile Ala Gly Val Gly Ala Glu Lys Ala Gly Gly Phe Ala Pro
    1205                1210                1215

Tyr Tyr Gly Asp Glu Pro Ile Asp Phe Lys Ile Asn Thr Asp Glu
    1220                1225                1230

Ile Met Thr Ser Leu Lys Ser Val Asn Gly Gln Ile Glu Ser Leu
    1235                1240                1245

Ile Ser Pro Asp Gly Ser Arg Lys Asn Pro Ala Arg Asn Cys Arg
    1250                1255                1260

Asp Leu Lys Phe Cys His Pro Glu Leu Gln Ser Gly Glu Tyr Trp
```

```
                1265                1270                1275
Val Asp Pro Asn Gln Gly Cys Lys Leu Asp Ala Ile Lys Val Tyr
    1280                1285                1290

Cys Asn Met Glu Thr Gly Glu Thr Cys Ile Ser Ala Ser Pro Leu
    1295                1300                1305

Thr Ile Pro Gln Lys Asn Trp Trp Thr Asp Ser Gly Ala Glu Lys
    1310                1315                1320

Lys His Val Trp Phe Gly Glu Ser Met Glu Gly Gly Phe Gln Phe
    1325                1330                1335

Ser Tyr Gly Asn Pro Glu Leu Pro Glu Asp Val Leu Asp Val Gln
    1340                1345                1350

Leu Ala Phe Leu Arg Leu Leu Ser Ser Arg Ala Ser Gln Asn Ile
    1355                1360                1365

Thr Tyr His Cys Lys Asn Ser Ile Ala Tyr Met Asp His Ala Ser
    1370                1375                1380

Gly Asn Val Lys Lys Ala Leu Lys Leu Met Gly Ser Asn Glu Gly
    1385                1390                1395

Glu Phe Lys Ala Glu Gly Asn Ser Lys Phe Thr Tyr Thr Val Leu
    1400                1405                1410

Glu Asp Gly Cys Thr Lys His Thr Gly Glu Trp Gly Lys Thr Val
    1415                1420                1425

Phe Gln Tyr Gln Thr Arg Lys Ala Val Arg Leu Pro Ile Val Asp
    1430                1435                1440

Ile Ala Pro Tyr Asp Ile Gly Gly Pro Asp Gln Glu Phe Gly Ala
    1445                1450                1455

Asp Ile Gly Pro Val Cys Phe Leu
    1460                1465
```

BIOFABRICATED MATERIAL CONTAINING COLLAGEN FIBRILS

CROSS REFERENCE TO RELATED APPLICATIONS

This application claims priority to U.S. Provisional Application No. 62/295,435 filed Feb. 15, 2016 and which is incorporated by reference in its entirety. This application is related to U.S. patent application Ser. No. 13/853,001, titled "ENGINEERED LEATHER AND METHODS OF MANUFACTURE THEREOF" and filed on Mar. 28, 2013; U.S. patent application Ser. No. 14/967,173, titled "ENGINEERED LEATHER AND METHODS OF MANUFACTURE THEREOF" and filed on Dec. 11, 2015; and PCT Patent Application No. PCT/US2015/058794, titled "REINFORCED ENGINEERED BIOMATERIALS AND METHODS OF MANUFACTURE THEREOF" and filed on Nov. 3, 2015.

BACKGROUND OF THE INVENTION

Field of the Invention

This invention relates to biofabricated leather materials composed of unbundled and randomly-oriented trimeric collagen fibrils that exhibit superior strength, non-anisotropic properties, and uniformity by comparison to conventional leather products, but which have the look, feel and other aesthetic properties of natural leather. Unlike synthetic leather products composed of plastic resins, the biofabricated leather of the invention is based on collagen, a natural component of leather.

Leather. Leather is used in a vast variety of applications, including furniture upholstery, clothing, shoes, luggage, handbag and accessories, and automotive applications. The estimated global trade value in leather is approximately US $100 billion per year (Future Trends in the World Leather Products Industry and Trade, United Nations Industrial Development Organization, Vienna, 2010) and there is a continuing and increasing demand for leather products. New ways to meet this demand are required in view of the economic, environmental and social costs of producing leather. To keep up with technological and aesthetic trends, producers and users of leather products seek new materials exhibiting superior strength, uniformity, processability and fashionable and appealing aesthetic properties that incorporate natural components.

Natural leathers are produced from the skins of animals which require raising livestock. However, the raising of livestock requires enormous amounts of feed, pastureland, water, and fossil fuels. It also produces air and waterway pollution, including production of greenhouse gases like methane. Some states in the United States, such as California, may impose taxes on the amounts of pollutants such as methane produced by livestock. As the costs of raising livestock rise, the cost of leather will rise.

The global leather industry slaughters more than a billion animals per year. Most leather is produced in countries that engage in factory farming, lack animal welfare laws, or in which such laws go largely or completely unenforced. This slaughter under inhumane conditions is objectionable to many socially conscious people. Consequently, there is a demand from consumers with ethical, moral or religious objections to the use of natural leather products for products humanely produced without the mistreatment or slaughter of animals or produced in ways that minimize the number of animals slaughtered.

The handling and processing of animal skins into leather also poses health risks because the handling animal skins can expose workers to anthrax and other pathogens and allergens such as those in leather dust. Factory farming of animals contributes to the spread of influenza (e.g. "bird flu") and other infectious diseases that may eventually mutate and infect humans. Animal derived products are also susceptible to contamination with viruses and prions ("mad cow disease"). For producer and consumer peace of mind, there exists a demand for leather products that do not present these risks.

Natural leather is generally a durable and flexible material created by processing rawhide and skin of an animal, such as cattle hides. This processing typically involves three main parts: preparatory stages, tanning, and retanning. Leather may also be surface coated or embossed.

Numerous ways are known to prepare a skin or hide and convert it to leather. These include salting or refrigerating a hide or skin to preserve it; soaking or rehydrating the hide in an aqueous solution that contains surfactants or other chemicals to remove salt, dirt, debris, blood, and excess fat; defleshing or removing subcutaneous material from the hide; dehairing or unhairing the hide remove most of the hair; liming the hide to loosen fibers and open up collagen bundles allowing it to absorb chemicals; splitting the hide into two or more layers; deliming the hide to remove alkali and lower its pH; bating the hide to complete the deliming process and smooth the grain; degreasing to remove excess fats; frizzing; bleaching; pickling by altering the pH; or depickling, Once the preparatory stages are complete, the leather is tanned. Leather is tanned to increase its durability compared to untreated hide. Tanning converts proteins in the hide or skin into a stable material that will not putrefy while allowing the leather material to remain flexible. During tanning, the skin structure may be stabilized in an "open" form by reacting some of the collagen with complex ions of chromium or other tanning agents. Depending on the compounds used, the color and texture of the leather may change.

Tanning is generally understood to be the process of treating the skins of animals to produce leather. Tanning may be performed in any number of well-understood ways, including by contacting a skin or hide with a vegetable tanning agent, chromium compound, aldehyde, syntan, synthetic, semisynthetic or natural resin or polymer, or/and tanning natural oil or modified oil. Vegetable tannins include pyrogallol- or pyrocatechin-based tannins, such as valonea, mimosa, ten, tara, oak, pinewood, sumach, quebracho and chestnut tannins; chromium tanning agents include chromium salts like chromium sulfate; aldehyde tanning agents include glutaraldehyde and oxazolidine compounds, syntans include aromatic polymers, polyacrylates, polymethacrylates, copolymers of maleic anhydride and styrene, condensation products of formaldehyde with melamine or dicyandiamide, lignins and natural flours.

Chromium is the most commonly used tanning material. The pH of the skin/hide may be adjusted (e.g., lowered, e.g. to pH 2.8-3.2) to allow penetration of the tanning agent; following penetration the pH may be raised to fix the tanning agent ("basification" to a slightly higher level, e.g., pH 3.8-4.2 for chrome).

After tanning, a leather may be retanned. Retanning refers to the post-tanning treatment that can include coloring (dying), thinning, drying or hydrating, and the like. Examples of retanning techniques include: tanning, wetting (rehydrating), sammying (drying), neutralization (adjusting pH to a less acidic or alkaline state), dyeing, fat liquoring, fixation of unbound chemicals, setting, conditioning, softening, buffing, etc.

A tanned leather product may be mechanically or chemically finished. Mechanical finishing can polish the leather to yield a shiny surface, iron and plate a leather to have a flat, smooth surface, emboss a leather to provide a three dimensional print or pattern, or tumble a leather to provide a more evident grain and smooth surface. Chemical finishing may involve the application of a film, a natural or synthetic coating, or other leather treatment. These may be applied, for example, by spraying, curtain-coating or roller coating.

In animal hide, variations in fibrous collagen organization are observed in animals of different ages or species. These differences affect the physical properties of hides and differences in leather produced from the hides. Variations in collagen organization also occur through the thickness of the hide. The top grain side of hide is composed of a fine network of collagen fibrils while deeper sections (corium) are composed of larger fiber bundles (FIG. 2). The smaller fibril organization of the grain layer gives rise to a soft and smooth leather aesthetic while the larger fiber bundle organization of deeper regions gives rise to a rough and course leather aesthetic.

The porous, fibrous organization of collagen in a hide allows applied molecules to penetrate, stabilize, and lubricate it during leather tanning. The combination of the innate collagen organization in hide and the modifications achieved through tanning give rise to the desirable strength, drape and aesthetic properties of leather.

The top grain surface of leather is often regarded as the most desirable due to its smoothness and soft texture. This leather grain contains a highly porous network of organized collagen fibrils. Endogenous collagen fibrils are organized to have lacunar regions and overlapping regions; see the hierarchical organization of collagen depicted by FIG. 1. The strengths, microscale porosity, and density of fibrils in a top grain leather allow tanning or fatliquoring agents to penetrate it, thus stabilizing and lubricating the collagen fibrils, producing a soft, smooth and strong leather that people desire.

Leather hides can be split to obtain leather that is mostly top grain. The split hide can be further abraded to reduce the coarser grained corium on the split side, but there is always some residual corium and associated rough appearance. In order to produce leather with smooth grain on both sides, it is necessary to combine two pieces of grain, corium side facing corium side and either sew them together or laminate them with adhesives with the smooth top grain sides facing outward. There is a demand for a leather product that has a smooth, top grain-like surface on both its sides, because this would avoid the need for splitting, and sewing or laminating two split leather pieces together.

Control of the final properties of leather is limited by the natural variation in collagen structure between different animal hides. For example, the relative thickness of grain to corium in goat hide is significantly higher than that in kangaroo hide. In addition, the weave angle of collagen fiber bundles in kangaroo corium are much more parallel to the surface of the hide, while fiber bundles in bovine corium are oriented in both parallel and perpendicular orientations to the surface of the hide. Further, the density of fiber bundles varies within each hide depending on their anatomical location. Hide taken from butt, belly, shoulder, and neck can have different compositions and properties. The age of an animal also affects the composition of its hide, for example, juvenile bovine hide contains smaller diameter fibers than the larger fiber bundles found in adult bovine hide.

The final properties of leather can be controlled to some extent through the incorporation of stabilizing and lubricating molecules into the hide or skin during tanning and retanning, however, the selection of these molecules is limited by the need to penetrate the dense structure of the skin or hide. Particles as large as several microns in diameter have been incorporated into leather for enhanced lubrication; however, application of these particles is limited to hides with the largest pore sizes. Uniformly distributing the particles throughout the hide presents many challenges.

Collagen. Collagen is a component of leather. Skin, or animal hide, contains significant amounts of collagen, a fibrous protein. Collagen is a generic term for a family of at least 28 distinct collagen types; animal skin is typically Type I collagen, although other types of collagen can be used in forming leather including type III collagen.

Collagens are characterized by a repeating triplet of amino acids, -(Gly-X-Y)$_n$— and approximately one-third of the amino acid residues in collagen are glycine. X is often proline and Y is often hydroxyproline, though there may be up to 400 possible Gly-X-Y triplets. Different animals may produce different amino acid compositions of the collagen, which may result in different properties and in differences in the resulting leather.

The structure of collagen can consist of three intertwined peptide chains of differing lengths. Collagen triple helices (or monomers) may be produced from alpha-chains of about 1,050 amino acids long, so that the triple helix takes the form of a rod of about approximately 300 nm long, with a diameter of approximately 1.5 nm.

In the production of extracellular matrix by fibroblast skin cells, triple helix monomers may be synthesized and the monomers may self-assemble into a fibrous form. These triple helices are held together by electrostatic interactions including salt bridging, hydrogen bonding, Van der Waals interactions, dipole-dipole forces, polarization forces, hydrophobic interactions, and/or covalent bonding. Triple helices can be bound together in bundles called fibrils, and fibrils can further assemble to create fibers and fiber bundles (FIG. 1).

Fibrils have a characteristic banded appearance due to the staggered overlap of collagen monomers. The distance between bands is approximately 67 nm for Type I collagen. Fibrils and fibers typically branch and interact with each other throughout a layer of skin. Variations of the organization or crosslinking of fibrils and fibers may provide strength to the material.

Fibers may have a range of diameters depending on the type of animal hide. In addition to type I collagen, skin (hides) may include other types of collagen as well, including type III collagen (reticulin), type IV collagen, and type VII collagen.

Various types of collagen exist throughout the mammalian body. For example, besides being the main component of skin and animal hide, Type I collagen also exists in cartilage, tendon, vascular ligature, organs, muscle, and the organic portion of bone. Successful efforts have been made to isolate collagen from various regions of the mammalian body in addition to the animal skin or hide. Decades ago, researchers found that at neutral pH, acid-solubilized collagen self-assembled into fibrils composed of the same cross-striated patterns observed in native tissue; Schmitt F. O. J. Cell. Comp Physiol. 1942; 20:11). This led to use of collagen in tissue engineering and a variety of biomedical applications.

In more recent years, collagen has been harvested from bacteria and yeast using recombinant techniques.

Regardless of the type of collagen, all are formed and stabilized through a combination of physical and chemical interactions including electrostatic interactions including salt bridging, hydrogen bonding, Van der Waals interactions, dipole-dipole forces, polarization forces, hydrophobic interactions, and covalent bonding often catalyzed by enzymatic reactions. For Type I collagen fibrils, fibers, and fiber bundles, its complex assembly is achieved in vivo during development and is critical in providing mechanical support to the tissue while allowing for cellular motility and nutrient transport. Various distinct collagen types have been identified in vertebrates. These include bovine, ovine, porcine, chicken, and human collagens.

Generally, the collagen types are numbered by Roman numerals, and the chains found in each collagen type are identified by Arabic numerals. Detailed descriptions of structure and biological functions of the various different types of naturally occurring collagens are available in the art; see, e.g., Ayad et al. (1998) The Extracellular Matrix Facts Book, Academic Press, San Diego, Calif.; Burgeson, R E., and Nimmi (1992) "Collagen types: Molecular Structure and Tissue Distribution" in Clin. Orthop. 282:250-272; Kielty, C. M. et al. (1993) "The Collagen Family: Structure, Assembly And Organization In The Extracellular Matrix," Connective Tissue And Its Heritable Disorders, Molecular Genetics, And Medical Aspects, Royce, P. M. and B. Steinmann eds., Wiley-Liss, NY, pp. 103-147; and Prockop, D. J- and K. I. Kivirikko (1995) "Collagens: Molecular Biology, Diseases, and Potentials for Therapy," Annu. Rev. Biochem., 64:403-434.)

Type I collagen is the major fibrillar collagen of bone and skin comprising approximately 80-90% of an organism's total collagen. Type I collagen is the major structural macromolecule present in the extracellular matrix of multicellular organisms and comprises approximately 20% of total protein mass. Type I collagen is a heterotrimeric molecule comprising two $\alpha 1(I)$ chains and one $\alpha 2(I)$ chain, encoded by the COL1A1 and COL1A2 genes, respectively. Other collagen types are less abundant than type I collagen, and exhibit different distribution patterns. For example, type II collagen is the predominant collagen in cartilage and vitreous humor, while type III collagen is found at high levels in blood vessels and to a lesser extent in skin.

Type II collagen is a homotrimeric collagen comprising three identical $\alpha 1(II)$ chains encoded by the COL2A1 gene. Purified type II collagen may be prepared from tissues by, methods known in the art, for example, by procedures described in Miller and Rhodes (1982) Methods In Enzymology 82:33-64.

Type III collagen is a major fibrillar collagen found in skin and vascular tissues. Type III collagen is a homotrimeric collagen comprising three identical $\alpha 1(III)$ chains encoded by the COL3A1 gene. Methods for purifying type III collagen from tissues can be found in, for example, Byers et al. (1974) Biochemistry 13:5243-5248; and Miller and Rhodes, supra.

Type IV collagen is found in basement membranes in the form of sheets rather than fibrils. Most commonly, type IV collagen contains two $\alpha 1(IV)$ chains and one $\alpha 2(IV)$ chain. The particular chains comprising type IV collagen are tissue-specific. Type IV collagen may be purified using, for example, the procedures described in Furuto and Miller (1987) Methods in Enzymology, 144:41-61, Academic Press.

Type V collagen is a fibrillar collagen found in, primarily, bones, tendon, cornea, skin, and blood vessels. Type V collagen exists in both homotrimeric and heterotrimeric forms. One form of type V collagen is a heterotrimer of two $\alpha 1(V)$ chains and one $\alpha 2(V)$ chain. Another form of type V collagen is a heterotrimer of $\alpha 1(V)$, $\alpha 2(V)$, and $\alpha 3(V)$ chains. A further form of type V collagen is a homotrimer of $\alpha 1(V)$. Methods for isolating type V collagen from natural sources can be found, for example, in Elstow and Weiss (1983) Collagen Rel. Res. 3:181-193, and Abedin et al. (1982) Biosci. Rep. 2:493-502.

Type VI collagen has a small triple helical region and two large non-collagenous remainder portions. Type VI collagen is a heterotrimer comprising $\alpha 1(VI)$, $\alpha 2(VI)$, and $\alpha 3(VI)$ chains. Type VI collagen is found in many connective tissues. Descriptions of how to purify type VI collagen from natural sources can be found, for example, in Wu et al. (1987) Biochem. J. 248:373-381, and Kielty et al. (1991) J. Cell Sci. 99:797-807.

Type VII collagen is a fibrillar collagen found in particular epithelial tissues. Type VII collagen is a homotrimeric molecule of three al (VII) chains. Descriptions of how to purify type VII collagen from tissue can be found in, for example, Lunstrum et al. (1986) J. Biol. Chem. 261:9042-9048, and Bentz et al. (1983) Proc. Natl. Acad. Sci. USA 80:3168-3172. Type VIII collagen can be found in Descemet's membrane in the cornea. Type VIII collagen is a heterotrimer comprising two $\alpha 1(VIII)$ chains and one $\alpha 2(VIII)$ chain, although other chain compositions have been reported. Methods for the purification of type VIII collagen from nature can be found, for example, in Benya and Padilla (1986) J. Biol. Chem. 261:4160-4169, and Kapoor et al, (1986) Biochemistry 25:3930-3937.

Type IX collagen is a fibril-associated collagen found in cartilage and vitreous humor. Type IX collagen is a heterotrimeric molecule comprising $\alpha 1(IX)$, $\alpha 2(IX)$, and $\alpha 3(IX)$ chains. Type IX collagen has been classified as a FACIT (Fibril Associated Collagens with Interrupted Triple Helices) collagen, possessing several triple helical domains separated by non-triple helical domains. Procedures for purifying type IX collagen can be found, for example, in Duance, et al. (1984) Biochem. J. 221:885-889; Ayad et al. (1989) Biochem. J. 262:753-761; and Grant et al. (1988) The Control of Tissue Damage, Glauert, A. M., ed., Elsevier Science Publishers, Amsterdam, pp. 3-28.

Type X collagen is a homotrimeric compound of $\alpha 1(X)$ chains. Type X collagen has been isolated from, for example, hypertrophic cartilage found in growth plates; see, e.g., Apte et al. (1992) Eur J Biochem 206 (1):217-24.

Type XI collagen can be found in cartilaginous tissues associated with type II and type IX collagens, and in other locations in the body. Type XI collagen is a heterotrimeric molecule comprising $\alpha 1(XI)$, $\alpha 2(XI)$, and $\alpha 3(XI)$ chains. Methods for purifying type XI collagen can be found, for example, in Grant et al., supra.

Type XII collagen is a FACIT collagen found primarily in association with type I collagen. Type XII collagen is a homotrimeric molecule comprising three $\alpha 1(XII)$ chains. Methods for purifying type XII collagen and variants thereof can be found, for example, in Dublet et al. (1989) J. Biol. Chem. 264:13150-13156; Lunstrum et al. (1992) J. Biol. Chem. 267:20087-20092; and Watt et al. (1992) J. Biol. Chem. 267:20093-20099.

Type XIII is a non-fibrillar collagen found, for example, in skin, intestine, bone, cartilage, and striated muscle. A detailed description of type XIII collagen may be found, for example, in Juvonen et al. (1992) J. Biol. Chem. 267: 24700-24707.

Type XIV is a FACIT collagen characterized as a homotrimeric molecule comprising α1(XIV) chains. Methods for isolating type XIV collagen can be found, for example, in Aubert-Foucher et al. (1992) J. Biol. Chem. 267:15759-15764, and Watt et al., supra.

Type XV collagen is homologous in structure to type XVIII collagen. Information about the structure and isolation of natural type XV collagen can be found, for example, in Myers et al. (1992) Proc. Natl. Acad. Sci. USA 89:10144-10148; Huebner et al. (1992) Genomics 14:220-224; Kivirikko et al. (1994) J. Biol. Chem. 269:4773-4779; and Muragaki, J. (1994) Biol. Chem. 264:4042-4046.

Type XVI collagen is a fibril-associated collagen, found, for example, in skin, lung fibroblast, and keratinocytes. Information on the structure of type XVI collagen and the gene encoding type XVI collagen can be found, for example, in Pan et al. (1992) Proc. Natl. Acad. Sci. USA 89:6565-6569; and Yamaguchi et al. (1992) J. Biochem. 112:856-863.

Type XVII collagen is a hemidesmosal transmembrane collagen, also known at the bullous pemphigoid antigen. Information on the structure of type XVII collagen and the gene encoding type XVII collagen can be found, for example, in Li et al. (1993) J. Biol. Chem. 268(12):8825-8834; and McGrath et al. (1995) Nat. Genet. 11(1):83-86.

Type XVIII collagen is similar in structure to type XV collagen and can be isolated from the liver. Descriptions of the structures and isolation of type XVIII collagen from natural sources can be found, for example, in Rehn and Pihiajaniemi (1994) Proc. Natl. Acad. Sci USA 91:4234-4238; Oh et al. (1994) Proc. Natl. Acad. Sci USA 91:4229-4233; Rehn et al. (1994) J. Biol. Chem. 269:13924-13935; and Oh et al. (1994) Genomics 19:494-499.

Type XIX collagen is believed to be another member of the FACIT collagen family, and has been found in mRNA isolated from rhabdomyosarcoma cells. Descriptions of the structures and isolation of type XIX collagen can be found, for example, in Inoguchi et al. (1995) J. Biochem. 117:137-146; Yoshioka et al. (1992) Genomics 13:884-886; and Myers et al., J. Biol. Chem. 289:18549-18557 (1994).

Type XX collagen is a newly found member of the FACIT collagenous family, and has been identified in chick cornea. (See, e.g., Gordon et al. (1999) FASEB Journal 13:A1119; and Gordon et al. (1998), IOVS 39:S1128.)

Any type of collagen, truncated collagen, unmodified or post-translationally modified, or amino acid sequence-modified collagen that can be fibrillated and crosslinked by the methods described herein can be used to produce a biofabricated material or biofabricated leather. Biofabricated leather may contain a substantially homogenous collagen, such as only Type I or Type III collagen or may contain mixtures of 2, 3, 4 or more different kinds of collagens.

Recombinant Collagen. Recombinant expression of collagen and collagen-like proteins is known and is incorporated by reference to Bell, EP 1232182B1, Bovine collagen and method for producing recombinant gelatin; Olsen, et al., U.S. Pat. No. 6,428,978, Methods for the production of gelatin and full-length triple helical collagen in recombinant cells; VanHeerde, et al., U.S. Pat. No. 8,188,230, Method for recombinant microorganism expression and isolation of collagen-like polypeptides. Such recombinant collagens have not been used to produce leather.

Prokaryotic expression. In prokaryotic systems, such as bacterial systems, a number of expression vectors may be advantageously selected depending upon the use intended for the expressed polypeptide. For example, when large quantities of the animal collagens and gelatins of the invention are to be produced, such as for the generation of antibodies, vectors which direct the expression of high levels of fusion protein products that are readily purified may be desirable. Such vectors include, but are not limited to, the E. coli expression vector pUR278 (Ruther et al. (1983) EMBO J. 2:1791), in which the coding sequence may be ligated into the vector in frame with the lac Z coding region so that a hybrid AS-lacZ protein is produced; pIN vectors (Inouye et al. (1985) Nucleic Acids Res. 13:3101-3109 and Van Heeke et al. (1989) J. Biol. Chem. 264:5503-5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety. A recombinant collagen may comprise collagen molecules that have not been post-translationally modified, e.g., not glycosylated or hydroxylated, or may comprise one or more post-translational modifications, for example, modifications that facilitate fibrillation and formation of unbundled and randomly oriented fibrils of collagen molecules.

A recombinant collagen molecule can comprise a fragment of the amino acid sequence of a native collagen molecule that can form trimeric collagen fibrils or a modified collagen molecule or truncated collagen molecule having an amino acid sequence at least 70, 80, 90, 95, 96, 97, 98, or 99% identical or similar to a native collagen amino acid sequence (or to a fibril forming region thereof or to a segment substantially comprising [Gly-X-Y]$_n$), such as those of bovine collagen, described by SEQ ID NOS: 1, 2 or 3 and by amino acid sequences of Col1A1, Col1A2, and Col1A3, described by Accession Nos. NP_001029211.1, NP_776945.1 and NP_001070299.1 which are incorporated by reference.

Such recombinant or modified collagen molecules will generally comprise the repeated -(Gly-X-Y)$_n$— sequence described herein.

BLASTN may be used to identify a polynucleotide sequence having at least 70%, 75%, 80%, 85%, 87.5%, 90%, 92.5%, 95%, 97.5%, 98%, or 99% sequence identity to a reference polynucleotide such as a polynucleotide encoding a collagen polypeptide or encoding the amino acid sequences of SEQ ID NOS: 1, 2 or 3. A representative BLASTN setting optimized to find highly similar sequences uses an Expect Threshold of 10 and a Wordsize of 28, max matches in query range of 0, match/mismatch scores of 1/-2, and linear gap cost. Low complexity regions may be filtered or masked. Default settings of a Standard Nucleotide BLAST are known.

BLASTP can be used to identify an amino acid sequence having at least 70%, 75%, 80%, 85%, 87.5%, 90%, 92.5%, 95%, 97.5%, 98%, or 99% sequence identity, or similarity to a reference amino acid, such as a collagen amino acid sequence, using a similarity matrix such as BLOSUM45. BLOSUM62 or BLOSUM80 where BLOSUM45 can be used for closely related sequences, BLOSUM62 for mid-range sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting that uses an Expect Threshold of 10, a Word Size of 3, BLOSUM 62 as a matrix, and Gap Penalty of 11 (Existence) and 1 (Extension) and a conditional compositional score matrix adjustment.

Yeast expression. In one embodiment, collagen molecules are produced in a yeast expression system. In yeast, a number of vectors containing constitutive or inducible promoters known in the art may be used; Ausubel et al., supra, Vol. 2, Chapter 13; Grant et al. (1987) Expression and Secretion Vectors for Yeast, in Methods in Enzymology, Ed, Wu & Grossman, Acad. Press, N.Y. 153:516-544; Glover (1986) DNA Cloning, Vol. II, IRL Press, Wash., D.C., Ch. 3; Bitter (1987) Heterologous Gene Expression in Yeast, in Methods in Enzymology, Eds. Berger & Kimmel, Acad. Press, N.Y. 152:673-684; and The Molecular Biology of the Yeast Saccharomyces, Eds. Strathern et al., Cold Spring Harbor Press, Vols. I and II (1982).

Collagen can be expressed using host cells, for example, from the yeast *Saccharomyces cerevisiae*. This particular yeast can be used with any of a large number of expression vectors. Commonly employed expression vectors are shuttle vectors containing the 2P origin of replication for propagation in yeast and the Col E1 origin for *E. coli*, for efficient transcription of the foreign gene. A typical example of such vectors based on 2P plasmids is pWYG4, which has the 2P ORI-STB elements, the GAL1-10 promoter, and the 2P D gene terminator. In this vector, an NcoI cloning site is used to insert the gene for the polypeptide to be expressed, and to provide the ATG start codon. Another expression vector is pWYG7L, which has intact 2αORI, STB, REP1 and REP2, and the GAL1-10 promoter, and uses the FLP terminator. In this vector, the encoding polynucleotide is inserted in the polylinker with its 5' ends at a BamHI or NcoI site. The vector containing the inserted polynucleotide is transformed into *S. cerevisiae* either after removal of the cell wall to produce spheroplasts that take up DNA on treatment with calcium and polyethylene glycol or by treatment of intact cells with lithium ions.

Alternatively, DNA can be introduced by electroporation. Transformants can be selected, for example, using host yeast cells that are auxotrophic for leucine, tryptophan, uracil, or histidine together with selectable marker genes such as LEU2, TRP1, URA3, HIS3, or LEU2-D.

In one embodiment, polynucleotides encoding collagen are introduced into host cells from the yeast *Pichia*. Species of non-Saccharomyces yeast such as *Pichia pastoris* appear to have special advantages in producing high yields of recombinant protein in scaled up procedures. Additionally, a *Pichia* expression kit is available from Invitrogen Corporation (San Diego, Calif.).

There are a number of methanol responsive genes in methylotrophic yeasts such as *Pichia pastoris*, the expression of each being controlled by methanol responsive regulatory regions, also referred to as promoters. Any of such methanol responsive promoters are suitable for use in the practice of the present invention. Examples of specific regulatory regions include the AOX1 promoter, the AOX2 promoter, the dihydroxyacetone synthase (DAS), the P40 promoter, and the promoter for the catalase gene from *P. pastoris*, etc.

In other embodiments, the methylotrophic yeast *Hansenula polymorpha* is used. Growth on methanol results in the induction of key enzymes of the methanol metabolism, such as MOX (methanol oxidase), DAS (dihydroxyacetone synthase), and FMHD (formate dehydrogenase). These enzymes can constitute up to 30-40% of the total cell protein. The genes encoding MOX, DAS, and FMDH production are controlled by strong promoters induced by growth on methanol and repressed by growth on glucose. Any or all three of these promoters may be used to obtain high-level expression of heterologous genes in *H. polymorpha*. Therefore, in one aspect, a polynucleotide encoding animal collagen or fragments or variants thereof is cloned into an expression vector under the control of an inducible *H. polymorpha* promoter. If secretion of the product is desired, a polynucleotide encoding a signal sequence for secretion in yeast is fused in frame with the polynucleotide. In a further embodiment, the expression vector preferably contains an auxotrophic marker gene, such as URA3 or LEU2, which may be used to complement the deficiency of an auxotrophic host.

The expression vector is then used to transform *H. polymorpha* host cells using techniques known to those of skill in the art. A useful feature of *H. polymorpha* transformation is the spontaneous integration of up to 100 copies of the expression vector into the genome. In most cases, the integrated polynucleotide forms multimers exhibiting a head-to-tail arrangement. The integrated foreign polynucleotide has been shown to be mitotically stable in several recombinant strains, even under non-selective conditions. This phenomena of high copy integration further ads to the high productivity potential of the system.

Fungal Expression. Filamentous fungi may also be used to produce the present polypeptides. Vectors for expressing and/or secreting recombinant proteins in filamentous fungi are well known, and one of skill in the art could use these vectors to express the recombinant animal collagens of the present invention.

Plant Expression. In one aspect, an animal collagen is produced in a plant or plant cells. In cases where plant expression vectors are used, the expression of sequences encoding the collagens of the invention may be driven by any of a number of promoters. For example, viral promoters such as the 35S RNA and 19S RNA promoters of CaMV (Brisson et al. (1984) Nature 310:511-514), or the coat protein promoter of TMV (Takamatsu et al. (1987) EMBO J. 6:307-311) may be used; alternatively, plant promoters such as the small subunit of RUBISCO (Coruzzi et al. (1984) EMBO J. 3:1671-1680; Broglie et al. (1984) Science 224:838-843) or heat shock promoters, e.g., soybean hsp17.5-E or hsp17.3-B (Gurley et al. (1986) Mol. Cell. Biol. 6:559-565) may be used. These constructs can be introduced into plant cells by a variety of methods known to those of skill in the art, such as by using Ti plasmids, Ri plasmids, plant virus vectors, direct DNA transformation, microinjection, electroporation, etc. For reviews of such techniques see, for example, Weissbach & Weissbach, Methods for Plant Molecular Biology, Academic Press, NY, Section VIII, pp. 421-463 (1988); Grierson & Corey, Plant Molecular Biology, 2d Ed., Blackie, London, Ch. 7-9 (1988); Transgenic Plants: A Production System for Industrial and Pharmaceutical Proteins, Owen and Pen eds., John Wiley & Sons, 1996; Transgenic Plants, Galun and Breiman eds, Imperial College Press, 1997; and Applied Plant Biotechnology, Chopra, Malik, and Bhat eds., Science Publishers, Inc., 1999.

Plant cells do not naturally produce sufficient amounts of post-translational enzymes to efficiently produce stable collagen. Therefore, where hydroxylation is desired, plant cells used to express animal collagens are supplemented with the necessary post-translational enzymes to sufficiently produce stable collagen. In a preferred embodiment of the present invention, the post-translational enzyme is prolyl 4-hydroxylase.

Methods of producing the present animal collagens in plant systems may be achieved by providing a biomass from plants or plant cells, wherein the plants or plant cells comprise at least one coding sequence is operably linked to a promoter to effect the expression of the polypeptide, and the polypeptide is then extracted from the biomass. Alternatively, the polypeptide can be non-extracted, e.g., expressed into the endosperm.

Plant expression vectors and reporter genes are generally known in the art; see, e.g., Gruber et al. (1993) in *Methods of Plant Molecular Biology and Biotechnology*, CRC Press. Typically, the expression vector comprises a nucleic acid construct generated, for example, recombinantly or synthetically, and comprising a promoter that functions in a plant cell, wherein such promoter is operably linked to a nucleic acid sequence encoding an animal collagen or fragments or variants thereof, or a post-translational enzyme important to the biosynthesis of collagen.

Promoters drive the level of protein expression in plants. To produce a desired level of protein expression in plants, expression may be under the direction of a plant promoter. Promoters suitable for use in accordance with the present invention are generally available in the art; see, e.g., PCT Publication No. WO 91/19806. Examples of promoters that may be used in accordance with the present invention include non-constitutive promoters or constitutive promoters. These promoters include, but are not limited to, the promoter for the small subunit of ribulose-1,5-bis-phosphate carboxylase; promoters from tumor-inducing plasmids of *Agrobacterium tumefaciens*, such as the RUBISCO nopaline synthase (NOS) and octopine synthase promoters; bacterial T-DNA promoters such as mas and ocs promoters; and viral promoters such as the cauliflower mosaic virus (CaMV) 19S and 35S promoters or the figwort mosaic virus 35S promoter.

The polynucleotide sequences of the present invention can be placed under the transcriptional control of a constitutive promoter, directing expression of the collagen or post-translational enzyme in most tissues of a plant. In one embodiment, the polynucleotide sequence is under the control of the cauliflower mosaic virus (CaMV) 35S promoter. The double stranded caulimorvirus family has provided the single most important promoter expression for transgene expression in plants, in particular, the 35S promoter; see, e.g., Kay et al. (1987) Science 236:1299. Additional promoters from this family such as the figwort mosaic virus promoter, etc., have been described in the art, and may also be used; see, e.g., Sanger et al. (1990) Plant Mol. Biol. 14:433-443; Medberry et al. (1992) Plant Cell 4:195-192; and Yin and Beachy (1995) Plant J. 7:969-980.

The promoters used in polynucleotide constructs for expressing collagen may be modified, if desired, to affect their control characteristics. For example, the CaMV promoter may be ligated to the portion of the RUBISCO gene that represses the expression of RUBISCO in the absence of light, to create a promoter which is active in leaves, but not in roots. The resulting chimeric promoter may be used as described herein.

Constitutive plant promoters having general expression properties known in the art may be used with the expression vectors of the present invention. These promoters are abundantly expressed in most plant tissues and include, for example, the actin promoter and the ubiquitin promoter; see, e.g., McElroy et al. (1990) Plant Cell 2:163-171; and Christensen et al. (1992) Plant Mol. Biol. 18:675-689.

Alternatively, the polypeptide of the present invention may be expressed in a specific tissue, cell type, or under more precise environmental conditions or developmental control. Promoters directing expression in these instances are known as inducible promoters. In the case where a tissue-specific promoter is used, protein expression is particularly high in the tissue from which extraction of the protein is desired. Depending on the desired tissue, expression may be targeted to the endosperm, aleurone layer, embryo (or its parts as scutellum and cotyledons), pericarp, stem, leaves tubers, roots, etc. Examples of known tissue-specific promoters include the tuber-directed class I patatin promoter, the promoters associated with potato tuber ADPGPP genes, the soybean promoter of β-conglycinin (7S protein) which drives seed-directed transcription, and seed-directed promoters from the zein genes of maize endosperm; see, e.g., Bevan et al. (1986) Nucleic Acids Res, 14: 4625-38; Muller et al. (1990) Mol. Gen. Genet. 224:136-46; Bray (1987) Planta 172: 364-370; and Pedersen et al. (1982) Cell 29:1015-26.

Collagen polypeptides can be produced in seed by way of seed-based production techniques using, for example, canola, corn, soybeans, rice and barley seed. In such a process, for example, the product is recovered during seed germination; see, e.g., PCT Publication Numbers WO 9940210; WO 9916890; WO 9907206; U.S. Pat. Nos. 5,866, 121; 5,792,933; and all references cited therein. Promoters that may be used to direct the expression of the polypeptides may be heterologous or non-heterologous. These promoters can also be used to drive expression of antisense nucleic acids to reduce, increase, or alter concentration and composition of the present animal collagens in a desired tissue.

Other modifications that may be made to increase and/or maximize transcription of the present polypeptides in a plant or plant cell are standard and known to those in the art. For example a vector comprising a polynucleotide sequence encoding a recombinant animal collagen, or a fragment or variant thereof, operably linked to a promoter may further comprise at least one factor that modifies the transcription rate of collagen or related post-translational enzymes, including, but not limited to, peptide export signal sequence, codon usage, introns, polyadenylation, and transcription termination sites. Methods of modifying constructs to increase expression levels in plants are generally known in the art; see, e.g. Rogers et al. (1985) J. Biol. Chem. 260: 3731; and Cornejo et al. (1993) Plant Mol Biol 23:567-58. In engineering a plant system that affects the rate of transcription of the present collagens and related post-translational enzymes, various factors known in the art, including regulatory sequences such as positively or negatively acting sequences, enhancers and silencers, as well as chromatin structure can affect the rate of transcription in plants. At least one of these factors may be utilized when expressing a recombinant animal collagen, including but not limited to the collagen types described above.

The vectors comprising the present polynucleotides will typically comprise a marker gene which confers a selectable phenotype on plant cells. Usually, the selectable marker gene will encode antibiotic resistance, with suitable genes including at least one set of genes coding for resistance to the antibiotic spectinomycin, the streptomycin phophotransferase (SPT) gene coding for streptomycin resistance, the neomycin phophotransferase (NPTH) gene encoding kanamycin or geneticin resistance, the hygromycin resistance, genes coding for resistance to herbicides which act to inhibit the action of acetolactate synthase (ALS), in particular, the sulfonylurea-type herbicides; e.g., the acetolactate synthase (ALS) gene containing mutations leading to such resistance in particular the S4 and/or Hra mutations, genes coding for resistance to herbicides which act to inhibit action of glutamine synthase, such as phophinothricin or basta; e.g. the bar gene, or other similar genes known in the art. The bar gene encodes resistance to the herbicide basta, the nptII gene encodes resistance to the antibiotics kanamycin and geneticin, and the ALS gene encodes resistance to the herbicide chlorsulfuron.

Typical vectors useful for expression of foreign genes in plants are well known in the art, including, but not limited to, vectors derived from the tumor-inducing (Ti) plasmid of *Agrobacterium tumefaciens*. These vectors are plant integrating vectors that upon transformation, integrate a portion of the DNA into the genome of the host plant; see e.g., Rogers et al. (1987) Meth In Enzymol. 153:253-277; Schardl et al. (1987) Gene 61:1-11; and Berger et al., Proc. Natl. Acad. Sci. U.S.A. 86:8402-8406.

Vectors comprising sequences encoding the present polypeptides and vectors comprising post-translational enzymes or subunits thereof may be co-introduced into the desired plant. Procedures for transforming plant cells are available in the art, for example, direct gene transfer, in vitro protoplast transformation, plant virus-mediated transformation, liposome-mediated transformation, microinjection, electroporation, *Agrobacterium* mediated transformation, and particle bombardment; see e.g., Paszkowski et al. (1984) EMBO J. 3:2717-2722; U.S. Pat. No. 4,684,611; European Application No. 0 67 553; U.S. Pat. Nos. 4,407,956; 4,536,475; Crossway et al. (1986) Biotechniques 4:320-334; Riggs et al. (1986) Proc. Natl. Acad. Sci USA 83:5602-5606; Hinchee et al. (1988) Biotechnology 6:915-921; and U.S. Pat. No. 4,945,050.) Standard methods for the transformation of, e.g., rice, wheat, corn, sorghum, and barley are described in the art; see, e.g., Christou et al. (1992) Trends in Biotechnology 10: 239 and Lee et al. (1991) Proc. Nat'l Acad. Sci. USA 88:6389. Wheat can be transformed by techniques similar to those employed for transforming corn or rice. Furthermore, Casas et al. (1993) Proc. Nat'l Acad. Sci. USA 90:11212, describe a method for transforming sorghum, while Wan et al. (1994) Plant Physiol. 104: 37, teach a method for transforming barley. Suitable methods for corn transformation are provided by Fromm et al. (1990) Bio/Technology 8:833 and by Gordon-Kamm et al., supra.

Additional methods that may be used to generate plants that produce animal collagens of the present invention are established in the art; see, e.g., U.S. Pat. Nos. 5,959,091; 5,859,347; 5,763,241; 5,659,122; 5,593,874; 5,495,071; 5,424,412; 5,362,865; 5,229,112; 5,981,841; 5,959,179; 5,932,439; 5,869,720; 5,804,425; 5,763,245; 5,716,837; 5,689,052; 5,633,435; 5,631,152; 5,627,061; 5,602,321; 5,589,612; 5,510,253; 5,503,999; 5,378,619; 5,349,124; 5,304,730; 5,185,253; 4,970,168; European Publication No. EPA 00709462; European Publication No. EPA 00578627; European Publication No. EPA 00531273; European Publication No. EPA 00426641; PCT Publication No, WO 99/31248; PCT Publication No. WO 98/58069; PCT Publication No. WO 98/45457; PCT Publication No. WO 98/31812; PCT Publication No. WO 98/08962; PCT Publication No. WO 97/48814; PCT Publication No. WO 97/30582; and PCT Publication No. WO 9717459.

Insect Expression. Another alternative expression system for collagen is an insect system. Baculoviruses are very efficient expression vectors for the large scale production of various recombinant proteins in insect cells. The methods as described in Luckow et al. (1989) Virology 170:31-39 and Gruenwald, S. and Heitz, J. (1993) Baculovirus Expression Vector System: Procedures & Methods Manual, Pharmingen, San Diego, Calif., can be employed to construct expression vectors containing a collagen coding sequence for the collagens of the invention and the appropriate transcriptional/translational control signals. For example, recombinant production of proteins can be achieved in insect cells, by infection of baculovirus vectors encoding the polypeptide. The production of recombinant collagen, collagen-like or collagenous polypeptides with stable triple helices can involve the co-infection of insect cells with three baculoviruses, one encoding the animal collagen to be expressed and one each encoding the α subunit and β subunit of prolyl 4-hydroxylase. This insect cell system allows for production of recombinant proteins in large quantities. In one such system, *Autographa californica* nuclear polyhidrosis virus (AcNPV) is used as a vector to express foreign genes. This virus grows in *Spodoptera frugiperda* cells. Coding sequences for collagen or collagen-like polypeptides may be cloned into non-essential regions (for example the polyhedron gene) of the virus and placed under control of an AcNPV promoter (for example, the polyhedron promoter). Successful insertion of a coding sequence will result in inactivation of the polyhedron gene and production of non-occluded recombinant virus; e.g., viruses lacking the proteinaceous coat coded for by the polyhedron gene. These recombinant viruses are then used to infect *Spodoptera frugiperda* cells in which the inserted gene is expressed; see, e.g., Smith et al. (1983) J. Virol. 46:584; and U.S. Pat. No. 4,215,051. Further examples of this expression system may be found in, for example, Ausubel et al, above.

Animal Expression. In animal host cells, a number of expression systems may be utilized. In cases where an adenovirus is used as an expression vector, polynucleotide sequences encoding collagen or collagen-like polypeptides may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the encoded polypeptides in infected hosts; see, e.g., Logan & Shenk, Proc. Natl. Acad. Sci, USA 81:3655-3659 (1984). Alternatively, the vaccinia 7.5 K promoter may be used; see, e.g., Mackett et al. (1982) Proc. Natl. Acad. Sci. USA 79:7415-7419; Mackett et al. (1982) J. Virol. 49:857-864; and Panicali et al. (1982) Proc. Natl. Acad. Sci. USA 79:4927-4931.

A preferred expression system in mammalian host cells is the Semliki Forest virus. Infection of mammalian host cells, for example, baby hamster kidney (BHK) cells and Chinese hamster ovary (CHO) cells can yield very high recombinant expression levels. Semliki Forest virus is a preferred expression system as the virus has a broad host range such that infection of mammalian cell lines will be possible. More specifically, Semliki Forest virus can be used in a wide range of hosts, as the system is not based on chromosomal integration, and thus provides an easier way of obtaining modifications of the recombinant animal collagens in studies aiming at identifying structure function relationships and testing the effects of various hybrid molecules. Methods for constructing Semliki Forest virus vectors for expression of exogenous proteins in mammalian host cells are described in, for example, Olkkonen et al. (1994) Methods Cell Biol 43:43-53.

Non-human transgenic animals may also be used to express the polypeptides of the present invention. Such systems can be constructed by operably linking the polynucleotide of the invention to a promoter, along with other required or optional regulatory sequences capable of effecting expression in mammary glands. Likewise, required or optional post-translational enzymes may be produced simultaneously in the target cells employing suitable expression systems. Methods of using non-human transgenic animals to recombinantly produce proteins are known in the art; see, e.g., U.S. Pat. Nos. 4,736,866; 5,824,838; 5,487,992; and 5,614,396.

The references cited in the sections above which describe the production of recombinant collagens are each incorporated by reference.

Composite collagen fiber sheets. As shown in FIG. 1, triple helical collagen molecules associate into fibrils which in animal skin assemble into larger fibril bundles or collagen fibers. Prior methods of making collagen sheets used a mixture of ground animal skin or leather scraps and dissolved or suspended collagen. Such collagen fiber-containing products are described by U.S. Pat. Nos. 2,934,446; 3,073,714; 3,122, 599; and 3,136,682. Highberger, et al., U.S. Pat. No. 2,934,446 describes a method using a meat grinder to produce a slurry of calfskin hide or corium which is formed into a sheet, tanned and for forming interlocked collagen fiber masses by comminuting and dispersing animal skin in an acidic aqueous solution at 5° C. and then raising the pH and temperature to precipitate collagen fibers to form a gel which is then dried. These sheets of collagen fiber masses make use of leather scraps and form sheets resembling leather. Highberger does not show that these leather sheets are suitable for commercial use. Tu, et al., U.S. Pat. No. 3,073,714 discloses producing a sheet from an calfskin slurry containing 25% solids which is tanned with a vegetable tanning solution and treated with glycerin and oleic acid. These collagen fiber sheets are described as reproducing the internal arrangement of collagen fibers in natural skins and hides. Tu does not show that the leather sheets are compositionally or aesthetically suitable for use in a consumer product. Tu, et al., U.S. Pat. No. 3,122,599 describes a leather-like sheet made from ground animal skin or leather which contains collagen fibers and soluble collagen as well as other components derived from the animal skin. Tu discloses treating this mixture with chromium, dehydrating it with acetone, and treating with oleic acid to produce a leather-like product containing collagen fiber masses. Tu does not show that the sheet is compositionally, physically or aesthetically suitable for use in a consumer product. Tu, et al., U.S. Pat. No. 3,136,682 describes a process of making a leather-like material that contains a mixture of collagen fibers and a binder of water-soluble proteinaceous material derived from animal skin. It also describes the use of a chromium tanning agent and treatment with oleic acid. Tu describes a sheet of good appearance and feel, but does not show that it is suitable for incorporation into a consumer product. These products incorporate coarse, ground or digested collagen fibers.

Cultured leather products. These products generally comprise a plurality of layers containing collagen produced by culturing cells in vitro are described by Forgacs, et al., U.S. 2016/0097109 A1 and by Greene, U.S. Pat. No. 9,428,817 B2. These products are produced in vitro by cultivation of cell explants or cultured collagen-producing cells. Such cells produce and process collagen into quaternary bundles of collagen fibrils and do not have the random, non-antistrophic structure of the collagen fibrils of the invention. Forgacs describes engineered animal skins, which may be shaped, to produce a leather product. Green describes a variety of products, such as footwear, apparel and luggage that may incorporate leather that is cultured in vitro. US 2013/0255003 describes producing collagen for leather-like products by growing bovine skin cells in culture. Other types of host cells have been utilized to produce collagen for medical implants or to produce gelatin. For example, United States Patent Application US 2004/0018592 describes a way to produce gelatin by recombinantly expressing bovine collagen in host cells, such as yeast.

Medical products. Networks of collagen have been produced in vitro as materials for biomedical applications. In those applications, monomers of the collagen triple helix are extracted from animal tissue, such as bovine dermis, either by acid treatment or treatment with protein degrading enzymes such as pepsin, to solubilize collagen from the tissue. Once purified, these solubilized collagens (often mixtures of monomers, dimers and trimers of the collagen triple helix) can be fibrillated into fibrils through a pH shift in aqueous buffers. Under the right conditions, the collagen monomers self-assemble into fibrils, and depending on their source and how they were isolated, the fibrils can physically crosslink to form a solid hydrogel. In addition, recombinant collagens and collagen-like proteins have been shown to fibrillate in vitro through similar adjustments in pH and salt concentration. Examples of such products for medical applications include a biodegradable collagen matrix made from a collagen slurry that self-assembles into macroscopic collagen fibers, U.S. Pat. No. 9,539,363, and an organized array of collagen fibrils produced by use of external guidance structures or internal templates and the application of tension, U.S. Pat. No. 9,518,106. Collagen products used in medicine, such as for tissue engineering or grafting, often aim to provide collagen in a form similar to that in a particular tissue being engineered or repaired. While fibrillation of soluble collagens and collagen-like proteins has been explored to produce collagen hydrogels for biomedical applications, this technology has not been successfully applied to the production of a material having the strength and aesthetic properties of natural leather.

Synthetic plastic-based leathers. Attempts to create synthetic leather have come up short in reproducing leather's unique set of functional and aesthetic properties. Examples of synthetic leather materials include Clarino, Naugahyde®, Corfam, and Alcantara, amongst others. They are made of various chemical and polymer ingredients, including polyvinyl chloride, polyurethane, nitrocellulose coated cotton cloth, polyester, or other natural cloth or fiber materials coated with a synthetic polymer. These materials are assembled using a variety of techniques, often drawing from chemical and textile production approaches, including nonwoven and advanced spinning processes. While many of these materials have found use in footwear, upholstery, and apparel applications, they have fallen short for luxury application, as they cannot match the breathability, performance, hand feel, or aesthetic properties that make leather so unique and beloved. To date, no alternative commercial leather-like materials have been made from a uniform network of collagen or collagen-like proteins. Synthetic plastic materials lack the chemical composition and structure of a collagen network that produces an acceptable leather aesthetic. Unlike, synthetics, the chemical composition of amino acid side groups along the collagen polypeptide chain, along with its organization into a strong yet porous, fibrous architecture allow stabilization and functionalization of the fibril network through crosslinking processes to produce the desirable strength, softness and aesthetic of leather.

While fibrillation of soluble collagens and collagen-like proteins has been explored to bind together ground or comminuted leather scraps or for the production of collagen hydrogels for biomedical applications, harnessing this phenomenon to produce a commercially acceptable leather-like material has not been achieved.

In view of the problems with prior art natural leathers, and composite, cultured, and synthetic, plastic-based leather products the inventors diligently pursued a way to provide a biofabricated leather having superior strength and uniformity and non-anisotropic properties that incorporated natural components found in leather.

Described herein are materials composed of collagen fibrils fibrillated in vitro that have leather-like properties imparted by crosslinking, dehydration and lubrication. Compared to tanned and fatliquored animal hides, these biofabricated materials can have structural, compositional and functional uniformity, for example, advantageous substantially non-anisotropic strength and other mechanical properties as well as a top grain like aesthetic on both their top and bottom surfaces.

SUMMARY OF THE INVENTION

Among its other embodiments, the invention is directed to a biofabricated material composed of a network of crosslinked and lubricated collagen fibrils. It may be produced from collagen isolated from an animal source or recombinant collagen. It can be produced from collagens that contain substantially no residues. Preferably it is substantially free of large bundles of collagen fibers or other non-hydroxylysine collagen components of leather, such as elastin. This material is composed of collagen which is also a major component of natural leather and is produced by a process of fibrillation of collagen molecules into fibrils, crosslinking the fibrils and lubricating the crosslinked fibrils. Unlike natural leathers, this biofabricated material exhibits non-anisotropic (not directionally dependent) physical properties, for example, a sheet of biofabricated material can have substantially the same elasticity or tensile strength when measured in different directions. Unlike natural leather, it has a uniform texture that facilitates uniform uptake of dyes and coatings. Aesthetically, it produces a uniform and consistent grain for ease of manufacturability. It can have substantially identical grain, texture and other aesthetic properties on both sides unlike natural leathers where the grain increases from one side (e.g., distal surface) to the other (proximal inner layers).

BRIEF DESCRIPTION OF THE DRAWINGS

FIGS. 2B and 2C compare the textures and grains of the outer and inner surfaces of a leather depicting fine grain on one side and coarser corium on the other.

FIG. 3A is a scanning electron micrograph of the fibrillated collagen hydrogel showing a network of fine collagen fibrils.

FIG. 3B is a scanning electron micrograph of bovine corium showing coarser fiber bundles.

FIG. 4 is a transmission electron micrograph of a fibrillated collagen network or hydrogel showing fibril banding.

DETAILED DESCRIPTION OF THE INVENTION

Figure 1:
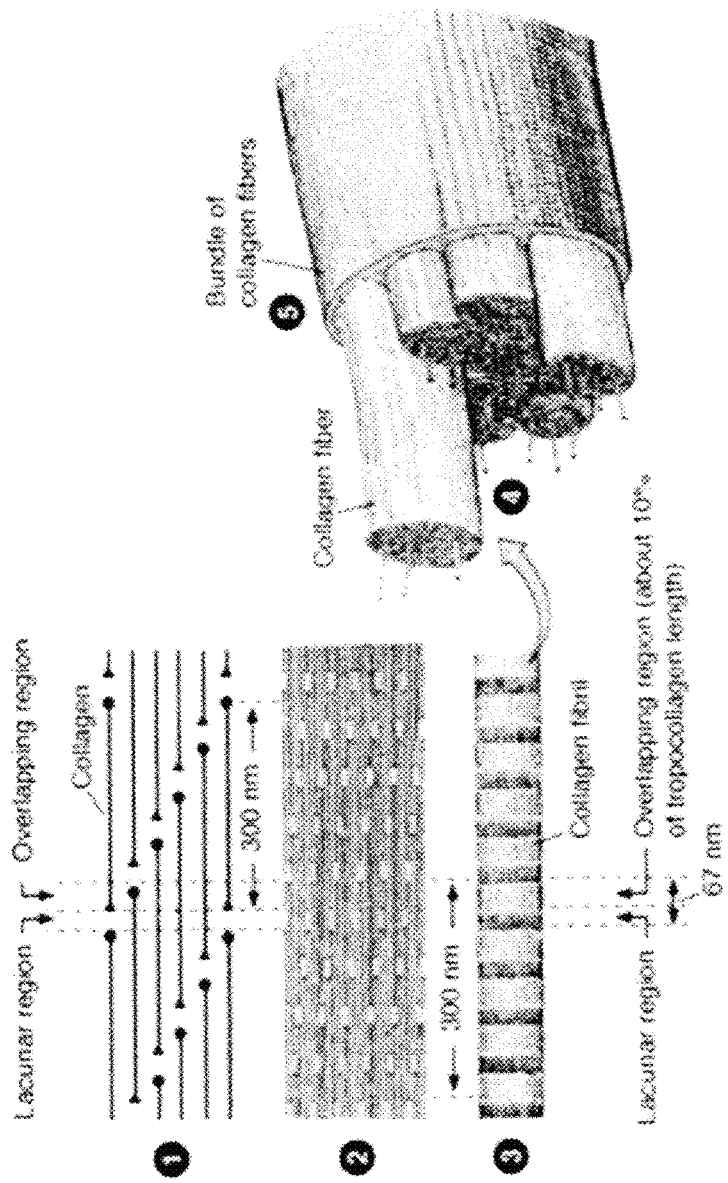
FIG. 1 is a drawing showing the composition of collagen in a hierarchical fashion. Reference character (1) shows each triple helical collagen monomer and how they are assembled with respect to neighboring collagen monomers; (2) shows assembled collagen that makes up banded collagen fibrils; (3) shows the collagen fibrils at larger scale; (4) shows collagen fibrils aligned into fibers; and (5) shows bundles of collagen fibers.

"Biofabricated material" or "biofabricated leather" as used herein is a material produced from collagen or a collagen-like protein. It can be produced from non-human collagens such as bovine, buffalo, ox, dear, sheep, goat, or pig collagen, which may be isolated from a natural source like animal hide, by in vitro culture of mammalian or animal cells, recombinantly produced or chemically synthesized. It is not a conventional material or leather which is produced from animal skins. Methods for producing this biofabricated material or biofabricated leather are disclosed herein and usually involve fibrillating an isolated or purified solution or suspension of collagen molecules to produce collagen fibrils, crosslinking the fibrils, dehydrating the fibrils and lubricating the fibrils.

In contrast to natural leathers which exhibit heterogeneous internal collagen structures, a biofabricated material or biofabricated leather can exhibit a substantially uniform internal structure characterized by unbundled and randomly-oriented collagen fibrils throughout its volume.

The resulting biofabricated material may be used in any way that natural leather is used and may be grossly similar in appearance and feel to real leather, while having compositional, functional or aesthetic features that differentiate it from ordinary leather. For example, unlike natural leather, a biofabricated leather need not contain potentially allergenic non-collagen proteins or components found in a natural leather, a biofabricated leather may exhibit a similar flexibility and strength in all directions (non-anisotropy) due to substantial non-alignment of its collagen fibrils, and aesthetically may have a smooth grain texture on both sides. A biofabricated leather can exhibit uniformity of properties including uniform thickness and consistency, uniform distribution of lubricants, crosslinkers and dyes, uniform non-anisotropic strength, stretch, flexibility and resistance to piping (or the tendency for natural leather to separate or split parallel to a plane of a sheet). By selecting the content of collagen and processing conditions, biofabricated leather can be "tuned" to a particular thickness, consistency, flexibility, softness, drape. surface texture or other functionality. Laminated, layered or composite products may comprise a biofabricated leather.

The term "collagen" refers to any one of the known collagen types, including collagen types I through XX, as well as to any other collagens, whether natural, synthetic, semi-synthetic, or recombinant. It includes all of the collagens, modified collagens and collagen-like proteins described herein. The term also encompasses procollagens and collagen-like proteins or collagenous proteins comprising the motif (Gly-X-Y)n where n is an integer. It encompasses molecules of collagen and collagen-like proteins, trimers of collagen molecules, fibrils of collagen, and fibers of collagen fibrils. It also refers to chemically, enzymatically or recombinantly-modified collagens or collagen-like molecules that can be fibrillated as well as fragments of collagen, collagen-like molecules and collagenous molecules capable of assembling into a nanofiber.

In some embodiments, amino acid residues, such as lysine and proline, in a collagen or collagen-like protein may lack hydroxylation or may have a lesser or greater degree of hydroxylation than a corresponding natural or unmodified collagen or collagen-like protein. In other embodiments, amino acid residues in a collagen or collagen-like protein may lack glycosylation or may have a lesser or greater degree of glycosylation than a corresponding natural or unmodified collagen or collagen-like protein.

The collagen in a collagen composition may homogenously contain a single type of collagen molecule, such as 100% bovine Type I collagen or 100% Type III bovine collagen, or may contain a mixture of different kinds of collagen molecules or collagen-like molecules, such as a mixture of bovine Type I and Type III molecules. Such mixtures may include >0%, 10, 20, 30, 40, 50, 60, 70, 80, 90, 95, 99 or <100% of the individual collagen or collagen-like protein components. This range includes all intermediate values. For example, a collagen composition may contain 30% Type I collagen and 70% Type III collagen, or may contain 33.3% of Type I collagen, 33.3% of Type II collagen, and 33.3% of Type III collagen, where the percentage of collagen is based on the total mass of collagen in the composition or on the molecular percentages of collagen molecules.

"Collagen fibrils" are nanofibers composed of tropocollagen (triple helices of collagen molecules). Tropocollagens also include tropocollagen-like structures exhibiting triple helical structures. The collagen fibrils of the invention may have diameters ranging from 1 nm and 1 µm. For example, the collagen fibrils of the invention may have an average or individual fibril diameter ranging from 1, 2, 3, 4, 5, 10, 15, 20, 30, 40, 50, 60, 70, 80, 90, 100, 200, 300, 400, 500, 600, 700, 800, 900, or 1,000 nm (1 µm). This range includes all intermediate values and subranges. In some of the embodiments of the invention collagen fibrils will form networks, for example, as depicted by FIGS. 3 and 4. Collagen fibrils can associate into fibrils exhibiting a banded pattern as shown in FIG. 1 and these fibrils can associate into larger aggregates of fibrils. In some embodiments the collagen or collagen-like fibrils will have diameters and orientations similar to those in the top grain or surface layer of a bovine or other conventional leather. In other embodiments, the collagen fibrils may have diameters comprising the top grain and those of a corium layer of a conventional leather.

A "collagen fiber" is composed of collagen fibrils that are tightly packed and exhibit a high degree of alignment in the direction of the fiber as shown in FIG. 1. It can vary in diameter from more than 1 µm to more than 10 µm, for example >1, 2, 3, 4, 5, 6, 7, 8, 9, 10, 11, 12 µm or more. Some embodiments of the network of collage fibrils of the invention do not contain substantial content of collagen fibers having diameters greater than 5 µm As shown in FIG. 2, the composition of the grain surface of a leather can differ from its more internal portions, such as the corium which contains coarser fiber bundles.

"Fibrillation" refers to a process of producing collagen fibrils. It may be performed by raising the pH or by adjusting the salt concentration of a collagen solution or suspension. In forming the fibrillated collagen, the collagen may be incubated to form the fibrils for any appropriate length of time, including between 1 min and 24 hrs and all intermediate values.

The fibrillated collagen described herein may generally be formed in any appropriate shape and/or thickness, including flat sheets, curved shapes/sheets, cylinders, threads, and complex shapes. These sheets and other forms may have virtually any linear dimensions including a thickness, width or height greater of 10, 20, 30, 40, 50, 60, 70, 80, 90 mm; 1, 2, 3, 4, 5, 6, 7, 8, 9, 10, 50, 100, 200, 500, 1,000, 1,500, 2,000 cm or more.

The fibrillated collagen in a biofabricated leather may lack any or any substantial amount of higher order structure. In a preferred embodiment, the collagen fibrils in a biofabricated leather will be unbundled and not form the large collagen fibers found in animal skin and provide a strong and uniform non-anisotropic structure to the biofabricated leather.

In other embodiments, some collagen fibrils can be bundled or aligned into higher order structures. Collagen fibrils in a biofabricated leather may exhibit an orientation index ranging from 0, >0, 0.1, 0.2, 0.3, 0.4, 0.5, 0.6, 0.7, 0.8, 0.9, <1.0, or 1.0, wherein an orientation index of 0 describes collagen fibrils that lack alignment with other fibrils and an orientation index of 1.0 describes collagen fibrils that are completely aligned. This range includes all intermediate values and subranges. Those of skill in the art are familiar with the orientation index which is also incorporated by reference to Sizeland, et al., J. Agric. Food Chem. 61: 887-892 (2013) or Basil-Jones, et al., J. Agric. Food Chem. 59: 9972-9979 (2011).

The methods disclosed herein make it possible to produce a biofabricated leather comprising collagen fibrils differing in diameter from those produced by an animal expressing the same type of collagen. The characteristics of natural collagens, such as fibril diameter and degree of crosslinking between fibrils are affected by genetic and environmental factors such as the species or breed of the animal and by the condition of the animal, for example the amount of fat, type of feed (e.g. grain, grass), and level of exercise.

A biofabricated leather may be fibrillated and processed to contain collagen fibrils that resemble or mimic the properties of collagen fibrils produced by particular species or breeds of animals or by animals raised under particular conditions.

Alternatively, fibrillation and processing conditions can be selected to provide collagen fibrils distinct from those found in nature, such as by decreasing or increasing the fibril diameter, degree of alignment, or degree of crosslinking compared to fibrils in natural leather.

A crosslinked network of collagen, sometimes called a hydrogel, may be formed as the collagen is fibrillated, or it may form a network after fibrillation; in some variations, the process of fibrillating the collagen also forms gel-like network. Once formed, the fibrillated collagen network may be further stabilized by incorporating molecules with di-, tri-, or multifunctional reactive groups that include chromium, amines, carboxylic acids, sulfates, sulfites, sulfonates, aldehydes, hydrazides, sulfhydryls, diazarines, aryl-, azides, acrylates, epoxides, or phenols.

The fibrillated collagen network may also be polymerized with other agents (e.g. polymers that are capable of polymerizing or other suitable fibers), which could be used to further stabilize the matrix and provide the desired end structure. Hydrogels based upon acrylamides, acrylic acids, and their salts may be prepared using inverse suspension polymerization. Hydrogels described herein may be prepared from polar monomers. The hydrogels used may be natural polymer hydrogels, synthetic polymer hydrogels, or a combination of the two. The hydrogels used may be obtained using graft polymerization, crosslinking polymerization, networks formed of water soluble polymers, radiation crosslinking, and so on. A small amount of crosslinking agent may be added to the hydrogel composition to enhance polymerization.

Average or individual collagen fibril length may range from 100, 200, 300, 400, 500, 600, 700, 800, 900, 1,000 (1 μm); 5, 10, 20, 30, 40, 50, 60, 70, 80, 90, 100, 200, 300, 400, 500, 600, 700, 800, 900, 1,000 μm (1 mm) throughout the entire thickness of a biofabricated leather. These ranges include all intermediate values and subranges.

Fibrils may align with other fibrils over 50, 100, 200, 300, 400, 500 μm or more of their lengths or may exhibit little or no alignment. In other embodiments, some collagen fibrils can be bundled or aligned into higher order structures.

Collagen fibrils in a biofabricated leather may exhibit an orientation index ranging from 0, >0, 0.1, 0.2, 0.3, 0.4, 0.5, 0.6, 0.7, 0.8, 0.9, <1.0, or 1.0, wherein an orientation index of 0 describes collagen fibrils that lack alignment with other fibrils and an orientation index of 1.0 describes collagen fibrils that are completely aligned. This range includes all intermediate values and subranges. Those of skill in the art are familiar with the orientation index which is also incorporated by reference to Sizeland, et al., J. Agric. Food Chem. 61: 887-892 (2013) or Basil-Jones, et al., J. Agric. Food Chem. 59: 9972-9979 (2011).

Collagen fibril density of a biofabricated leather may range from about 1 to 1,000 mg/cc, preferably from 5 to 500 mg/cc including all intermediate values, such as 5, 10, 20, 30, 40, 50, 60, 70, 80, 90, 100, 150, 200, 250, 300, 350, 400, 450, 500, 600, 700, 800, 900 and 1,000 mg/cc.

The collagen fibrils in a biofabricated leather may exhibit a unimodal, bimodal, trimodal, or multimodal distribution, for example, a biofabricated leather may be composed of two different fibril preparations each having a different range of fibril diameters arranged around one of two different modes. Such mixtures may be selected to impart additive, synergistic or a balance of physical properties on a biofabricated leather conferred by fibrils having different diameters.

Natural leather products may contain 150-300 mg/cc collagen based on the weight of the leather product. A biofabricated leather may contain a similar content of collagen or collagen fibrils as conventional leather based on the weight of the biofabricated leather, such as a collagen concentration of 100, 150, 200, 250, 300 or 350 mg/cc.

The fibrillated collagen, sometimes called a hydrogel, may have a thickness selected based on its ultimate use. Thicker or more concentrated preparations of the fibrillated collagen generally produce thicker biofabricated leathers. The final thickness of a biofabricated leather may be only 10, 20, 30, 40, 50, 60, 70, 80 or 90% that of the fibril preparation prior to shrinkage caused by crosslinking, dehydration and lubrication.

"Crosslinking" refers to formation (or reformation) of chemical bonds within between collagen molecules. A crosslinking reaction stabilizes the collagen structure and in some cases forms a network between collagen molecules. Any suitable crosslinking agent known in the art can be used including, without limitation, mineral salts such as those based on chromium, formaldehyde, hexamethylene diisocyanate, glutaraldehyde, polyepoxy compounds, gamma irradiation, and ultraviolet irradiation with riboflavin. The crosslinking can be performed by any known method; see, e.g., Bailey et al., Radiat. Res. 22:606-621 (1964); Housley et al., Biochem. Biophys. Res. Commun. 67:824-830 (1975); Siegel, Proc. Natl. Acad. Sci. U.S.A. 71:4826-4830 (1974); Mechanic et al., Biochem. Biophys. Res. Commun. 45:644-653 (1971); Mechanic et al., Biochem. Biophys. Res. Commun. 41:1597-1604 (1970); and Shoshan et al., Biochim. Biophys. Acta 154:261-263 (1968) each of which is incorporated by reference.

Crosslinkers include isocyantes, carbodiimide, poly(aldehyde), poly(azyridine), mineral salts, poly(epoxies), enzymes, thiirane, phenolics, novolac, resole as well as other compounds that have chemistries that react with amino acid side chains such as lysine, arginine, aspartic acid, glutamic acid, hydroxylproline, or hydroxylysine.

A collagen or collagen-like protein may be chemically modified to promote chemical and/or physical crosslinking between the collagen fibrils. Chemical crosslinking may be possible because reactive groups such as lysine, glutamic acid, and hydroxyl groups on the collagen molecule project from collagen's rod-like fibril structure. Crosslinking that involve these groups prevent the collagen molecules from sliding past each other under stress and thus increases the mechanical strength of the collagen fibers. Examples of chemical crosslinking reactions include but are not limited to reactions with the ε-amino group of lysine, or reaction with carboxyl groups of the collagen molecule. Enzymes such as transglutaminase may also be used to generate crosslinks between glutamic acid and lysine to form a stable γ-glutamyl-lysine crosslink. Inducing crosslinking between functional groups of neighboring collagen molecules is known in the art. Crosslinking is another step that can be implemented here to adjust the physical properties obtained from the fibrillated collagen hydrogel-derived materials.

Still fibrillating or fibrillated collagen may be crosslinked or lubricated. Collagen fibrils can be treated with compounds containing chromium or at least one aldehyde group, or vegetable tannins prior to network formation, during network formation, or network gel formation. Crosslinking further stabilizes the fibrillated collagen leather. For example, collagen fibrils pre-treated with acrylic polymer followed by treatment with a vegetable tannin, such as *Acacia Mollissima*, can exhibit increased hydrothermal stability. In other embodiments, glyceraldehyde may be used as a cross-linking agent to increase the thermal stability, proteolytic resistance, and mechanical characteristics, such as Young's modulus and tensile stress, of the fibrillated collagen.

A biofabricated material containing a network of collagen fibrils may contain 0, >0, 1, 2, 3, 4, 5, 6, 7, 8, 9, 10, 15, 20% or more of a crosslinking agent including tanning agents used for conventional leather. The crosslinking agents may be covalently bound to the collagen fibrils or other components of a biofabricated material or non-covalently associated with them. Preferably, a biofabricated leather will contain no more than 1, 2, 3, 4, 5, 6, 7, 8, 9 or 10% of a crosslinking agent.

"Lubricating" describes a process of applying a lubricant, such as a fat or other hydrophobic compound or any material that modulates or controls fibril-fibril bonding during dehydration to leather or to biofabricated products comprising collagen. A desirable feature of the leather aesthetic is the stiffness or hand of the material. In order to achieve this property, water-mediated hydrogen bonding between fibrils and/or fibers is limited in leather through the use of lubricants. Examples of lubricants include fats, biological, mineral or synthetic oils, cod oil, sulfonated oil, polymers, organofunctional siloxanes, and other hydrophobic compounds or agents used for fatliquoring conventional leather as well as mixtures thereof. While lubricating is in some ways analogous to fatliquoring a natural leather, a biofabricated product can be more uniformly treated with a lubricant due to its method of manufacture, more homogenous composition and less complex composition.

Other lubricants include surfactants, anionic surfactants, cationic surfactants, cationic polymeric surfactants, anionic polymeric surfactants, amphiphilic polymers, fatty acids, modified fatty acids, nonionic hydrophilic polymers, nonionic hydrophobic polymers, poly acrylic acids, poly methacrylic, acrylics, natural rubbers, synthetic rubbers, resins, amphiphilic anionic polymer and copolymers, amphiphilic cationic polymer and copolymers and mixtures thereof as well as emulsions or suspensions of these in water, alcohol, ketones, and other solvents.

Lubricants may be added to a biofabricated material containing collagen fibrils. Lubricants may be incorporated in any amount that facilitates fibril movement or that confers leather-like properties such as flexibility, decrease in brittleness, durability, or water resistance. A lubricant content can range from about 0.1, 0.25, 0.5, 1, 2, 3, 4, 5, 6, 7, 8, 9, 10, 15, 20, 25, 30, 35, 40, 45, 50, 55, and 60% by weight of the biofabricated leather.

"Dehydrating" or "dewatering" describes a process of removing water from a mixture containing collagen fibrils and water, such as an aqueous solution, suspension, gel, or hydrogel containing fibrillated collagen. Water may be removed by filtration, evaporation, freeze-drying, solvent exchange, vacuum-drying, convection-drying, heating, irradiating or microwaving, or by other known methods for removing water. In addition, chemical crosslinking of collagen is known to remove bound water from collagen by consuming hydrophilic amino acid residues such as lysine, arginine, and hydroxylysine among others. The inventors have found that acetone quickly dehydrates collagen fibrils and may also remove water bound to hydrated collagen molecules. Water content of a biofabricated material or leather after dehydration is preferably no more than 60% by weight, for example, no more than 5, 10, 15, 20, 30, 35, 40, 50 or 60% by weight of the biofabricated leather. This range includes all intermediate values. Water content is measured by equilibration at 65% relative humidity at 25° C. and 1 atm.

"Grain texture" describes a leather-like texture which is aesthetically or texturally the similar to the texture of a full grain leather, top grain leather, corrected grain leather (where an artificial grain has been applied), or coarser split grain leather texture. Advantageously, the biofabricated material of the invention can be tuned to provide a fine grain, resembling the surface grain of a leather such as that depicted by FIGS. 2A, 2B and 2C.

A "biofabricated leather product" includes products comprising at least one component of a biofabricated leather such as foot ware, garments, gloves, furniture or vehicle upholstery and other leather goods and products. It includes but is not limited to clothing, such as overcoats, coats, jackets, shirts, trousers, pants, shorts, swimwear, undergarments, uniforms, emblems or letters, costumes, ties, skirts, dresses, blouses, leggings, gloves, mittens, foot ware, shoes, shoe components such as sole, quarter, tongue, cuff, welt, and counter, dress shoes, athletic shoes, running shoes, casual shoes, athletic, running or casual shoe components such as toe cap, toe box, outsole, midsole, upper, laces, eyelets, collar, lining, Achilles notch, heel, and counter, fashion or women's shoes and their shoe components such as upper, outer sole, toe spring, toe box, decoration, vamp, lining, sock, insole, platform, counter, and heel or high heel, boots, sandals, buttons, sandals, hats, masks, headgear, headbands, head wraps, and belts; jewelry such as bracelets, watch bands, and necklaces; gloves, umbrellas, walking sticks, wallets, mobile phone or wearable computer coverings, purses, backpacks, suitcases, handbags, folios, folders, boxes, and other personal objects; athletic, sports, hunting or recreational gear such as harnesses, bridles, reins, bits, leashes, mitts, tennis rackets, golf clubs, polo, hockey, or lacrosse gear, chessboards and game boards, medicine balls, kick balls, baseballs, and other kinds of balls, and toys; book bindings, book covers, picture frames or artwork; furniture and home, office or other interior or exterior furnishings including chairs, sofas, doors, seats, ottomans, room dividers, coasters, mouse pads, desk blotters, or other pads, tables, beds, floor, wall or ceiling coverings, flooring; automobile, boat, aircraft and other vehicular products including seats, headrests, upholstery, paneling, steering wheel, joystick or control coverings and other wraps or coverings.

Many uses of leather products require a durable product that doesn't rip or tear, even when the leather has been stitched together. Typical products that include stitched leather and require durable leather include automobile steering wheel covers, automobile seats, furniture, sporting goods, sport shoes, sneakers, watch straps and the like. There is a need to increase the durability of biofabricated leather to improve performance in these products. A biofabricated leather according to the invention can be used to make any of these products.

Physical Properties of a biofabricated network of collagen fibrils or a biofabricated leather may be selected or tuned by selecting the type of collagen, the amount of concentration of collagen fibrillated, the degree of fibrillation, crosslinking, dehydration and lubrication.

Many advantageous properties are associated with the network structure of the collagen fibrils which can provide strong, flexible and substantially uniform properties to the resulting biofabricated material or leather. Preferable physical properties of the biofabricated leather according to the invention include a tensile strength ranging from 1, 2, 3, 4, 5, 6, 7, 8, 9, 10, 11, 12, 13, 14, 15 or more MPa, a flexibility determined by elongation at break ranging from 1, 5, 10, 15, 20, 25, 30% or more, softness as determined by ISO 17235 of 4, 5, 6, 7, 8 mm or more, a thickness ranging from 0.2, 0.3, 0.4, 0.5, 0.6, 0.7, 0.8, 0.9, 1.0, 1.1, 1.2, 1.3. 1.4, 1.5, 1.6, 1.7, 1.8, 1.9, 2.0 mm or more, and a collagen density (collagen fibril density) of 10, 20, 30, 40, 50, 60, 70, 80, 90, 100, 200, 300, 400, 500, 600, 700, 800, 900, 1,000 mg/cc or more, preferably 100-500 mg/cc. The above ranges include all subranges and intermediate values.

Thickness. Depending on its ultimate application a biofabricated material or leather may have any thickness. Its thickness preferably ranges from about 0.05 mm to 20 mm as well as any intermediate value within this range, such as 0.05, 0.1, 0.2, 0.5, 1, 2, 3, 4, 5, 6, 7, 8, 9, 10, 11, 12, 13, 14, 15, 16, 17, 18, 19, 20, 25, 30, 40, 50 mm or more. The thickness of a biofabricated leather can be controlled by adjusting collagen content.

Elastic modulus. The elastic modulus (also known as Young's modulus) is a number that measures an object or substance's resistance to being deformed elastically (i.e., non-permanently) when a force is applied to it. The elastic modulus of an object is defined as the slope of its stress-strain curve in the elastic deformation region. A stiffer material will have a higher elastic modulus. The elastic modulus can be measured using a texture analyzer.

A biofabricated leather can have an elastic modulus of at least 100 kPa. It can range from 100 kPa to 1,000 MPa as well as any intermediate value in this range, such as 0.1, 0.2, 0.3, 0.4, 0.5, 0.6, 0.7, 0.8, 0.9, 1, 2, 3, 4, 5, 6, 7, 8, 9, 10, 50, 100, 200, 300, 400, 500, 600, 700, 800, 900, or 1,000 MPa. A biofabricated leather may be able to elongate up to 300%) from its relaxed state length, for example, by >0, 1, 2, 3, 4, 5, 6, 7, 8, 9, 10, 20, 30, 40, 50, 60, 70, 80, 90, 100, 150, 200, 250, or 300% of its relaxed state length.

Tensile strength (also known as ultimate tensile strength) is the capacity of a material or structure to withstand loads tending to elongate, as opposed to compressive strength, which withstands loads tending to reduce size. Tensile strength resists tension or being pulled apart, whereas compressive strength resists compression or being pushed together.

A sample of a biofabricated material may be tested for tensile strength using an Instron machine. Clamps are attached to the ends of the sample and the sample is pulled in opposite directions until failure. Good strength is demonstrated when the sample has a tensile strength of at least 1 MPa. A biofabricated leather can have a tensile strength of at least 1 kPa. It can range from 1 kPa to 100 MPa as well as any intermediate value in this range, such as 1, 2, 3, 4, 5, 6, 7, 8, 9, 10, 50, 100, 200, 300, 400, 500 kPA; 0.5, 0.6, 0.7, 0.8, 0.9, 1.0, 1.1, 1.2, 1.3, 1.4, 1.5, 2, 3, 4, 5, 6, 7, 8, 9, 10, 20, 30, 40, 50, 60, 70, 80, 90, or 100 MPa.

Tear strength (also known as tear resistance) is a measure of how well a material can withstand the effects of tearing. More specifically however it is how well a material (normally rubber) resists the growth of any cuts when under tension, it is usually measured in kN/m. Tear resistance can be measured by the ASTM D 412 method (the same used to measure tensile strength, modulus and elongation). ASTM D 624 can be used to measure the resistance to the formation of a tear (tear initiation) and the resistance to the expansion of a tear (tear propagation). Regardless of which of these two is being measured, the sample is held between two holders and a uniform pulling force applied until the aforementioned deformation occurs. Tear resistance is then calculated by dividing the force applied by the thickness of the material. A biofabricated leather may exhibit tear resistance of at least 1, 2, 3, 4, 5, 6, 7, 8, 9, 10, 15, 20, 25, 30, 35, 40, 45, 50, 100, 150 or 200% more than that of a conventional top grain or other leather of the same thickness comprising the same type of collagen, e.g., bovine Type I or Type III collagen, processed using the same crosslinker(s) or lubricants. A biofabricated material may have a tear strength ranging from about 1 to 500 N, for example, 1, 2, 3, 4, 5, 6, 7, 8, 9, 10, 20, 30, 40, 50, 60, 70, 80, 90, 100, 125, 150, 175, 200, 225, 250, 275, 300, 325, 350, 375, 400, 425, 450, 475, or 500 as well as any intermediate tear strength within this range.

Softness. ISO 17235:2015 specifies a non-destructive method for determining the softness of leather. It is applicable to all non-rigid leathers, e.g. shoe upper leather, upholstery leather, leather goods leather, and apparel leather. A biofabricated leather may have a softness as determined by ISO 17235 of 2, 3, 4, 5, 6, 7, 8, 10, 11, 12 mm or more.

Figure 2A:
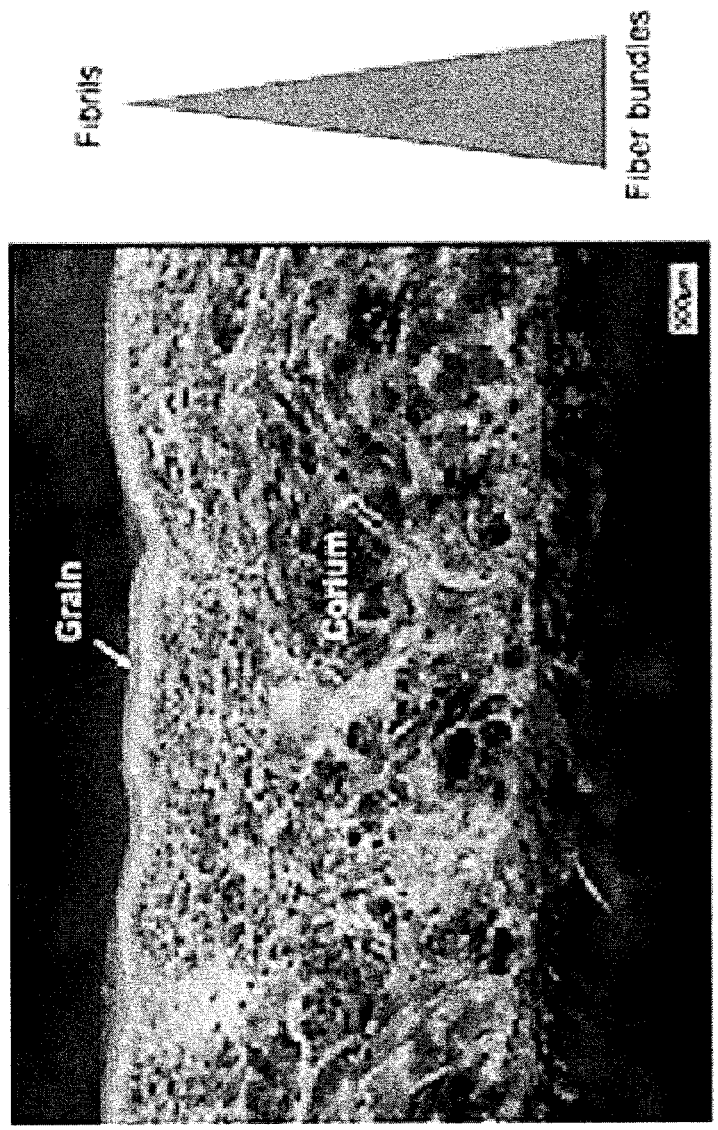
FIG. 2A is a picture showing the composition of buffalo hide. The top grain layer and the corium layer underneath are shown and the relative degrees of higher order organization from collagen fibrils to collagen fiber bundles are indicated. The top grain layer is mostly composed of fine collagen fibrils while the corium layer is mostly composed of coarser collagen fibers and fiber bundles.

Grain. The top grain surface of leather is often regarded as the most desirable due to its soft texture and smooth surface. The top grain is a highly porous network of collagen fibrils. The strength and tear resistance of the grain is often a limitation for practical applications of the top grain alone and conventional leather products are often backed with corium having a much coarser grain. FIGS. 2A, 2B and 2C compare top grain and corium leather surfaces. A biofabricated material as disclosed herein which can be produced with strong and uniform physical properties or increased thickness can be used to provide top grain like products without the requirement for corium backing.

Content of other components. In some embodiments, the collagen is free of other leather components such as elastin or non-structural animal proteins. However, in some embodiments the content of actin, keratin, elastin, fibrin, albumin, globulin, mucin, mucinoids, noncollagen structural proteins, and/or noncollagen nonstructural proteins in a biofabricated leather may range from 0, 1, 2, 3, 4, 5, 6, 7, 8, 9 to 10% by weight of the biofabricated leather. In other embodiments, a content of actin, keratin, elastin, fibrin, albumin, globulin, mucin, mucinoids, noncollagen structural proteins, and/or noncollagen nonstructural proteins may be incorporated into a biofabricated leather in amounts ranging from >0, 1, 2, 3, 4, 5, 6, 7, 8, 9, 10, 11, 12, 13, 14, 15, 16, 17, 18, 19, 20% or more by weight of a biofabricated leather. Such components may be introduced during or after fibrillation, cross-linking, dehydration or lubrication.

A "leather dye" refers to dyes which can be used to color leather or biofabricated leather. These include acidic dyes, direct dyes, lakes, sulfur dyes, basic dyes and reactive dyes. Dyes and pigments can also be incorporated into a precursor of a biofabricated leather, such as into a suspension or network gel comprising collagen fibrils during production of the biofabricated leather.

"Fillers". In some embodiments a biofabricated leather may comprise fillers, other than components of leather, such as microspheres. One way to control the organization of the dehydrated fibril network is to include filling materials that keep the fibrils spaced apart during dehydration. These filler materials include nanoparticles, microparticles, or various polymers such as syntans commonly used in the tanning industry. These filling materials could be part of the final dehydrated leather material, or the filling materials could be sacrificial, that is they are degraded or dissolved away leaving open space for a more porous fibril network. The shape and dimension of these fillers may also be used to control the orientation of the dehydrated fibril network.

In some embodiments a filler may comprise polymeric microsphere(s), bead(s), fiber(s), wire(s), or organic salt(s). Other materials may also be embedded or otherwise incorporated into a biofabricated leather or into a network of collagen fibrils according to the invention. These include, but are not limited to one fibers, including both woven and nonwoven fibers as well as cotton, wool, cashmere, angora, linen, bamboo, bast, hemp, soya, seacell, fibers produced from milk or milk proteins, silk, spider silk, other peptides or polypeptides including recombinantly produced peptides or polypeptides, chitosan, mycelium, cellulose including bacterial cellulose, wood including wood fibers, rayon, lyocell, vicose, antimicrobial yarn (A.M.Y.), Sorbtek, nylon, polyester, elastomers such as lycra®, spandex or elastane and other polyester-polyurethane copolymers, aramids, carbon including carbon fibers and fullerenes, glass including glass fibers and nonwovens, silicon and silicon-containing compounds, minerals, including mineral particles and mineral fibers, and metals or metal alloys, including those comprising iron, steel, lead, gold, silver, platinum, copper, zinc and titanium, which may be in the form of particles, fibers, wires or other forms suitable for incorporating into biofabricated leather. Such fillers may include an electrically conductive material, magnetic material, fluorescent material, bioluminescent material, phosphorescent material or other photoluminescent material, or combinations thereof. Mixtures or blends of these components may also be embedded or incorporated into a biofabricated leather, for example, to modify the chemical and physical properties disclosed herein.

Method of making. A method of forming biofabricated leather from collagen includes the steps of fibrillating, crosslinking, dehydrating/dewatering and lubricating in any order. For example, a collagen solution may be fibrillated, the fibrils may be crosslinked with an agent such as glutaraldehyde, then coated with a lubricant such as a sulfited oil, and then dehydrated through filtration to form a fibrillated collagen leather. However, the method of making is not limited to this particular order of steps.

Alternatively, following fibril crosslinking, the fibrils can be dehydrated through a solvent exchange with acetone, followed by fat liquoring with a sulfited oil before evaporating away the solvent to form a fibrillated collagen leather. In addition, the incorporation of chemical or physical crosslinks between fibrils (to impart material strength) can be accomplished at any point during the process. For example, a solid fibrillated collagen, sometimes called a hydrogel, can be formed, then this fibril network can be dehydrated through a solvent exchange with acetone, followed by fat liquoring with a sulfited oil. Further, the collagen fibrils can be crosslinked into a network through the incorporation of other polymers such as those typically used in resin formulations.

Materials such as lubricants, humectants, dyes and other treating agents can be uniformly distributed through a biofabricated leather product during the biofabrication process This is an advantage compared to conventional leather tanning and fat liquoring which due to its structural heterogeneity often makes uniform treatment impossible. Further, as chemical agents can be incorporated before network formation, smaller amounts of treatment chemicals would be necessary as there is reduced chemical loss by not having to penetrate a collagen network from a float containing the treatment chemicals. Unlike high temperatures often used to treat natural leather, a biofabricated can be heated at ambient temperature or at a temperature no greater than 37° C. during processing before evaporating away the solvent to form a fibrillated collagen leather. Alternatively, collagen fibrils can be crosslinked and lubricated in suspension before forming a network between fibrils during dehydration or through the addition of a binding agent to the suspension or to the dehydrated material.

A method of forming a biofabricated leather material may include inducing fibrillation of collagen in a solution; crosslinking (e.g., tanning) and dehydrating the fibrillated collagen, which may appear in the form of a hydrogel, to obtain a fibrillated collagen sheet or other product, and incorporating at least one humectant or lubricant, such as a fat or oil into the fibrillated collagen sheet or product to obtain a flexible biofabricated leather.

A method of biofabricating a leather from fibrils may include inducing fibrillation of collagen or collagen-like proteins in a solution to obtain a fibrillated collagen hydrogel; crosslinking the fibrillated collagen hydrogel to obtain a fibrillated collagen hydrogel leather; and incorporating at least one lubricating oil into the fibrillated collagen hydrogel leather.

In the processes described herein for producing a biofabricated leather, the order of the steps for forming biofabricated leather may be varied or two or more steps may be performed simultaneously. For example, fibrillating and crosslinking may be performed together or by addition of one or more agents, or crosslinker and lubricant may be incorporated in the solution prior to fibrillating the collagen, etc.

The collagen or collagen-like proteins may be obtained through extraction of collagen from an animal source, such as, but not limited to bovine hide or tendon collagen extraction. Alternatively, the collagen or collagen-like proteins may be obtained from a non-animal source, for example through recombinant DNA techniques, cell culture techniques, or chemical peptide synthesis.

Any of these methods may include polymerizing the collagen or collagen-like proteins into dimers, trimers, and higher order oligomers prior to fibrillation, and/or chemically modifying the collagen or collagen-like proteins to promote crosslinking between the collagen or collagen-like proteins.

Any of these methods may include functionalizing the collagen or collagen-like proteins with one or a combination of chromium, amine, carboxylic acid, sulfate, sulfite, sulfonate, aldehyde, hydrazide, sulfhydryl, diazirine, aryl, azide, acrylate, epoxide, or phenol group.

Inducing fibrillation may include adding a salt or a combination of salts, for example, the salt or combination of salts may include: $Na_3PO_4$, $K_3PO_4$, KCl, and NaCl, the salt concentration of each salt may be between 10 mM to 5M, etc.

In general, inducing fibrillation may comprise adjusting the pH with an acid or a base, adding a nucleating agent, such as a branched collagen microgel, wherein the nucleating agent has a concentration between 1 mM to 100 mM.

The fibrillated collagen may be stabilized with a chromium compound, an aldehyde compound, or vegetable tannins, or any other crosslinking agent. For example, the fibrillated collagen may be stabilized with a chromium compound, an aldehyde compound, or vegetable tannins, wherein the chromium, aldehyde, or vegetable tannin compounds having a concentration of between 1 mM to 100 mM.

Any of these methods may include adjusting the water content of the fibrillated collagen to 5, 10, 20, 25, 30, 40, 50 or 60% or less by weight to obtain the fibrillated collagen hydrogel leather. For example, the fibrillated collagen material may be dehydrated. Any of these methods may also include dyeing and/or applying a surface finish to the fibrillated collagen leather.

The selection of collagen starting materials for biofabricating the engineered leather materials described herein can be controlled, the resulting product may differential formed with physical and aesthetic properties for distinct end uses, such as with features useful in footwear and different features useful in apparel. In general, the biofabricated fibrillated collagen hydrogel-derived leathers described herein are formed from solutions of collagen that are induced to self-assemble into collagen fibrils.

The collagen fibrils, unlike endogenous collagen fibrils, are not assembled into any high-order structures (e.g., bundles of fibers), but remain somewhat disordered, more particularly unbundled fibrils. When assembled in vivo, collagen fibrils are typically aligned laterally to form bundles having a higher order of structure and make up tough, micron-sized collagen fibers found, e.g., in skin. A characteristic feature of native collagen fibrils is their banded structure. The diameter of the native fibril changes slightly along the length, with a highly reproducible D-band repeat of approximately 67 nm. In some of the methods described herein, collagen fibrils may be unbanded and unbundled or may be banded and unbundled or may have a D-band of different spacing ranging from 1 to 100 nm and all intermediate values in this range). The collagen fibrils may be randomly oriented (e.g., un-oriented or not oriented in any particular direction or axis).

The starting material used to form the biofabricated leather material as described herein may include any appropriate non-human collagen source or modified or engineered collagens that can be fibrillated.

Various forms of collagen are found throughout the animal kingdom. The collagen used herein may be obtained from animal sources, including both vertebrates and invertebrates, or from synthetic sources. Collagen may also be sourced from byproducts of existing animal processing. Collagen obtained from animal sources may be isolated using standard laboratory techniques known in the art, for example, Silva et. Al., Marine Origin Collagens and its Potential Applications, Mar. Drugs, 2014 December, 12(12); 5881-5901).

One major benefit of the biofabricated leather materials and methods for forming them described herein is that collagen may be obtained from sources that do not require killing of an animal.

The collagen described herein also may be obtained by cell culture techniques including from cells grown in a bioreactor.

Collagen may also be obtained via recombinant DNA techniques. Constructs encoding non-human collagen may be introduced into host organisms to produce non-human collagen. For instance, collagen may also be produced with yeast, such as *Hansenula polymorpha, Saccharomyces cerevisiae, Pichia pastoris* and the like as the host. Further, in recent years, bacterial genomes have been identified that provide the signature (Gly-Xaa-Yaa)n repeating amino acid sequence that is characteristic of triple helix collagen. For example, gram positive bacterium *Streptococcus pyogenes* contains two collagen-like proteins, Scl1 and Scl2 that now have well characterized structure and functional properties. Thus, it would be possible to obtain constructs in recombinant *E. coli* systems with various sequence modifications of either Scl1 or Scl2 for establishing large scale production methods. Collagen may also be obtained through standard peptide synthesis techniques. Collagen obtained from any of the techniques mentioned may be further polymerized. Collagen dimers and trimers are formed from self-association of collagen monomers in solution.

As an initial step in the formation of the collagen materials described herein, the starting collagen material may be placed in solution and fibrillated. Collagen fibrillation may be induced through the introduction of salts to the collagen solution. The addition of a salt or a combination of salts such as sodium phosphate, potassium phosphate, potassium chloride, and sodium chloride to the collagen solution may change the ionic strength of the collagen solution. Collagen fibrillation may occur as a result of increasing electrostatic interactions, through greater hydrogen bonding, Van der Waals interactions, and covalent bonding. Suitable salt concentrations may range, for example, from approximately 10 mM, 50 mM, 100 mM, 500 mM, 1M, 2M, 3M, 4M to 5M as well as any intermediate value within this range.

Collagen fibrillation may also be induced or enhanced with a nucleating agent other than salts. Nucleating agents provide a surface on which collagen monomers can come into close contact with each other to initiate fibrillation or can act as a branch point in which multiple fibrils are connected through the nucleating agent. Examples of suitable nucleating agents include but are not limited to: microgels containing collagen, collagen micro or nanoparticles, metallic particles or naturally or synthetically derived fibers. Suitable nucleating agent concentrations may range from approximately 1 mM to 100 mM.

A collagen network may also be highly sensitive to pH. During the fibrillation step, the pH may be adjusted to control fibril dimensions such as diameter and length. The overall dimensions and organization of the collagen fibrils will affect the toughness, stretch-ability, and breathability of the resulting fibrillated collagen derived materials. This may be of use for fabricating fibrillated collagen derived leather for various uses that may require different toughness, flexibility, and breathability. Adjustment of pH, with or without a change in salt concentration may be used for fibrillation.

One way to control the organization of the dehydrated fibril network is to include filling materials that keep the fibrils spaced apart during drying. These filler materials could include nanoparticles, microparticles, or various polymers such as syntans commonly used in the tanning industry. These filling materials could be part of the final dehydrated leather material, or the filling materials could be sacrificial, that is they are degraded or dissolved away leaving open space for a more porous fibril network.

The collagen or collagen-like proteins may be chemically modified to promote chemical and physical crosslinking between the collagen fibrils. Chemical crosslinking may be possible because reactive groups such as lysine, glutamic acid, and hydroxyl groups on the collagen molecule project from collagen's rod-like fibril structure. Crosslinking that involve these groups prevent the collagen molecules from sliding past each other under stress and thus increases the mechanical strength of the collagen fibers. Examples of chemical crosslinking reactions include but are not limited to reactions with the ε-amino group of lysine, or reaction with carboxyl groups of the collagen molecule. Enzymes such as transglutaminase may also be used to generate crosslinks between glutamic acid and lysine to form a stable γ-glutamyl-lysine crosslink. Inducing crosslinking between functional groups of neighboring collagen molecules is known in the art. Crosslinking is another step that can be implemented here to adjust the physical properties obtained from the fibrillated collagen hydrogel-derived materials.

Once formed, the fibrillated collagen network may be further stabilized by incorporating molecules with di-, tri-, or multifunctional reactive groups that include chromium, amines, carboxylic acids, sulfates, sulfites, sulfonates, aldehydes, hydrazides, sulfhydryls, diazarines, aryl-, azides, acrylates, epoxides, or phenols.

The fibrillated collagen network may also be polymerized with other agents (e.g. polymers that are capable of polymerizing or other suitable fibers) that form a hydrogel or have fibrous qualities, which could be used to further stabilize the matrix and provide the desired end structure. Hydrogels based upon acrylamides, acrylic acids, and their salts may be prepared using inverse suspension polymerization. Hydrogels described herein may be prepared from polar monomers. The hydrogels used may be natural polymer hydrogels, synthetic polymer hydrogels, or a combination of the two. The hydrogels used may be obtained using graft polymerization, crosslinking polymerization, networks formed of water soluble polymers, radiation crosslinking, and so on. A small amount of crosslinking agent may be added to the hydrogel composition to enhance polymerization.

Any appropriate thickness of the fibrillated collagen hydrogel may be made as described herein. Because the final thickness will be much less (e.g., between 10-90% thinner) than the hydrogel thickness, the initial hydrogel thickness may depend on the thickness of the final product desired, presuming the changes to the thickness (or overall volume) including shrinkage during crosslinking, dehydration and/or adding one or more oils or other lubricants as described herein.

A hydrogel thickness may be between 0.1 mm and 50 cm or any intermediate value within this range. In forming the fibrillated hydrogel, the hydrogel may be incubated to form the thickness for any appropriate length of time, including between 1 min and 24 hrs.

The fibrillated collagen hydrogels described herein may generally be formed in any appropriate shape and/or thickness, including flat sheets, curved shapes/sheets, cylinders, threads, and complex shapes. Further, virtually any linear size of these shapes. For example, any of these hydrogels may be formed into a sheet having a thickness as described and a length of greater than 10 mm (e.g., greater than, in cm, 15, 20, 25, 30, 35, 40, 45, 50, 55, 60, 65, 70, 75, 80, 85, 90, 95, 100, 200, 300, 400, 500, 600, 700, 800, 900, 1000, 1100, 1200, 1500, etc.) and width that is greater than 10 mm, such as greater than, in cm, 15, 20, 25, 30, 35, 40, 45, 50, 55, 60, 65, 70, 75, 80, 85, 90, 95, 100, 200, 300, 400, 500, 600, 700, 800, 900, 1000, 1100, 1200, 1500, etc.

Once the collagen fibrils, often characterized as a hydrogel, have formed or during formation, they may be crosslinked. For example, the fibrillated collagen hydrogel be treated with compounds containing chromium or at least one aldehyde group, or vegetable tannins prior to gel formation, during gel formation, or after gel formation, to further stabilize the fibrillated collagen hydrogel. For example, collagen fibrils may be pre-treated with acrylic polymer followed by treatment with a vegetable tannin (e.g., *Acacia Mollissima*) may exhibit increased hydrothermal stability. In other examples, glyceraldehyde may be used as a crosslinking agent that may increase the thermal stability, proteolytic resistance, and mechanical characteristics (e.g. Young's modulus, tensile stress) of the fibrillated collagen hydrogel.

Fibrillation of a solution of collagen as described herein (e.g., formation of collagen fibrils that are lacking in higher order organization such as bundles) may be visually tracked. For example, as fibrillation is induced, the clear solution of collagen, which has little absorbance at 400 nm, becomes opaque and having an absorbance of approximately 0.5 at 400 nm. Depending on the temperature and volume of starting material, the fibrillation and hydrogel formation may occur somewhat quickly after induction and be largely complete after an hour and a half, as shown by the absorbance values leveling off after 70 minute's time passing. An increase in storage modulus (or viscoelastic qualities of the material) of the fibrillated collagen hydrogel after induction from around 1 Pa (for the solution of collagen) to approximately 400 Pa for the fibrillated collagen hydrogel may occur.

As mentioned above and illustrated in FIGS. 1 and 2, animal skin typically includes fibrils that are ordered into higher-order structures, including the presence of banding (having regular lacunar regions) and formation of multiple fibrils into aligned fibers which may then bundled into collagen bundles. In contrast, the collagen hydrogels and therefore the biofabricated leathers described herein may have a primary disorganized collagen fibril structure throughout the entire thickness (in some cases entire volume) of the material. Specifically, the collagen structure of the biofabricated leathers formed from collagen hydrogels may be primarily unbundled and un-oriented along any particular axis. In some variations the collagen fibrils may be unbanded (e.g., greater than 10% unbanded, greater than 20%, 30%, 40%, 50%, 60%, 70%, 80%, 90%, etc. unbanded throughout the volume). Furthermore, the orientation of the collagen fibrils within the volume (or throughout the volume) may be un-oriented, or randomly oriented, and this lack of orientation may be the same throughout the volume, rather than changing through the volume thickness as in native leather, which may have change from bundles of collagen fibrils that are vertically oriented to bundles that are horizontally oriented in the thickness. Any of the properties which are the same at any level thickness of the hydrogel and therefore resulting leather material may be referred to herein as "uniformly" the same throughout the thickness.

In addition, any of the biofabricated leathers described herein may have a uniform distribution of fibrils throughout the thickness of the gel and therefore resulting leather material. This is in contrast with native leathers, such as the material shown in FIG. 2, showing an increase in the number of fiber bundles through the thickness of the material.

The lack of higher-level organization of the fibrillated collagen hydrogels and leather material formed from them is apparent in FIGS. 3A and 3B. FIG. 3A shows a scanning electron micrograph of a fibrillated collagen hydrogel formed as described herein. Similarly, FIG. 4 shows a transmission electron micrograph through a fibrillated collagen hydrogel. The transmission electron micrograph and the scanning electron micrograph both show the fibrillated collagen hydrogel as being a disordered tangle of collagen fibrils. As previously mentioned, the density and to some extent, the pattern of collagen fibril formation may be controlled by adjusting the pH of the collagen solution during fibrillation induction along with the concentration of fibrils during dehydration. FIG. 3 also shows a scanning electron micrograph of bovine corium. In comparison with a natural bovine corium (FIG. 3B), the fibrillated collagen network is much more random and lacks the apparent striations. Although the overall size of the fibrils may be similar, the arrangement of these fibrils is quite different. Such ultrastructural differences between the collagen fibrils within the fibrillated collagen hydrogel and natural tissue such as bovine corium (and resulting leather made therefrom) may not be an issue in the final biofabricated leather product may be as soft or softer, and more pliable than natural leather, and may have a similar appearance.

The fibrillated collagen, sometimes called a hydrogel, may then be dehydrated to rid the fibrillated collagen hydrogel of the majority of its water content. Removing the water from the fibrillated collagen hydrogel may change its physical quality from a hydrated gel to a pliable sheet. The material may be treated to prevent breakage/tearing. For example, care may be taken not to remove too much water from the fibrillated collagen. In some examples, it may be desirable to dehydrate the fibrillated collagen to have a water content of less than 5, 10, 15, 20, 25, 30, 40, 50 or 60%. Water content is determined by equilibration at 25° C. at 1 atm pressure at a relative humidity of 65%.

Dehydration may involve air drying, vacuum and pressure filtration, solvent exchange or the like. For example, fibrillated collagen hydrogel may also undergo dehydration through replacement of its water content with organic solvents. Suitable organic solvents may include, but are not limited to acetone, ethanol, diethyl ether, and so forth. Subsequently, the organic solvents may be evaporated (e.g. air drying, vacuum drying, etc.). It is also possible to perform successive steps of dehydration using one or more than one organic solvent to fine tune the level of dehydration in the final product.

After or during dehydration, the fibrillated collagen material may be treated with lubricants and/or oils to impart greater flexibility and suppleness to the fibrillated collagen material. Using a combination of oil and solvent may allow the oil to better penetrate the fibrillated collagen network compared to using oil by itself. Oil by itself will only likely penetrate the exposed surfaces but may not readily infiltrate the entire thickness of the fibrillated collagen material in a reasonable amount of time. Once the oil/solvent composition has penetrated the entire thickness of the material, the solvent may then be removed. In some embodiments, the resulting fibrillated collagen material exhibits a more leather-like appearance as compared to the dehydrated fibrillated collagen material prior to lubricant and/or oil treatment. Suitable oils and lubricants may include but are not limited to castor oil, pine oil, lanolin, mink oil, neatsfoot oil, fish oil, shea butter, aloe, and so forth.

Lubricating the dehydrated and crosslinked fibrillated collagen network or hydrogel to form a leather material may result in a material having properties that are similar, or better, than the properties of natural leather. The solutions that included a combination of oils and organic solvent increased the mass and the softness (inversely proportional to the slope of the stress-strain curve) of the dehydrated fibrillated collagen material. This is due to the combination of oils and organic solvents penetrating the dehydrated fibrillated collagen material and once penetrated through, the oils remained distributed throughout the material, while the organic solvents are able to evaporate away. While not shown, the use of oils alone may not be as effective in penetrating entirely through the dehydrated fibrillated collagen material.

The resulting fibrillated collagen materials then may be treated similarly to natural leather derived from animal hide or skin, and be re-tanned, dyed, and/or finished. Additional processing steps may include: crosslinking, re-tanning, and surface coating. Crosslinking and re-tanning may include sub-processes such as wetting back (re-hydrating semi-processed leather), sammying (45-55% water is squeezed from the leather), splitting (leather is split into one or more layers), shaving (leather is thinned), neutralization (pH of leather is adjusted to between 4.5 and 6.5), dyeing (leather is colored), fat liquoring (fats, oils, waxes are fixed to the leather fibers), filling (dense/heavy chemicals to make leather harder and heavier), stuffing (fats, oils, waxes added between leather fibers), fixation (unbound chemicals are bonded/trapped and removed), setting (grain flatness are imparted and excess water removed), drying (leather is dried to desired moisture levels, 10-25%), conditioning (moisture is added to leather to a 18-28% level), softening (physical softening of leather by separating the fibers), or buffing (abrading surface of leather to reduce nap and grain defects). Surface coating may include any one or combination of the following steps: oiling (leather coated with raw oil or oils), buffing, spraying, roller coating, curtain coating, polishing, plating, embossing, ironing, or glazing.

Unlike animal hides, where the hide has to be trimmed to obtain the desired thickness or dimensions, the engineered leather material may be fabricated with a wide range of thicknesses as well as the desired dimensions with a particular end product in mind.

The production of such engineered leather materials may also generate less waste by bypassing the step of removing excess proteins, fats, and hair necessary for treating natural animal hide in the leather production process, which results in less environmental impact from the disclosed process and the products derived from these methods.

Embodiments of the Invention

The invention includes, but is not limited to biofabricated materials having the features described below.

In a first embodiment, the invention is directed to a material comprising a network of collagen fibers, such as a biofabricated material or biofabricated leather:

(i) comprising a network of non-human collagen fibrils, wherein less than 5, 10, 15, 20, 25, 30, 35, or 40% by weight of the collagen fibrils in the material are in the form of collagen fibers having a diameter of 1, 2, 3, 4, 5, 6, 7, 8, 9, or 10 μm or more and/or are in the form of fibrils aligned for 100 μm or more of their lengths; wherein said material contains no more than 10, 20, 30, 40, 50, or 60% by weight water; wherein said material contains at least 1, 2, 3, 4, 5, 6, 7, 8, 9, 10, 20, 30, or 40% by weight of a lubricant; and wherein optionally, the material comprises a top and bottom surface or an inner and outer surface; or (ii) comprising a network of recombinant non-human collagen fibrils, wherein the collagen contains substantially no 3-hydroxyproline, and, optionally, substantially no hydroxylysine; wherein said material contains no more than 5, 10, 15, 20, 25, 30, 35, 40, 45, 50, 55, or 60% by weight water; wherein the material contains at least 1, 2, 3, 4, 5, 6, 7, 8, 9, 10, 20, 30, or 40% of a lubricant; and wherein optionally, the material comprises a top and bottom surface or an inner and outer surface. Water content in this material is preferably no more than 25 to 40%. Lubricant content may be selected to match or not exceed the absorptive capacity of the biofabricated material for a lubricant. Such a material may comprise mammalian collagen, such as bovine Type I or Type III collagen. Preferably it will not contain hair, hair follicle(s), or fat(s) of an animal that naturally expresses the collagen molecules it contains. For example, it may contain less than 1, 2, 3, 4, 5, 6, 7, 8, 9, or 10% by weight of actin, keratin, elastin, fibrin, albumin, globulin, mucin, mucinoids, noncollagen structural proteins, and/or noncollagen nonstructural proteins found in conventional leather. It may be substantially free of other collagenous proteins, carbohydrates, nucleic acids, or lipids, or immunogens, antigens, or allergens found in a conventional leather, such as an animal that naturally expresses the collagen molecules in a biofabricated material. Alternative embodiments may incorporate 1, 2, 3, 4, 5, 6, 7, 8, 9, or 10% of one or more of actin, keratin, elastin, fibrin, albumin, globulin, mucin, mucinoids, noncollagen structural proteins, and/or noncollagen nonstructural proteins found in conventional leather.

The collagen used to produce the fibrils in this material may be isolated from a natural source, preferably in a purified form, or it may be recombinantly produced or produced by chemical synthesis. Collagen generally contains 4-hydroxyproline. It may different in chemical structure from collagen obtained from a natural source, for example, it may contain a lower content of, or substantially no hydroxylysine or 3-hydroxyproline, glycosylated or crosslinked amino acid residues, or other post-translational modifications of a collagen amino acid sequence. Alternatively, it may contain a higher content of hydroxylated amino acid residues, glycosylated residues, crosslinks or other chemical modifications.

The material described above generally comprises a network of collagen fibrils which may exhibit a fibril density of between 5, 10, 20, 50, 100, 200, 300, 400, 500, 600, 700, 800, 900, and 1,000 mg/cc, preferably between 100 and 500 mg/cc. These fibrils or network of fibrils can confer a grain texture, such as a top grain texture, feel, or aesthetic on a biofabricated material or biofabricated leather. However, a biofabricated material can exhibit a porosity and other physical properties that are more uniform than a corresponding conventional leather which can be controlled or tuned by control of composition, fibril size, crosslinking and lubricating in a biofabricated product.

In many embodiments, the biofabricated material described above will have a top and bottom surface, or an inner and outer surface, comprising the collagen fibrils. One or more of these surfaces may be externally exposed. A single layer of biofabricated material can exhibit substantially identical grain and appearance on both of its sides, unlike conventional leather products where collagen fibril or fiber diameters increase for more inner layers of a hide.

In other embodiments a biofabricated material may be cast, molded or otherwise configured into a particular shape which can exhibit substantially uniform properties over its surface(s).

The collagen fibrils in a biofabricated material can be tuned to have a particular diameter. The distribution of fibril diameters may exhibit a substantially unimodal distribution, a bimodal distribution, a trimodal distribution or other multimodal distributions. Multimodal distributions may be composed of two or more different preparations of fibrils produced using different fibrillation conditions. In a substantially unimodal distribution >50, 60, 70, 80, 90, 95 or 99% of diameters of the fibrils distribute around a single mode. In bimodal distributions at least 5, 10, 15, 20, 25, 30, 35, 40, 45, or 50% of the fibrils will distribute around one mode. In trimodal and other multimodal distributions, generally, at least about 5, 10, 15, 20, 25, 30% or more (depending on the number of modes) of the fibril diameters will distribute around a mode.

A biofabricated material may contain fibrils where at least 50, 60, 70, 80, 90, 95, or 99% of the collagen fibrils have diameters between 1 nm and 1 μm. Fibril diameters may be determined by methods known in the art including by visual inspection of micrographs or electron micrographs, such as scanning or transmission electron micrographs. For example, the collagen fibrils may have a collective average or individual fibril diameter ranging from 1, 2, 3, 4, 5, 10, 15, 20, 30, 40, 50, 60, 70, 80, 90, 100, 200, 300, 400, 500, 600, 700, 800, 900, or 1,000 nm (1 μm).

The collagen fibrils in the biofabricated material described above are usually crosslinked by contact with at least one agent that forms crosslinks between collagen fibrils. Such a crosslinker may be selected from one or more of an amine, carboxylic acid, sulfate, sulfite, sulfonate, aldehyde, hydrazide, sulfhydryl, diazirine, aryl, azide, acrylate, epoxide, phenol, chromium compound, vegetable tannin, and syntan.

Crosslinking may be performed at a crosslinker concentration ranging from 1, 5, 10, 25, 50, 75 to 100 mM and may be conducted under conditions that uniformly expose collagen fibrils to the crosslinker so that the average number of crosslinks formed is uniform and varies by no more than 5, 10, 15, 20, 25, 30, 40, 45, or 50% in identical unit volumes of the material.

A biofabricated material may contain at least 1, 2, 3, 4, 5, 6, 7, 8, 9, or 10% of a crosslinking agent based on the weight of the material or based on the weight of the collagen or collagen fibrils in the material. The crosslinker may be present in a covalently or non-covalently form, for example, it may be covalently bound to the collagen fibrils. A crosslinker may be uniformly present in the biofabricated material where its concentration by weight (or by mole) varies by no more than 5, 10, 15, 20, 25, 30, 40, 45, or 50% in identical unit volumes of the material.

The biofabricated material or biofabricated leather described above contains a lubricant. Not lubricated materials containing a network of collagen fibrils can be produced, such a precursor substrates for later lubrication, but can lack the flexible and other useful properties of a lubricated product. Lubricants may be incorporated in any amount that facilitates fibril movement or that confers leather-like properties such as flexibility, decrease in brittleness, durability, strength, increase resistance to fracture or tearing, or water resistance. A lubricant content can range from about 0.1, 0.25, 0.5, 1, 2, 3, 4, 5, 6, 7, 8, 9, 10, 15, 20, 25, 30, 35, 40, 45, 50, 55, and 60% by weight of the biofabricated leather.

Lubricants used in embodiments of the invention include, but are not limited to fats, biological, mineral or synthetic oils, cod oil, sulfonated oil, polymers, resins, organofunctional siloxanes, and other agents used for fatliquoring conventional leather; mixtures thereof. Other lubricants include surfactants, anionic surfactants, cationic surfactants, cationic polymeric surfactants, anionic polymeric surfactants, amphiphilic polymers, fatty acids, modified fatty acids, nonionic hydrophilic polymers, nonionic hydrophobic polymers, poly acrylic acids, poly methacrylic, acrylics, natural rubbers, synthetic rubbers, resins, amphiphilic anionic polymer and copolymers, amphiphilic cationic polymer and copolymers and mixtures thereof as well as emulsions or suspensions of these in water, alcohol, ketones, and other solvents.

Solutions or emulsions containing a lubricant may be employed as lubricants, for examples, resins and other hydrophobic lubricants may be applied as emulsions or in solvents suitable for dissolving them. Such solutions may contain any amount of the lubricant suitable for application to or incorporation into a biofabricated leather. For example, they may contain 1, 2, 3, 4, 5, 6, 7, 8, 9, 10, 15, 20, 25, 30, 35, 40, 45, 50, 55, 60, 70, 80, 90, 95, or 99% of a lubricant or the same, or a corresponding amount to volume of other ingredients, such as at least one aqueous solvent, such as water, alcohols, such $C_1$-$C_6$ alcohols, like ethanol, ketones, such as $C_1$-$C_6$ ketones, aldehydes, such as $C_1$-$C_6$ aldehydes, waxes, surfactants, dispersants or other agents. Lubricants may be in various forms, such as O/W or W/O emulsions, in aqueous or hydrophobic solutions, in sprayable form, or other forms suitable for incorporation or application to a biofabricated material.

Lubricants can be distributed uniformly throughout a biofabricated material such that the concentration of the lubricant in identical unit volumes of the material varies by no more than 5, 10, 15, 20, 35, 30, 40, or 50% and may be compounded or mixed into forms suitable for uniform application to or into a biofabricated material.

Some embodiments of a biofabricated product exhibit many advantageous properties similar to leather or new or superior properties compared to conventional leather.

In other embodiments a biofabricated leather can have an elastic modulus of at least 100 kPa. It can range from 100 kPa to 1,000 MPa as well as any intermediate value in this range, such as 0.1, 0.2, 0.3, 0.4, 0.5, 0.6, 0.7, 0.8, 0.9, 1, 2, 3, 4, 5, 6, 7, 8, 9, 10, 50, 100, 200, 300, 400, 500, 600, 700, 800, 900, or 1,000 MPa.

Some embodiments will exhibit a uniform elasticity, wherein the elastic modulus varies by no more than 5, 10, 15, 20, 25, 30, 35, 40, 45, or 50% when measured at angles differing by 30, 60, or 90 degrees (or at other angles) across identical lengths or widths (or volumes or fixed cross-sectional areas) of the material.

Some embodiments are stretchable and can be elongated by 1, 2, 3, 4, 5, 6, 7, 8, 9, 10, 15, 20, 25, 30, 40, 50, 60, 70, 80, 90, 100, 150, 200, 250 to 300% of its length in a relaxed state. This range includes all intermediate values.

In some embodiments, a biofabricated leather can have a tensile strength of at least 1 kPa. It can range from 1 kPa to 100 MPa as well as any intermediate value in this range, such as 1, 2, 3, 4, 5, 6, 7, 8, 9, 10, 50, 100, 200, 300, 400, 500 kPa; 0.5, 0.6, 0.7, 0.8, 0.9, 1.0, 1.1, 1.2, 1.3, 1.4, 1.5, 2, 3, 4, 5, 6, 7, 8, 9, 10, 20, 30, 40, 50, 60, 70, 80, 90, or 100 MPa. Some embodiments will exhibit a uniform tensile strength, wherein the tensile strength varies by no more than 5, 10, 15, 20, 25, 30, 35, 40, 45, or 50% when measured at angles differing by 30, 60, or 90 degrees (or at other angles) across identical lengths or widths (or volumes or fixed cross-sectional areas) of the material.

Some biofabricated leathers exhibit tear strength or resistance of at least 1, 2, 3, 4, 5, 6, 7, 8, 9, 10, 15, 20, 25, 30, 35, 40, 45, 50, 100, 150 or 200% more than that of a conventional top grain or other leather of the same thickness comprising the same type of collagen, e.g., bovine Type I or Type III collagen, processed using the same crosslinker(s) or lubricants. Some embodiments will exhibit a uniform tear resistance which varies by no more than 5, 10, 15, 20, 25, 30, 35, 40, 45, or 50% when measured at angles differing by 30, 60, or 90 degrees (or at other angles) across identical lengths or widths (or volumes or fixed cross-sectional areas) of the material. A biofabricated material may have a tear strength ranging from about 1 to 500 N, for example, 1, 2, 3, 4, 5, 6, 7, 8, 9, 10, 20, 30, 40, 50, 60, 70, 80, 90, 100, 125, 150, 175, 200, 225, 250, 275, 300, 325, 350, 375, 400, 425, 450, 475, or 500 as well as any intermediate tear strength within this range.

A biofabricated leather may have a softness as determined by ISO 17235 of 2, 3, 4, 5, 6, 7, 8, 10, 11, 12 mm or more. v. Some embodiments will exhibit a uniform softness which varies by no more than 5, 10, 15, 20, 25, 30, 35, 40, 45, 50, or 100% when measured in otherwise identical unit areas or volumes of the biofabricated material.

In other embodiments, a biofabricated material exhibits a customized thickness to provide top grain like products without the requirement for corium backing. In some embodiments the material will have a top and bottom surface or an inner and outer surface which have identical or substantially the same grain, grain texture, feel, and appearance. Other embodiments are embossed with a pattern, distressed, or printed, stained or painted. Other embodiments have a surface coating or surface finish, which may be distributed uniformly on or throughout the material such that its concentration by weight in identical unit volumes or over unit areas of the material varies by no more than 5, 10, 15, 20, 25, 30, 35, 40, 45, or 50%. Some embodiments may contain a dye, stain, resin, polymer, pigment or paint, optionally, wherein the dye, stain, resin, polymer, pigment or paint is distributed uniformly throughout the material such that its concentration by weight in identical unit volumes or on unit areas of the material varies by no more than 5, 10, 15, 20, 25, 30, 35, 40, 45, or 50%.

Certain embodiments of the biofabricated material described above may contain fillers as well as other substances or components incorporated into the network of collagen fibrils. For example, some embodiments will contain a filler, such as at least one of polymeric microsphere(s), bead(s), fiber(s), wire(s), or organic salt(s). These can be selected so as to control the organization of the dehydrated collagen fibril network by keeping the fibrils spaced apart during drying. A filler may be soluble under some conditions or otherwise in a form that permits it removal from a biofabricated material after drying or other processing.

Other embodiments include at least one woven or non-woven material incorporated into the network of collagen fibrils or a network of collagen fibers incorporated into the nonwoven or woven material.

In some embodiments the biofabricated material will be incorporated into other products such as footwear, clothing, sportswear, uniforms, wallets, watchbands, bracelets, luggage, upholstery, or furniture.

Embodiments of the Method of Making

The method according to the invention includes, but is not limited to, the following embodiments.

A method for making:

(i) a material comprising a network of non-human collagen fibrils, wherein less than 1, 2, 3, 4, 5, 6, 7, 8, 9, 10, 15, 20, 25, 30, 35 or 40% by weight of the collagen fibrils in the material are in the form of collagen fibers having a diameter of 1, 2, 3, 4, 5, 6, 7, 8, 9, 10 μm or more and/or are in the form of fibrils aligned for 25, 50, 100, 150, 200, 250, 300, 350 or 400 μm or more of their lengths; wherein said material contains no more than 10, 15, 20, 25, 30, 35, 40, 45, 50, 55 or 60% by weight water; and wherein said material contains at least 1, 2, 3, 4, 5, 6, 7, 8, 9, 10, 20, 30, or 40% of a lubricant, comprising in any order: fibrillating an aqueous solution or suspension of non-human collagen molecules into collagen fibrils, crosslinking said collagen fibrils by contacting them with at least one crosslinking agent, dehydrating the crosslinked collagen fibrils so that they contain less than 40% by weight water, incorporating at least 1, 2, 3, 4, 5, 6, 7, 8, 9, 10, 20, 30, or 40% by weight of at least one lubricant into said material, and, optionally, casting, molding, or otherwise forming said material that comprises a top and bottom surface or an inner and outer surface; or (ii) a material comprising a network of recombinant non-human collagen fibrils, wherein the collagen contains substantially no 3-hydroxyproline, and, optionally, substantially no hydroxylysine; wherein said material contains no more than 10, 15, 20, 25, 30, 35, 40, 45, 50, 55 or 60% by weight water; and wherein said material contains at least 1% of a lubricant comprising in any order: fibrillating an aqueous solution or suspension of non-human collagen molecules into collagen fibrils, crosslinking said collagen fibrils by contacting them with at least one crosslinking agent, dehydrating the crosslinked collagen fibrils so that they contain no more than 5, 10, 15, 20 or 25% by weight water, and incorporating at least 1, 2, 3, 4, 5, 10, 15, 20, 30, 40, or 50% by weight of at least one lubricant into said material, and, optionally, casting, molding, or otherwise forming said material that comprises a top and bottom surface or an inner and outer surface.

The collagen or collagenous material for use in this method may comprise mammalian collagen, such as bovine Type I, Type III collagen or the other types and sources of collagens or collagenous proteins described herein. It may be obtained from a mammal or other animal or, in some embodiments expressed recombinantly by *Escherichia coli*, *Bacillus subtilis*, or another bacterium; by *Pichia*, *Saccharomyces*, or another yeast or fungi; by a plant cell; by an insect cell or by a mammalian cell.

Collagen for use in the methods disclosed herein may also be isolated from cells, such as those described above, that are cultured in vitro, such as from cultured mammalian or animal cells. Alternatively, collagen or collagenous proteins may be obtained by other means, such as by chemical synthesis. It may different in chemical structure from collagen obtained from a natural source, for example, if may contain a lower content of, or substantially no hydroxylysine or 3-hydroxyproline, glycosylated or crosslinked amino acid residues, or other post-translational modifications of a collagen amino acid sequence. Alternatively, it may contain a higher content of hydroxylated amino acid residues, glycosylated residues, crosslinks or other chemical modifications.

Preferably a collagen will not contain hair, hair follicle(s), or fat(s) of an animal that naturally expresses the collagen molecules it contains as these can detract from its uniformity, strength and aesthetic properties. For example, it may contain less than 1, 2, 3, 4, 5, 6, 7, 8, 9, or 10% by weight of actin, keratin, elastin, fibrin, albumin, globulin, mucin, mucinoids, noncollagen structural proteins, and/or noncollagen nonstructural proteins found in conventional leather. It may be substantially free of other collagenous proteins, carbohydrates, nucleic acids, or lipids, or immunogens, antigens, or allergens found in a conventional leather, such as an animal that naturally expresses the collagen molecules in a biofabricated material.

In some embodiments a collagen or collagen-like material for use in the methods described herein may be purified to substantial homogeneity or may have a degree of purity not inconsistent with its ability to form fibrils, for example, it may contain 25, 30, 40, 50, 60, 70, 80, 90, 95 or 99% by weight collagen based on its total protein content or based on its total weight. Mixtures of different types of collagen or collagens from different biological sources may be used in certain embodiments to balance the chemical and physical properties of collagen fibrils or to produce a mixture of fibrils having complementary properties. Such mixtures may contain 1, 5, 10, 25, 50, 75, 95, or 99% by weight of a first collagen and 99, 95, 90, 75, 50, 25, 10 or 1% by weight of a second, third, or subsequent collagen component. These ranges include all intermediate values and ratios of collagens where the total collagen content of all collagen components by weight is 100%.

The methods disclosed herein can provide a biofabricated product having substantially uniformly distributed fibrils, crosslinked fibrils, dehydrated fibrils and/or lubricated fibrils. For example, the fibrils may be distributed throughout the material so that the concentration by weight (or by number or average numbers) of the collagen fibrils in identical unit volumes of the material varies by no more than 5, 10, 15, 20, 25, 30, 35, 40, 45, or 50%.

In some embodiments the biofabricated material will be staking the material after the crosslinking, dehydrating and/or lubricating.

In the embodiments described herein, a collagen solution or suspension is fibrillated, for example, by adjusting a salt concentration of the solution or suspension, by adjusting its pH, for example, raising the pH of an acidic solution of collagen, or both. In some embodiments, fibrillation may be facilitated by including a nucleating agent. Salts used for fibrillation include but are not limited to phosphate salts and chloride salts, such as $Na_3PO_4$, $K_3PO_4$, KCl, and NaCl. Salt concentration during fibrillation may be adjusted to range from 10 mM to 2M, or pH may be adjusted to pH 5.5, 6.0, 6.5, 7.0, 8.0 or more with an acid, a base, or a buffer. Salt concentration and pH may be simultaneously adjusted to induce or promote fibrillation. In certain embodiments of the methods described herein an aqueous solution or suspension of collagen molecules having a pH below pH 6.0 can be fibrillated by adjusting the pH to pH 6.0 to 8.0.

In some embodiments of the methods described herein, the collagen fibrils will be crosslinked during a process of their formation or after completion of fibrillation.

In some embodiments, collagen fibrils are crosslinked by contacting them with at least one amine, carboxylic acid, sulfate, sulfite, sulfonate, aldehyde, hydrazide, sulfhydryl, diazirine, aryl, azide, acrylate, epoxide, phenol, chromium compound, vegetable tannin, and syntan.

One or more crosslinkers may be added at a concentration ranging from 1 mM to 100 mM, for example at a concentration of 1, 2, 3, 4, 5, 6, 7, 8, 9, 10, 15, 20, 25, 30, 35, 40, 45, 50, 55, 60, 6, 70, 75, 80, 85, 90, 95 or 100 mM.

The time, temperature and other chemical and physical conditions of crosslinking may be selected to provide a particular degree of crosslinking among the collagen fibrils so that the resulting crosslinked fibrils contain a particular degree of one or more different crosslinkages. A resulting crosslinked fibril preparation may contain at least 1, 2, 3, 4, 5, 6, 7, 8, 9, 10% or more of a crosslinking agent based on the weight of the crosslinking agent and the weight of the collagen or on the weight of a crosslinked network of collagen fibrils, such as a hydrogel. The crosslinker may be covalently- or non-covalently bound to the collagen fibrils. The numbers of crosslinks between or among collagen molecules, tropocollagen, or fibrils in identical unit volumes of the material after crosslinking, or an average number of crosslinks between collagen molecules, tropocollagen, or collagen fibrils, may vary by no more than 5, 10, 15, 20, 25, 30, 35, 40, 45, or 50%.

The methods described herein require a dehydration or dewatering step which may occur during fibrillation or crosslinking, or both, or after fibrillation and crosslinking are substantially complete.

In some embodiments, dehydrating involves contacting a network of collagen fibrils with acetone, syntan, or other agent that removes bound water from collagen. In other embodiments, some water may be removed from a fibril preparation or crosslinked fibril preparation by filtration or evaporation and water remaining associated with the network of collagen fibrils then removed using a solvent such as acetone or other chemical agents that remove water.

The methods described herein generally require lubrication of the network of collagen fibrils produced. Lubrication may take place during fibrillation, crosslinking, of dehydration, or during any of these steps, or after one or more of these steps is substantially complete.

In some embodiments lubrication will involve contacting a network of crosslinked collagen fibrils with one or more lubricants such as fats, biological, mineral or synthetic oils, cod oil, sulfonated oil, polymers, organofunctional siloxanes, and other agent used for fatliquoring conventional leather; or mixtures thereof.

In other embodiments, lubricant(s) will be applied using methods that facilitate uniform lubrication of a dehydrated crosslinked network of collagen fibrils, so that the concentration of the lubricant by weight in identical unit volumes of the material varies by no more than 5, 10, 15, 20, 25, 30, 35, 40, 45, or 50%. Such application may occur by dip-coating, spray-coating, vapor deposition, spin-coating, Doctor Blade coating, brush coating as well as other known coating or deposition methods.

In further embodiments of the methods described herein, a surface coating or surface finish is applied to a biofabricated material. While these may be applied to a surface of a material comprising a network of collagen fibrils during the various steps of the preparation of a biofabricated material, they will generally be applied to a crosslinked, dehydrated and lubricated product. The uniform lubrication made possible by the methods described herein facilitate the successful uniform application and adherence of such coatings or finishes.

In other embodiments, the methods described herein can include incorporating or contacting a biofabricated material during the various steps of its preparation or after it has been crosslinked, dehydrated and lubricated with other functional ingredients including, but not limited to a dye, stain, pigment, resin, polymer, or paint. In further embodiments, these functional ingredients may be applied or incorporated under conditions that uniformly distribute these agents on or throughout the material so that their concentration by weight in identical unit volumes of the material varies by no more than 5, 10, 15, 20, 25, 30, 35, 40, 45, or 50%.

In other embodiments, the method described herein involves incorporating a filler into a biofabricated material during the various steps of its preparation or after it has been crosslinked, dehydrated and lubricated. Generally, these fillers are incorporated prior to dehydration, for example, during fibrillation or crosslinking. Such fillers include, but are not limited to polymeric microspheres, beads, fibers, wires, or organic salts.

Some embodiments of the methods described above will involve incorporating into or onto a biofabricated material during or after its preparation at least one woven or nonwoven material. For example, by filtering crosslinked fibrils using a woven or nonwoven paper or fabric material. Other embodiments involve incorporating a biofabricated material during or after its preparation into at least one woven or nonwoven material.

Commercial embodiments of the method involving incorporating a biofabricated material into products such as footwear, clothing, sportswear, uniforms, wallets, watchbands, bracelets, luggage, upholstery, furniture, or other industrial, commercial or consumer products.

The following non-limiting Examples are illustrative of the present invention. The scope of the invention is not limited to the details described in these Examples.

EXAMPLE 1

Controlling the Thickness of Biofabricated Leather

Hydrogels of extracted bovine type I collagen were formed at different collagen concentrations and volumes to produce dried collagen materials of different thicknesses. Collagen was dissolved in 0.01N HCl at either 5 g/L or 9 g/L, then 1 part 10× PBS was added to 9 parts dissolved collagen to induce collagen fibrillation and gel formation.

Solutions of either 0.8 L or 1.6 L of the fibrillating collagen were then cast into molds and incubated at 25° C. to allow hydrogel formation. The 0.8 L solution produced a gel of 1.5 cm thickness while the 1.7 L solution produced a gel of 3.0 cm thickness. These gels were dehydrated and lubricated in acetone, then dried and mechanically staked into a leather like material. The thickness of the final dried material correlated with the total amount of collagen in the starting hydrogel.

The thickness of biofabricated leather was controlled by varying its total collagen content. Samples A, B and C were produced using 4, 7.2 or 14.4 gr of collagen, respectively, in a volume (hydrated gel area) of 525 cm². Biofabricated leathers were produced from each sample by crosslinking, lubricating and dewatering As shown in Table 1, increasing the content of collagen in the gels increased the thickness of the resulting biofabricated leather.

TABLE 1

| Sample | Gel Density (g/L) | Gel Volume (L) | Gel Thickness (cm) | Total Collagen (g) | Leather Thickness (mm) |
|---|---|---|---|---|---|
| A | 5 | 0.8 | 1.5 | 4 | 0.1 |
| B | 9 | 0.8 | 1.5 | 7.2 | 0.2 |
| C | 9 | 1.6 | 3.0 | 14.4 | 1.1 |

EXAMPLE 2

Production of Biofabricated Leather from Type I Collagen

Type I collagen was purchased from Wuxi Biot Biotechnology Company, ltd. (Medical Collagen Sponge). The collagen was isolated from bovine tendon by acid treatment followed by pepsin digestion, and was purified by size exclusion chromatography, frozen and lyophilized.

The lyophilized protein (4.1 g) was dissolved in 733 ml 0.01 N HCL using an overhead mixer. After the collagen was adequately dissolved, as evidenced by a lack of solid collagen sponge in the solution (at least 1 hr mixing at 1600 rpm), 82 uL of the tanning agent Relugan GTW was added to the solution followed by 81 mL of a 10× PBS, pH 11.2 to raise the pH of the solution to 7.2.

The solution was then mixed for 3 min before pouring the solution into a silicon mold. The collagen solution was incubated in the silicon mold for 2 hrs at 25° C. to allow the collagen to fibrillate into a viscoelastic hydrogel.

Plateau of rheological properties along with solution opacity (as measured by absorbance of 425 nm light) indicated that fibrillation was complete at this point and the presence of collagen fibrils was confirmed with scanning electron microscopy (FIG. 3) and transmission electron microscopy (FIG. 4).

The fibrillated collagen hydrogel was removed from the molds and placed in 700 mL of acetone in a plastic jar and shaken on an orbital shaker at 40 rpm at 25° C. The hydrogel was dehydrated by refreshing the acetone after an overnight incubation followed by 5×1 hr washes and another overnight incubation. Acetone was refreshed after each wash to remove water from the gel.

Following acetone dehydration, the collagen gel was incubated in a fat liquor solution containing 20% (v/v) of either cod liver oil or castor oil in 80% acetone or ethanol, respectively, overnight while shaking at 40 rpm.

Following incubation in the fat liquor solution, the collagen gel was dried at 37 C. After drying, the material became soft and leather-like or a biofabricated leather. Excess oil can be removed to improve the leather-like aesthetic of the materials.

The biofabricated leather had a grain texture on both the top and bottom surfaces and consistently absorbed dyes on both the top and bottom surfaces.

EXAMPLE 3

Production of Biofabricated Leather from Type III Collagen

A solution of recombinant collagen type III at 2.5 mg/ml in 0.01 N HCl (FibroGen, Inc.) was fibrillated by adding 1 part of a 200 mM of sodium phosphate solution (22 mL), pH 11.2 to 9 parts of the collagen solution (200 mL) to increase the pH to 7 and stirred 2 hours at room temperature.

Fibrillation was confirmed by measuring 400 nm absorbance of the solution over time.

After fibrillation, the fibrils were tanned by adding Relugan GTW (2% w/w offer on the collagen) to the fibril suspension and mixing for 30 min.

The tanned collagen fibrils were then centrifuged at 3,500 RPM for 30 minutes to concentrate the fibrils to a concentration of 10 mg/ml. The 10 mg/ml fibril pellet was further centrifuged using an ultra-centrifuge at 21,000 RPM for 30 minutes yielding a fibril gel with a concentration of ~40-50 mg/ml.

The physical properties of the fibril gel were assessed with a rheometer.

The storage modulus and complex viscosity demonstrate a mostly elastic material.

This fibril gel was then dried in a food dehydrator set to 37° C. for 18 hrs.

After drying, the material was dyed and retanned by incubating in a solution of Lowepel acid black dye (2% w/w offer on the collagen) and Lubritan WP (20% w/w offer on the collagen).

The material was drummed in this solution and squeezed to ensure penetration of dye and syntan into the material. The material was then finally dried and staked to produce a leather-like material.

EXAMPLE 4

Production of Biofabricated Leather from Type III Collagen

Recombinant collagen type III was purchased from Fibrogen, Inc. The collagen was supplied at a concentration of 2.5 mg/mL in 0.01N HCl.

To initiate the assembly of collagen fibrils, 1 part 200 mM $Na_2HPO_4$, pH 11.2 (100 mL) was added to 9 parts of the stock collagen type III solution at room temperature to bring the solution to pH 7.2. The solution was mixed at 1600 rpm for 1 hr using an overhead mixer.

After 1 hr of stirring, the collagen fibrils were reacted with Relugan GTW which was added to the solution at a 2% (w/w) offer on the mass of the collagen. The solution was mixed at 1600 rpm for 1 hr using an overhead mixer.

Lipoderm A1 and Tanigan FT were then added to the solution at offers of 80% (w/w) each on the mass of the collagen. The solution was mixed at 1600 rpm for 30 min using an overhead mixer. The pH of the solution was then lowered to 4 using a 10% (v/v) formic acid solution. The solution was mixed at 1,600 rpm for 30 min using an overhead mixer.

144 mL of the solution was then filtered through a 47 mm Whatman no. 1 membrane using a Buchner funnel attached to a vacuum pump (pressure of −27 in Hg) and a rubber dam on top of the Buchner funnel. Vacuum was pulled for 18 hrs.

The concentrated fibril tissue was then allowed to dry under ambient conditions and hand staked for 30 min by rolling, bending and pulling the material to produce a leather-like material.

EXAMPLE 5

Expancell

Type I bovine collagen, isolated from bovine tendon by acid treatment followed by pepsin digestion and purified by size exclusion chromatography, frozen and lyophilized, was purchased from Wuxi Biot Bio-technology co., Ltd. (Medical Collagen Sponge).

Using an overhead mixer, 10 gr of the lyophilized collagen protein was dissolved by mixing at 1,600 rpm in 1 L of 0.01N HCl, pH 2, for at least one hour until no solid collagen sponge was present.

111.1 ml of 200 mM sodium phosphate (pH adjusted to 11.2 with sodium hydroxide) was then added to raise the pH of the collagen solution to 7.2.

The pH 7.2 collagen solution was then stirred for 10 minutes and 0.1 ml of a 20% Relugan GTW (BASF) as a crosslinker, which was 2% on the weight of collagen, was added to produce crosslinked collagen fibrils.

The crosslinked collagen fibrils were then mixed with 5 ml of 20% Tanigan FT (Lanxess) and stirred for one hour.

Subsequently, 1 gr of Expancel Microspheres 461 WE 20 d36 (AkzoNobel), which is 10% of the weight of the collagen) and 40 ml of Truposol Ben (Trumpler), which is 80% of the weight of the collagen, were added and stirred for an additional hour using an overhead stirrer.

The pH of the solution was the reduced to pH 4.0 by addition of 10% formic acid and stirred for an hour.

After the reduction in pH, 150 ml of the solution was filtered through 90 mm Whatman No. 1 membrane using a Buchner funnel attached to a vacuum pump at a pressure of −27 mmHg.

The concentrated fibril tissue was then allowed to dry under ambient conditions and hand staked for 30 minutes by rolling, bending and pulling the material to produce a leather-like material.

EXAMPLE 6

Titanium Dioxide (White Pigment)

Type I bovine collagen was purchased from Wuxi Biot Bio-technology co., Ltd. (Medical Collagen Sponge). This source of collagen is type I collagen isolated from bovine tendon by acid treatment followed by pepsin digestion and purified by size exclusion chromatography, frozen and lyophilized. The lyophilized protein (10 grams) was dissolved in 1 L of 0.01N HCl, pH 2 using an overhead mixer. After the collagen was adequately dissolved, as evidenced by a lack of solid collagen sponge in the solution (at least 1 hr mixing at 1,600 rpm), 111.1 ml of 200 millimolar sodium phosphate (pH adjusted to 11.2 with sodium hydroxide) to raise the pH of the solution to 7.2. The resulting collagen solution was stirred for 10 minutes and 0.1 ml of a 20% Relugan GTW (BASF) crosslinker solution, which was 2% on the weight of collagen.

To the crosslinked collagen fibril solution was added 5 mls of 20% Tanigan FT (Lanxess) was added followed by stirring for one hour.

Following Tanigan-FT addition, 1 gr Expancel Microspheres (10% on the weight of collagen) 461 WE 20 d36 (AkzoNobel), 40 mls (80% on the weight of collagen) of Truposol Ben (Trumpler) and 2 mls (10% on the weight of collagen) of PPE White HS a pa (Stahl) was added and stirred for additional hour using an overhead stirrer.

The pH of the solution was reduced to 4.0 using 10% formic acid and stirred for an hour.

After pH change, 150 ml of the solution was filtered through 90 mM Whatman No. 1 membrane using a Buchner funnel attached to a vacuum pump at a pressure of −27 mmHg.

The concentrated fibril tissue was then allowed to dry under ambient conditions and hand staked for 30 minutes by rolling, bending and pulling the material to produce a leather-like material.

EXAMPLE 7

Hycar Resin (26552)

Bovine collagen was purchased from Wuxi Biot Biotechnology co., Ltd. (Medical Collagen Sponge). This source of collagen is type I collagen isolated from bovine tendon by acid treatment followed by pepsin digestion and purified by size exclusion chromatography, frozen and lyophilized.

The lyophilized protein (10 grams) was dissolved in 1 liter of 0.01N HCl, pH 2 using an overhead mixer. After the collagen was adequately dissolved, as evidenced by a lack of solid collagen sponge in the solution (at least 1 hr mixing at 1600 rpm), 111.1 ml of 200 mM sodium phosphate (pH adjusted to 11.2 with sodium hydroxide) to raise the pH of the solution to 7.2.

The resulting collagen solution was stirred for 10 minutes and 0.1 ml of a 20% Relugan GTW (BASF) crosslinker solution, which was 2% of the weight of the collagen, tanning agent solution was added.

To the crosslinked collagen fibril solution was added 5 mls of 20% Tanigan FT (Lanxess) was added and stirred for one hour. Following Tanigan-FT addition, 1 gram Expancel Microspheres (10% on the weight of collagen) 461 WE 20 d36 (AkzoNobel), 40 mls (80% on the weight of collagen) of Truposol Ben (Trumpler) and 2 mls (10% on the weight of collagen) of PPE White HS a pa (Stahl) was added and added and stirred for additional hour using an overhead stirrer.

The pH of the solution was reduced to 4.0 using 10% formic acid and a variety of offers of Hycar Resin 26552 (Lubrizol) was added and stirred for an additional hour. Following pH change and resin addition 150 ml of the solution was filtered through 90 millimeter Whatman No. 1 membrane using a Buchner funnel attached to a vacuum pump at a pressure of −27 mmHg. To facilitate activation, the Hycar Resin 26552 is mixed with the fibril solution and heated at 50° C. for 2 hrs.

The concentrated fibril tissue was then allowed to dry under ambient conditions and hand staked for 30 minutes by rolling, bending and pulling the material to produce a leather-like material. The addition of resin lead to improved mechanical properties as shown below in FIG. 1.

| Example | Substrates | Crosslinker | Dehydrator | Lubricant | Result |
|---|---|---|---|---|---|
| 5 | Type I collagen + Expancel microspheres | Relugan GTW | Tanigan FT | Truposol | Leather-like material |
| 6 | Type I collagen + Expancel microspheres | Relugan GTW | Tanigan FT | " | Leather-like material |
| 7 | Type I collagen + Expancel microspheres | Relugan GTW | Tanigan FT | " | Leather-like material, better mechanical properties |

Relugan is a returning agent based on polymer, resin or aldehyde. Tanigan is a sulfone-based syntan. Truposol Ben is a fatliquor for chrome-free leather. Lipoderm Liquor A1 is a fatliquor based on long chain alcohol, paraffin, anionic surfactants, in water Hycar Resin 26552: formaldehyde-free acrylic based emulsion Interpretation of Description Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "substantially", "about" or "approximately," even if the term does not expressly appear. The terms "substantially", "substantially no", "substantially free", "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

INCORPORATION BY REFERENCE

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The invention claimed is:

1. A collagen-based material, comprising:
a network of recombinant non-human collagen fibrils;
5% to 25% water by weight of the collagen-based material; and
0.1% to 60% of a lubricant by weight of the collagen-based material,
wherein 1% to 40% by weight of the recombinant non-human collagen fibrils within the network of recombinant-non-human collagen fibrils are assembled in the form of recombinant collagen fibers comprising a plurality of the recombinant non-human collagen fibrils, and
wherein each of the recombinant collagen fibers has a diameter in a range of 1 μm to 10 μm.

2. The collagen-based material of claim 1, further comprising: (a) a top surface and a bottom surface, or (b) an inner surface and an outer surface.

3. The collagen-based material of claim 1, wherein the recombinant-non-human collagen fibrils comprise at least one of bovine Type I collagen or bovine Type III collagen.

4. The collagen-based material of claim 1, wherein the collagen fibrils comprise collagen that has been recombinantly produced in the yeast *Pichia*.

5. The collagen-based material of claim 1, wherein the collagen fibrils comprise collagen that has been recombinantly produced in *Escherichia coli*.

6. The collagen-based material of claim 1, wherein the network of recombinant non-human collagen fibrils contains substantially no hair, hair follicles, or animal fat.

7. The collagen-based material of claim 1, further comprising greater than 0% to less than, or equal to, 1% of a non-collagen protein by weight of the collagen-based material, wherein the non-collagen protein is selected from the group consisting of actin, keratin, elastin, fibrin, albumin, globulin, mucin, mucinoids, non-collagen structural protein, and non-collagen nonstructural protein.

8. The collagen-based material of claim 1, wherein the recombinant non-human collagen fibrils are crosslinked.

9. The collagen-based material of claim 1, further comprising 1% to 10% of a crosslinking agent by weight of the collagen-based material, wherein the crosslinking agent is covalently bound or non-covalently bound to the recombinant non-human collagen fibrils.

10. The collagen-based material of claim 1, wherein the lubricant is selected from the group consisting of fat, biological oil, mineral oil, synthetic oil, sulfonated oil, polymer, organofunctional siloxane, and a combination thereof.

11. The collagen-based material according to claim 1, wherein the lubricant is distributed substantially uniformly throughout the collagen-based material.

12. The collagen-based material of claim 1, wherein the collagen-based material has an elastic modulus in a range of 100 kPa to 1,000 MPa.

13. The collagen-based material of claim 1, wherein the collagen-based material has a tensile strength in a range of 1 MPa to 100 MPa.

14. The collagen-based material of claim 1, further comprising a surface coating or surface finish disposed on the network of recombinant non-human collagen fibrils.

15. The collagen-based material of claim 1, further comprising at least one of a dye, stain, resin, polymer, pigment or paint, wherein the dye, the stain, the resin, the pigment or the paint is distributed substantially uniformly throughout the collagen-based material.

16. The collagen-based material of claim 1, further comprising at least one filler, wherein the filler is distributed substantially uniformly throughout the collagen-based material.

17. The collagen-based material of claim 1, further comprising at least one of a woven fiber material or a nonwoven fiber material embedded in the network of recombinant non-human collagen fibrils, the woven fiber material or the nonwoven fiber material comprising at least one of: cotton, wool, cashmere, angora, linen, bamboo, bast, hemp, soya, seacell, fibers produced from milk proteins, silk, spider silk, chitosan, mycelium, cellulose, wood fibers, nylon, polyester, an elastomer, a polyester-polyurethane copolymer, an aramid, carbon fibers, fullerenes, glass fibers, silicon, mineral particles, mineral fibers, a metal, or a metal alloy.

18. The collagen-based material of claim 1, wherein the recombinant non-human collagen fibrils contain substantially no 3-hydroxyproline.

19. The collagen-based material of claim 1, wherein the recombinant non-human collagen fibrils contain substantially no hydroxylysine.

20. The collagen-based material of claim 1, wherein the recombinant collagen fibers comprise a diameter in a range of 5 μm to 10 μm.

21. The collagen-based material of claim 1, wherein the collagen-based material further comprises greater than 0% to less than, or equal to, 1% of actin by weight of the collagen-based material, and wherein the recombinant non-human collagen fibrils comprise recombinant non-human collagen isolated from cells that are cultured in vitro.

22. The collagen-based material of claim 1, wherein the recombinant non-human collagen fibrils comprise purified recombinant non-human collagen.

23. The collagen-based material of claim 1, wherein the collagen-based material comprises 25% to 99% by weight of recombinant non-human collagen based on a total protein content of the collagen-based material.

24. The collagen-based material of claim 1, wherein the recombinant collagen fibers comprise a diameter in a range of 1 μm to 5 μm.

25. The collagen-based material of claim 1, wherein each of the recombinant non-human collagen fibrils has a diameter in a range of 1 nm to 1 μm.

26. The collagen-based material of claim 1, wherein the network of recombinant non-human collagen fibrils comprising a collagen fibril density in a range of 1 mg/cc to 1,000 mg/cc.

* * * * *